(12) United States Patent
Li et al.

(10) Patent No.: US 11,168,138 B2
(45) Date of Patent: Nov. 9, 2021

(54) ANTI-PDL1, IL-15 AND TGF-BETA RECEPTOR COMBINATION MOLECULES

(71) Applicant: Altor Bioscience LLC, Miramar, FL (US)

(72) Inventors: Qiongzhen Li, Pembroke Pines, FL (US); Xiaoyun Zhu, Weston, FL (US); Hing C. Wong, Weston, FL (US)

(73) Assignee: Altor Bioscience, LLC, Culver City, CA (US)

( * ) Notice: Subject to any disclaimer, the term of this patent is extended or adjusted under 35 U.S.C. 154(b) by 100 days.

(21) Appl. No.: 16/365,587

(22) Filed: Mar. 26, 2019

(65) Prior Publication Data

US 2020/0002425 A1    Jan. 2, 2020

Related U.S. Application Data

(60) Provisional application No. 62/734,994, filed on Sep. 21, 2018, provisional application No. 62/648,373, filed on Mar. 26, 2018.

(51) Int. Cl.

| | | |
|---|---|---|
| C07K 14/71 | (2006.01) | |
| C07K 16/28 | (2006.01) | |
| A61K 39/395 | (2006.01) | |
| C07K 16/24 | (2006.01) | |
| C07K 14/715 | (2006.01) | |
| A61K 38/17 | (2006.01) | |
| C12N 15/62 | (2006.01) | |
| C12P 21/00 | (2006.01) | |
| A61K 38/00 | (2006.01) | |

(52) U.S. Cl.
CPC ...... *C07K 16/2863* (2013.01); *A61K 38/1793* (2013.01); *A61K 39/395* (2013.01); *C07K 14/7155* (2013.01); *C07K 16/244* (2013.01); *C12N 15/62* (2013.01); *C12P 21/00* (2013.01); *C07K 2317/53* (2013.01)

(58) Field of Classification Search
None
See application file for complete search history.

(56) References Cited

U.S. PATENT DOCUMENTS

| | | |
|---|---|---|
| 5,116,964 A | 5/1992 | Capon et al. |
| 5,541,087 A | 7/1996 | Lo et al. |
| 5,620,939 A | 4/1997 | Halasa et al. |
| 8,507,222 B2 | 8/2013 | Wong et al. |
| 2002/0016502 A1 | 2/2002 | Kanno et al. |
| 2002/0076406 A1 | 6/2002 | Leung |
| 2003/0039650 A1 | 2/2003 | Gruenberg |
| 2005/0203022 A1 | 9/2005 | Gotwals et al. |
| 2009/0238791 A1 | 9/2009 | Jacques et al. |
| 2012/0100099 A1 | 4/2012 | Wang et al. |
| 2015/0374790 A1 | 12/2015 | Liu et al. |
| 2016/0145340 A1 | 5/2016 | Borges et al. |
| 2016/0287664 A1 | 10/2016 | Yu et al. |
| 2017/0342119 A1 | 11/2017 | Liu et al. |

FOREIGN PATENT DOCUMENTS

| | | |
|---|---|---|
| WO | 9404689 A1 | 3/1994 |
| WO | 9429350 A2 | 12/1994 |
| WO | 9632478 A1 | 10/1996 |
| WO | 9734631 A1 | 9/1997 |
| WO | 2005046449 A2 | 5/2005 |

OTHER PUBLICATIONS

Liu et al, The Journal of Biological Chemistry; vol. 291, No. 46, pp. 23869-23881, Nov. 11, 2016.*
Mathios et al, Int. J. Cancer: 138, 187-19; online Jul. 2015.*
Alter et al, (Journal of Immunological Sciences; (2018); 2(1): 15-18).*
Horn et al, (AACR Special Conference on Tumor Immunology and Immunotherapy; Nov. 27-30, 2018).*
Debois et al, The Journal Immunology, 2016; vol. 197, pp. 168-178.*
Fujii et al, Cancer Immunology, Immunotherapy (2018) 67:675-689.*
Redman et al, Annals of Oncology; vol. 31, Supplement 4, Sep. 2020, p. S511.*
Béhar et al. (Nov. 25, 2010) "Evolution of Interleukin-15 for Higher *E. Coli* Expression and Solubility", Protein Engineering, Design and Selection, 24(3):283-290.
Benton et al. (Apr. 8, 1977) "Screening λgt Recombinant Clones by Hybridization to Single Plaques in Situ", Science, 196(4286):180-182.
Capon et al. (Feb. 9, 1989) "Designing CD4 Immunoadhesins for AIDS Therapy", Nature, 337(6207):525-531.
Chamow et al. (Feb. 1996) "Immunoadhesins: Principles and Applications", Trends Biotechnoloqy, 14:52-60.
Database Genbank (Sep. 21, 1994) "Human Interleukin 15 (IL15) mRNA, Complete cds", Genbank Accession No. U14407.1, 2 pages.
Database Genbank (Dec. 19, 1995) "Human Interleukin-15 Receptor Alpha Chain Precursor (IL15RA) mRNA, Complete cds", Genbank Accession No. U31628.1, 2 pages.
Database Genbank (Sep. 14, 1995) "Mus Musculus Interleukin 15 (IL15) mRNA, Complete cds", Genbank Accession No. U14332.1, 2 pages.
Database Genbank (May 20, 2005)"Mus Musculus Interleukin 15 Receptor, Alpha Chain, mRNA (cDNA clone Image:4457379), Complete cds", Genbank Accession No. BC095982.1, 2 pages.
Davis Mark M. (1985) "Molecular Genetics of the T Cell-receptor Beta Chain", Annual Review of Immunology, 3:537-560.

(Continued)

*Primary Examiner* — Bridget E Bunner
*Assistant Examiner* — Fozia M Hamud
(74) *Attorney, Agent, or Firm* — Sheridan Ross P.C.

(57) ABSTRACT

The invention features multi-specific protein complexes with one domain comprising IL-15 or a functional variant, a cytokine receptor or cytokine ligand, and a binding domain specific to a disease antigen, immune checkpoint or signaling molecule.

17 Claims, 34 Drawing Sheets
(33 of 34 Drawing Sheet(s) Filed in Color)
Specification includes a Sequence Listing.

(56) References Cited

OTHER PUBLICATIONS

Ellison et al. (Jul. 10, 1982) "The Nucleotide Sequence of a Human Immunoglobulin Cγ1 Gene", Nucleic Acids Research, 10(13):4071-4079.
Fleer Reinhard (Oct. 1992) "Engineering Yeast for High Level Expression", Current Opinion in Biotechnology, 3(5):486-496.
Frankel et al. (Oct. 2000) "Cell Surface Receptor-Targeted Therapy of Acute Myeloid Leukemia: A Review", Cancer Biotherapy & Radiopharmaceuticals, 15(5):459-476.
Galfre et al. (1981) "Preparation of Monoclonal Antibodies: Strategies and Procedures", Methods in Enzymology, 73(Pt. B)—3-46.
Gerber et al. (May/Jun. 2009) "Antibody Drug-conjugates Targeting the Tumor Vasculature—Current and Future Developments", mAbs, 1(3):247-253.
Graham et al. (Jul. 1977) "Characteristics of a Human Cell Line Transformed by DNA from Human Adenovirus Type 5", Journal of General Virology, 36(1):59-72.
Grunstein et al. (Oct. 1975) "Colony Hybridization: A Method for the Isolation of Cloned DNAs That Contain a Specific Gene", Proceedings of the National Academy of Sciences of the United States of America, 72(10):3961-3965.
Guo et al. (2013) "Therapeutic Cancer Vaccines: Past, Present and Future", Advances in Cancer Research, 119:421-475(45 pages).
Han et al. (Oct. 22, 2011) "IL-15:IL-15 Receptor Alpha Superagonist Complex: High-Level Co-Expression in Recombinant Mammalian Cells, Purification and Characterization", Cytokine, 56(3):804-810.
Kimmel Alan R. (1987) "Identification and Characterization of Specific Clones: Strategy for Confirming the Validity of Presumptive Clones", Methods in Enzymology, 152:507-511.
Moskaug et al. (Sep. 15, 1989) "Translocation of Diphtheria Toxin A—Fragment to the Cytosol. Role of The Site of Interfragment Cleavage", Journal of Biological Chemistry, 264(26):15709-15713.
Novellino et al. (Mar. 2005) "A Listing of Human Tumor Antigens Recognized by T Cells: Mar. 2004 Update", Cancer Immunology, Immunotherapy, 54(3):187-207.
Olsnes et al. (1982) "Chimeric Toxins", Pharmacology and Therapeutics, 15(3):355-381.
Pardoll Drew M. (Apr. 2012) "The Blockade of Immune Checkpoints in Cancer Immunotherapy", Nature Reviews Cancer, 12(4):252-264.
Parmiani et al. (Feb. 15, 2007) "Unique Human Tumor Antigens: Immunobiology and Use in Clinical Trials", The Journal of Immunology, 178(4):1975-1979.
Pastan et al. (Dec. 5, 1986) "Immunotoxins", Cell, 47:641-648.
Pastan et al. (1992) "Recombinant Toxins as Novel Therapeutic Agents", Annual Review Biochemistry, 61:331-354.
Sliwkowski et al. (Sep. 13, 2013) "Antibody Therapeutics in Cancer", Science, 341(6151):1192-1198.
Thaventhiran et al. (2012) "T Cell Co-inhibitory Receptors: Functions and Signalling Mechanisms", Journal of Clinical & Cellular Immunology, 12 pages.
Tomalia Donald A. (1993) "Starburst/Cascade Dendrimers: Fundamental Building Blocks for a New Nanoscopic Chemistry Set", Aldrichimica Acta, 26(4):89-101.
Urlaub et al. (Jul. 1980) "Isolation of Chinese Hamster Cell Mutants Deficient in Dihydrofolate Reductase Activity", Proceedings of the National Academy of Sciences, 77(7):4216-4220.
Wahl et al. (1987) "Molecular Hybridization of Immobilized Nucleic Acids: Theoretical Concepts and Practical Considerations", Methods in Enzymology, 152:399-407.
Waldmann Thomas A. (Aug. 2006) "The Biology of Interleukin-2 and Interleukin-15: Implications for Cancer Therapy and Vaccine Design", Nature Reviews Immunology, 6(8):595-601.
Weidle et al. (Jul.-Aug. 2013) "The Emerging Role of New Protein Scaffold-based Agents for Treatment of Cancer", Cancer Genomics and Proteomics, 10(4):155-168.
Whitlow et al. (Apr. 1991) "Single-Chain Fv Proteins and their Fusion Proteins", Methods: A Companion to Methods in Enzymology, 2(2):97-105.
Zhu et al. (Sep. 15, 2009) "Novel Human Interleukin-15 Agonists", Journal of Immunology, 183(6):3598-3607.
International Search Report and Written Opinion for International (PCT) Patent Application No. PCT/US2019/024077, dated Jul. 10, 2019 17 pages.
Preliminary Report on Patentability for International (PCT) Patent Application No. PCT/US2019/024077, dated Oct. 8, 2020 14 pages.
Official Action for Canadian Patent Application No. 3089333, dated Jun. 2, 2021 3 pages.

* cited by examiner

Early Protein Characterization

| Component | Cell Line | Assay |
|---|---|---|
| IL15 | 32Dβ | Proliferation assay |
| TGFβRII | TGF/SMAD Signaling Pathway SBE Reporter – HEK293 Cell | Blocking Assay |
| anti-PDL1 | H441 | Binding Assay (Fc) |
| | | Blocking Assay(Fc) |

32Dβ proliferation assay for IL-15 EC$_{50}$ N-810A, N810B, N810C

| | ALT-803 | N-810A αPDL1/TxM/TGFβ Nant Lot SP0102818n-msg (pool 1) | N-810B hTGFβRII/αPDL1/TxM Lot 20180619 Clone 2 | N-810C αPDL1/TGFβ/RII/TxM Lot 21080703 Clone 3-2-4D1 |
|---|---|---|---|---|
| EC50 | 39.26 | 10.71 | 557.9 | 411.7 |
| HillSlope | 0.9823 | 1.238 | 1.606 | 2.428 |
| R square | 0.9749 | 0.9842 | 0.9854 | 0.9948 |
| Fold difference from ALT-803 | | 0.3 | 14 | 10 |

|  | TGFβRII/αPDL1/TXM | αPDL1/TGFβRII/TXM |
|---|---|---|
| Protein expression | 70mg/L | 4mg/L |
| TGFβ Activity Blocking Assay IC50 | 2.47nM | 0.55nM |
| IL-15 Activity Assay EC50 | 0.259nM | 0.195nM |
| PDL1 Binding Assay EC50 | 0.20nM | 0.26nM |

TGFβRII/αPDL1/TxM

αPDL1/TGFβRII/TXM

TGFβRII/αPDL1/TxM

αPDL1/TGFβRII/TXM

PD-L1 Blockade Assay

N-810A aglycosylated

N-810A aglycosylated, Δfree cysteine

N-810A Δhinge

N-810A (IL15-K41Q,L45S,I67T,N79Y,E93A)
-Mutations in IL15 to enhance solubility and
expression N-810A (IL15-L45S)
-Mutations in IL15 to enhance solubility and
expression

| Protein | Post-harvest Titer (ug/mL) | Total Yield (mg) | High Molecular Weight % Post Pro-A |
|---|---|---|---|
| N-810A | 55.9 | | 20.4 |
| N-810 (IL15-K41Q, L45S,I67T,N79Y,E93A) | 156.3 | 6.7 | 18.1 |
| N810A (IL15-L45S) | 151.3 | 6.6 | 16.5 |
| N810D | 117.7 | | 8.8 |

SEQUENCE LISTING

```
<160> NUMBER OF SEQ ID NOS: 46

<210> SEQ ID NO 1
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agcccaaga agtgtgcgtg      240 gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga gaccttttc     840 atgtgctcct gcagcagcga cgaatgcaac gacaatatca tctttagcga ggaatacaat     900
accagcaacc ccgacatcac gtgtcctcct cctatgtccg tggaacacgc agacatctgg     960
gtcaagagct acagcttgta ctccagggag cggtacattt gtaactctgg tttcaagcgt    1020
aaagccggca cgtccagcct gacggagtgc gtgttgaaca aggccacgaa tgtcgcccac    1080
tggacaaccc ccagtctcaa atgcattaga gagccgaaat cttgtgacaa aactcacaca    1140
tgcccaccgt gcccagcacc tgaactcctg gggggaccgt cagtcttcct cttcccccca    1200
aaacccaagg acaccctcat gatctcccgg acccctgagg tcacatgcgt ggtggtggac    1260
```

-continued

```
gtgagccacg aagaccctga ggtcaagttc aactggtacg tggacggcgt ggaggtgcat    1320
aatgccaaga caaagccgcg ggaggagcag tacaacagca cgtaccgtgt ggtcagcgtc    1380
ctcaccgtcc tgcaccagga ctggctgaat ggcaaggagt acaagtgcaa ggtctccaac    1440
aaagccctcc cagcccccat cgagaaaacc atctccaaag ccaagggca gccccgagaa     1500 ccacaggtgt acaccctgcc cccatcccgg gatgagctga ccaagaacca ggtcagcctg    1560
acctgcctgg tcaaaggctt ctatcccagc gacatcgccg tggagtggga gagcaatggg    1620
cagccggaga acaactacaa gaccacgcct cccgtgctgg actccgacgg ctccttcttc    1680
ctctacagca agctcaccgt ggacaagagc aggtggcagc aggggaacgt cttctcatgc    1740
tccgtgatgc atgaggctct gcacaaccac tacacgcaga agagcctctc cctgtctcct    1800
ggtaaa                                                               1806
```

<210> SEQ ID NO 2
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Lys Trp Val Thr Phe Ile Ser Leu Leu Phe Leu Phe Ser Ser Ala
1               5                  10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255
```

```
Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg Glu Pro Lys Ser Cys Asp Lys Thr His Thr Cys Pro Pro Cys
    370                 375                 380

Pro Ala Pro Glu Leu Leu Gly Gly Pro Ser Val Phe Leu Phe Pro Pro
385                 390                 395                 400

Lys Pro Lys Asp Thr Leu Met Ile Ser Arg Thr Pro Glu Val Thr Cys
                405                 410                 415

Val Val Val Asp Val Ser His Glu Asp Pro Glu Val Lys Phe Asn Trp
            420                 425                 430

Tyr Val Asp Gly Val Glu Val His Asn Ala Lys Thr Lys Pro Arg Glu
        435                 440                 445

Glu Gln Tyr Asn Ser Thr Tyr Arg Val Val Ser Val Leu Thr Val Leu
    450                 455                 460

His Gln Asp Trp Leu Asn Gly Lys Glu Tyr Lys Cys Lys Val Ser Asn
465                 470                 475                 480

Lys Ala Leu Pro Ala Pro Ile Glu Lys Thr Ile Ser Lys Ala Lys Gly
                485                 490                 495

Gln Pro Arg Glu Pro Gln Val Tyr Thr Leu Pro Pro Ser Arg Asp Glu
            500                 505                 510

Leu Thr Lys Asn Gln Val Ser Leu Thr Cys Leu Val Lys Gly Phe Tyr
        515                 520                 525

Pro Ser Asp Ile Ala Val Glu Trp Glu Ser Asn Gly Gln Pro Glu Asn
    530                 535                 540

Asn Tyr Lys Thr Thr Pro Pro Val Leu Asp Ser Asp Gly Ser Phe Phe
545                 550                 555                 560

Leu Tyr Ser Lys Leu Thr Val Asp Lys Ser Arg Trp Gln Gln Gly Asn
                565                 570                 575

Val Phe Ser Cys Ser Val Met His Glu Ala Leu His Asn His Tyr Thr
            580                 585                 590

Gln Lys Ser Leu Ser Leu Ser Pro Gly Lys
        595                 600

<210> SEQ ID NO 3
<211> LENGTH: 1123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgaagtggg tgaccttcat cagcctgctg ttcctgttct ccagcgccta ctccaacatc      60
```

```
cagatgaccc agtcccctag ctccgtgtcc gcctccgtgg gagatcgggt gaccatcacc    120
tgtagggcct cccaggacat ctccaggtgg ctggcctggt accagcagaa gcccggcaag    180
gcccccaagc tgctgatcta cgccgcctcc tccctgcagt ccggagtgcc tagcaggttc    240
tccggctccg gatccggcac agacttcgcc ctgaccatct cctccctgca gcccgaggac    300
ttcgccacct actactgcca gcaggccgac tccaggttct ccatcacctt cggccagggc    360
accaggctgg agatcaagag ggggaggtgg cggatccgga ggtggaggtt ctggtggagg    420
tgggagtgag gtgcagctgg tgcagtccgg aggaggactg gtgcagcctg gcggatccct    480
gaggctgtcc tgtgccgctt ccggcttcac cttcagctcc tactccatga actgggtgag    540
gcaggcccct ggaaagggcc tggagtgggt gtcctacatc tccagctcct cctccaccat    600
ccagtacgcc gactccgtga agggcaggtt caccatctcc agggacaacg ccaagaactc    660
cctgtacctg cagatgaaca gcctgaggga cgaggacacc gccgtgtact actgcgccag    720
gggcgactat tactacggca tggacgtgtg gggccaggga accaccgtga ccgtgtcctc    780
caactgggtt aacgtaataa gtgatttgaa aaaaattgaa gatcttattc aatctatgca    840
tattgatgct actttatata cggaaagtga tgttcacccc agttgcaaag taacagcaat    900
gaagtgcttt ctcttggagt acaagttat ttcacttgag tccggagatg caagtattca    960
tgatacagta gaaatctga tcatcctagc aaacgacagt ttgtcttcta atgggaatgt   1020
aacagaatct ggatgcaaag aatgtgagga actggaggaa aaaatatta agaatttt    1080 gcagagtttt gtacatattg tccaaatgtt catcaacact tct                    1123
```

<210> SEQ ID NO 4
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ser Val Ser Ala Ser
                20                  25                  30

Val Gly Asp Arg Val Thr Ile Thr Cys Arg Ala Ser Gln Asp Ile Ser
            35                  40                  45

Arg Trp Leu Ala Trp Tyr Gln Gln Lys Pro Gly Lys Ala Pro Lys Leu
        50                  55                  60

Leu Ile Tyr Ala Ala Ser Ser Leu Gln Ser Gly Val Pro Ser Arg Phe
65                  70                  75                  80

Ser Gly Ser Gly Ser Gly Thr Asp Phe Ala Leu Thr Ile Ser Ser Leu
                85                  90                  95

Gln Pro Glu Asp Phe Ala Thr Tyr Tyr Cys Gln Gln Ala Asp Ser Arg
                100                 105                 110

Phe Ser Ile Thr Phe Gly Gln Gly Thr Arg Leu Glu Ile Lys Arg Gly
            115                 120                 125

Gly Gly Gly Ser Gly Gly Gly Gly Ser Gly Gly Gly Gly Ser Glu Val
        130                 135                 140

Gln Leu Val Gln Ser Gly Gly Gly Leu Val Gln Pro Gly Gly Ser Leu
145                 150                 155                 160

Arg Leu Ser Cys Ala Ala Ser Gly Phe Thr Phe Ser Ser Tyr Ser Met
```

```
                165                 170                 175
Asn Trp Val Arg Gln Ala Pro Gly Lys Gly Leu Glu Trp Val Ser Tyr
            180                 185                 190

Ile Ser Ser Ser Ser Thr Ile Gln Tyr Ala Asp Ser Val Lys Gly
        195                 200                 205

Arg Phe Thr Ile Ser Arg Asp Asn Ala Lys Asn Ser Leu Tyr Leu Gln
    210                 215                 220

Met Asn Ser Leu Arg Asp Glu Asp Thr Ala Val Tyr Tyr Cys Ala Arg
225                 230                 235                 240

Gly Asp Tyr Tyr Tyr Gly Met Asp Val Trp Gly Gln Gly Thr Thr Val
                245                 250                 255

Thr Val Ser Ser Asn Trp Val Asn Val Ile Ser Asp Leu Lys Lys Ile
            260                 265                 270

Glu Asp Leu Ile Gln Ser Met His Ile Asp Ala Thr Leu Tyr Thr Glu
        275                 280                 285

Ser Asp Val His Pro Ser Cys Lys Val Thr Ala Met Lys Cys Phe Leu
    290                 295                 300

Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
                325                 330                 335

Asn Gly Asn Val Thr Glu Ser Gly Cys Lys Glu Cys Glu Glu Leu Glu
            340                 345                 350

Glu Lys Asn Ile Lys Glu Phe Leu Gln Ser Phe Val His Ile Val Gln
        355                 360                 365

Met Phe Ile Asn Thr Ser
    370

<210> SEQ ID NO 5
<211> LENGTH: 1671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaagtggg tgaccttcat cagcctgctg ttcctgttct ccagcgccta ctccaacatc    60
cagatgaccc agtcccctag ctccgtgtcc gcctccgtgg gagatcgggt gaccatcacc   120
tgtagggcct cccaggacat ctccaggtgg ctggcctggt accagcagaa gcccggcaag   180
gcccccaagc tgctgatcta cgccgcctcc tccctgcagt ccggagtgcc tagcaggttc   240
tccggctccg gatccggcac agacttcgcc ctgaccatct cctccctgca gcccgaggac   300
ttcgccacct actactgcca gcaggccgac tccaggttct ccatcacctt cggccagggc   360
accaggctgg agatcaagag ggaggtggc ggatccggag gtggaggttc tggtggaggt   420
gggagtgagg tgcagctggt gcagtccgga ggagactgg tgcagcctgg cggatccctg   480
aggctgtcct gtgccgcttc cggcttcacc ttcagctcct actccatgaa ctgggtgagg   540
caggcccctg gaaagggcct ggagtgggtg tcctacatct ccagctcctc ctccaccatc   600
cagtacgccg actccgtgaa gggcaggttc accatctcca gggacaacgc caagaactcc   660
ctgtacctgc agatgaacag cctgagggac gaggacaccg ccgtgtacta ctgcgccagg   720
ggcgactatt actacggcat ggacgtgtgg ggccagggaa ccaccgtgac cgtgtcctcc   780
atcacgtgtc ctcctcctat gtccgtggaa cacgcagaca tctgggtcaa gagctacagc   840
```

```
ttgtactcca gggagcggta catttgtaac tctggtttca agcgtaaagc cggcacgtcc    900
agcctgacgg agtgcgtgtt gaacaaggcc acgaatgtcg cccactggac aaccccccagt   960
ctcaaatgca ttagagagcc gaaatcttgt gacaaaactc acacatgccc accgtgccca   1020
gcacctgaac tcctgggggg accgtcagtc ttcctcttcc ccccaaaacc caaggacacc   1080
ctcatgatct cccggacccc tgaggtcaca tgcgtggtgg tggacgtgag ccacgaagac   1140
cctgaggtca agttcaactg gtacgtggac ggcgtggagg tgcataatgc caagacaaag   1200
ccgcgggagg agcagtacaa cagcacgtac cgtgtggtca gcgtcctcac cgtcctgcac   1260
caggactggc tgaatggcaa ggagtacaag tgcaaggtct ccaacaaagc cctcccagcc   1320
cccatcgaga aaaccatctc caaagccaaa gggcagcccc gagaaccaca ggtgtacacc   1380
ctgcccccat cccgggatga gctgaccaag aaccaggtca gcctgacctg cctggtcaaa   1440
ggcttctatc ccagcgacat cgccgtggag tgggagagca atgggcagcc ggagaacaac   1500
tacaagacca cgcctcccgt gctggactcc gacggctcct tcttcctcta cagcaagctc   1560
accgtggaca agagcaggtg gcagcagggg aacgtcttct catgctccgt gatgcatgag   1620
gctctgcaca accactacac gcagaagagc ctctccctgt cctctggtaa a            1671
```

<210> SEQ ID NO 6
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ser Val Ser Ala Ser
            20                  25                  30

Val Gly Asp Arg Val Thr Ile Thr Cys Arg Ala Ser Gln Asp Ile Ser
        35                  40                  45

Arg Trp Leu Ala Trp Tyr Gln Gln Lys Pro Gly Lys Ala Pro Lys Leu
    50                  55                  60

Leu Ile Tyr Ala Ala Ser Ser Leu Gln Ser Gly Val Pro Ser Arg Phe
65                  70                  75                  80

Ser Gly Ser Gly Ser Gly Thr Asp Phe Ala Leu Thr Ile Ser Ser Leu
                85                  90                  95

Gln Pro Glu Asp Phe Ala Thr Tyr Tyr Cys Gln Gln Ala Asp Ser Arg
            100                 105                 110

Phe Ser Ile Thr Phe Gly Gln Gly Thr Arg Leu Glu Ile Lys Arg Gly
        115                 120                 125

Gly Gly Gly Ser Gly Gly Gly Gly Ser Gly Gly Gly Gly Ser Glu Val
    130                 135                 140

Gln Leu Val Gln Ser Gly Gly Gly Leu Val Gln Pro Gly Gly Ser Leu
145                 150                 155                 160

Arg Leu Ser Cys Ala Ala Ser Gly Phe Thr Phe Ser Ser Tyr Ser Met
                165                 170                 175

Asn Trp Val Arg Gln Ala Pro Gly Lys Gly Leu Glu Trp Val Ser Tyr
            180                 185                 190

Ile Ser Ser Ser Ser Ser Thr Ile Gln Tyr Ala Asp Ser Val Lys Gly
        195                 200                 205
```

```
Arg Phe Thr Ile Ser Arg Asp Asn Ala Lys Asn Ser Leu Tyr Leu Gln
    210                 215                 220

Met Asn Ser Leu Arg Asp Glu Asp Thr Ala Val Tyr Tyr Cys Ala Arg
225                 230                 235                 240

Gly Asp Tyr Tyr Tyr Gly Met Asp Val Trp Gly Gln Gly Thr Thr Val
            245                 250                 255

Thr Val Ser Ser Ile Thr Cys Pro Pro Met Ser Val Glu His Ala
        260                 265                 270

Asp Ile Trp Val Lys Ser Tyr Ser Leu Tyr Ser Arg Glu Arg Tyr Ile
            275                 280                 285

Cys Asn Ser Gly Phe Lys Arg Lys Ala Gly Thr Ser Ser Leu Thr Glu
290                 295                 300

Cys Val Leu Asn Lys Ala Thr Asn Val Ala His Trp Thr Thr Pro Ser
305                 310                 315                 320

Leu Lys Cys Ile Arg Glu Pro Lys Ser Cys Asp Lys Thr His Thr Cys
                325                 330                 335

Pro Pro Cys Pro Ala Pro Glu Leu Leu Gly Gly Pro Ser Val Phe Leu
                340                 345                 350

Phe Pro Pro Lys Pro Lys Asp Thr Leu Met Ile Ser Arg Thr Pro Glu
            355                 360                 365

Val Thr Cys Val Val Val Asp Val Ser His Glu Asp Pro Glu Val Lys
        370                 375                 380

Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
                405                 410                 415

Thr Val Leu His Gln Asp Trp Leu Asn Gly Lys Glu Tyr Lys Cys Lys
                420                 425                 430

Val Ser Asn Lys Ala Leu Pro Ala Pro Ile Glu Lys Thr Ile Ser Lys
            435                 440                 445

Ala Lys Gly Gln Pro Arg Glu Pro Gln Val Tyr Thr Leu Pro Pro Ser
        450                 455                 460

Arg Asp Glu Leu Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
530                 535                 540

His Tyr Thr Gln Lys Ser Leu Ser Leu Ser Pro Gly Lys
545                 550                 555

<210> SEQ ID NO 7
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgaagtggg tgaccttcat cagcctgctg ttcctgttct ccagcgccta ctccatcccc    60
```

```
cccatgtgc aaaagagcgt gaacaacgat atgatcgtga ccgacaacaa cggcgccgtg      120
aagtttcccc agctctgcaa gttctgcgat gtcaggttca gcacctgcga taatcagaag      180
tcctgcatgt ccaactgcag catcacctcc atctgcgaga agccccaaga agtgtgcgtg      240
gccgtgtggc ggaaaaatga cgagaacatc accctggaga ccgtgtgtca cgaccccaag      300
ctcccttatc acgacttcat tctggaggac gctgcctccc ccaaatgcat catgaaggag      360
aagaagaagc ccggagagac cttctttatg tgttcctgta gcagcgacga gtgtaacgac      420
aacatcatct tcagcgaaga gtacaacacc agcaaccctg atggaggtgg cggatccgga      480
ggtggaggtt ctggtggagg tgggagtatt cctccccacg tgcagaagag cgtgaataat      540
gacatgatcg tgaccgataa caatggcgcc gtgaaatttc cccagctgtg caaattctgc      600
gatgtgaggt tttccacctg cgacaaccag aagtcctgta tgagcaactg ctccatcacc      660
tccatctgtg agaagcctca ggaggtgtgc gtggctgtct ggcggaagaa tgacgagaat      720
atcaccctgg aaaccgtctg ccacgatccc aagctgccct accacgattt catcctggaa      780
gacgccgcca gccctaagtg catcatgaaa gagaaaaaga gcctggcga gaccttttc       840
atgtgctcct gcagcagcga cgaatgcaac gacaatatca tctttagcga ggaatacaat      900
accagcaacc ccgacaactg ggttaacgta taagtgatt tgaaaaaat tgaagatctt       960
attcaatcta tgcatattga tgctacttta tatacggaaa gtgatgttca ccccagttgc     1020
aaagtaacag caatgaagtg ctttctcttg gagttacaag ttatttcact tgagtccgga     1080
gatgcaagta ttcatgatac agtagaaaat ctgatcatcc tagcaaacga cagtttgtct     1140
tctaatggga atgtaacaga atctggatgc aaagaatgtg aggaactgga ggaaaaaat      1200
attaaagaat ttttgcagag ttttgtacat attgtccaaa tgttcatcaa cacttct       1257
```

<210> SEQ ID NO 8
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly

```
            145                 150                 155                 160
        Gly Gly Gly Ser Gly Gly Gly Ser Ile Pro Pro His Val Gln Lys
                        165                 170                 175

Ser Val Asn Asn Asp Met Ile Val Thr Asp Asn Gly Ala Val Lys
                        180                 185                 190

Phe Pro Gln Leu Cys Lys Phe Cys Asp Val Arg Phe Ser Thr Cys Asp
                        195                 200                 205

Asn Gln Lys Ser Cys Met Ser Asn Cys Ser Ile Thr Ser Ile Cys Glu
                        210                 215                 220

Lys Pro Gln Glu Val Cys Val Ala Val Trp Arg Lys Asn Asp Glu Asn
        225                 230                 235                 240

Ile Thr Leu Glu Thr Val Cys His Asp Pro Lys Leu Pro Tyr His Asp
                            245                 250                 255

Phe Ile Leu Glu Asp Ala Ala Ser Pro Lys Cys Ile Met Lys Glu Lys
                        260                 265                 270

Lys Lys Pro Gly Glu Thr Phe Phe Met Cys Ser Cys Ser Ser Asp Glu
                        275                 280                 285

Cys Asn Asp Asn Ile Ile Phe Ser Glu Glu Tyr Asn Thr Ser Asn Pro
                    290                 295                 300

Asp Asn Trp Val Asn Val Ile Ser Asp Leu Lys Lys Ile Glu Asp Leu
        305                 310                 315                 320

Ile Gln Ser Met His Ile Asp Ala Thr Leu Tyr Thr Glu Ser Asp Val
                        325                 330                 335

His Pro Ser Cys Lys Val Thr Ala Met Lys Cys Phe Leu Leu Glu Leu
                        340                 345                 350

Gln Val Ile Ser Leu Glu Ser Gly Asp Ala Ser Ile His Asp Thr Val
                        355                 360                 365

Glu Asn Leu Ile Ile Leu Ala Asn Asp Ser Leu Ser Ser Asn Gly Asn
                    370                 375                 380

Val Thr Glu Ser Gly Cys Lys Glu Cys Glu Glu Leu Glu Glu Lys Asn
        385                 390                 395                 400

Ile Lys Glu Phe Leu Gln Ser Phe Val His Ile Val Gln Met Phe Ile
                        405                 410                 415

Asn Thr Ser

<210> SEQ ID NO 9
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgaagtggg tgaccttcat cagcctgctg ttcctgttct ccagcgccta ctccaactgg      60
gttaacgtaa taagtgattt gaaaaaaatt gaagatctta ttcaatctat gcatattgat     120
gctactttat atacggaaag tgatgttcac cccagttgca agtaacagc aatgaagtgc      180 tttctcttgg agttacaagt tatttcactt gagtccggag atgcaagtat tcatgataca     240
gtagaaaatc tgatcatcct agcaaacgac agtttgtctt ctaatgggaa tgtaacagaa     300
tctggatgca agaatgtga ggaactggag gaaaaaaata ttaagaatt tttgcagagt      360 tttgtacata ttgtccaaat gttcatcaac acttct                              396

<210> SEQ ID NO 10
```

<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Trp Val Thr Phe Ile Ser Leu Leu Phe Leu Phe Ser Ser Ala
1               5                   10                  15

Tyr Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80

Val Glu Asn Leu Ile Ile Leu Ala Asn Asp Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser
    130

<210> SEQ ID NO 11
<211> LENGTH: 2079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgaagtggg tgaccttcat cagcctgctg ttcctgttct ccagcgccta ctccaacatc      60
cagatgaccc agtcccctag ctccgtgtcc gcctccgtgg gagatcgggt gaccatcacc     120
tgtagggcct cccaggacat ctccaggtgg ctggcctggt accagcagaa gcccggcaag     180
gcccccaagc tgctgatcta cgccgcctcc tccctgcagt ccggagtgcc tagcaggttc     240
tccggctccg gatccggcac agacttcgcc ctgaccatct cctccctgca gcccgaggac     300
ttcgccacct actactgcca gcaggccgac tccaggttct ccatcacctt cggccagggc     360
accaggctgg agatcaagag gggaggtggc ggatccggag gtggaggttc tggtggaggt     420
gggagtgagg tgcagctggt gcagtccgga ggagactggt gcagcctggc ggatccctg     480 aggctgtcct gtgccgcttc cggcttcacc ttcagctcct actccatgaa ctgggtgagg     540
caggcccctg gaaagggcct ggagtgggtg tcctacatct ccagctcctc ctccaccatc     600
cagtacgccg actccgtgaa gggcaggttc accatctcca gggacaacgc caagaactcc     660
ctgtacctgc agatgaacag cctgagggac gaggacaccg ccgtgtacta ctgcgccagg     720
ggcgactatt actacggcat ggacgtgtgg ggccagggaa ccaccgtgac cgtgtcctcc     780
atcacgtgtc ctcctcctat gtccgtggaa cacgcagaca tctgggtcaa gagctacagc     840
ttgtactcca gggagcggta catttgtaac tctggtttca gcgtaaagc cggcacgtcc     900 agcctgacgg agtgcgtgtt gaacaaggcc acgaatgtcg cccactggac aaccccagt     960

-continued

```
ctcaaatgca ttagagagcc gaaatcttgt gacaaaactc acacatgccc accgtgccca    1020
gcacctgaac tcctgggggg accgtcagtc ttcctcttcc ccccaaaacc caaggacacc    1080
ctcatgatct cccggacccc tgaggtcaca tgcgtggtgg tggacgtgag ccacgaagac    1140
cctgaggtca agttcaactg gtacgtggac ggcgtggagg tgcataatgc caagacaaag    1200
ccgcgggagg agcagtacaa cagcacgtac cgtgtggtca gcgtcctcac cgtcctgcac    1260
caggactggc tgaatggcaa ggagtacaag tgcaaggtct ccaacaaagc cctcccagcc    1320
cccatcgaga aaaccatctc caaagccaaa gggcagcccc gagaaccaca ggtgtacacc    1380
ctgcccccat cccgggatga gctgaccaag aaccaggtca gcctgacctg cctggtcaaa    1440
ggcttctatc ccagcgacat cgccgtggag tgggagagca atgggcagcc ggagaacaac    1500
tacaagacca cgcctcccgt gctggactcc gacggctcct tcttcctcta cagcaagctc    1560
accgtggaca agagcaggtg gcagcagggg aacgtcttct catgctccgt gatgcatgag    1620
gctctgcaca accactacac gcagaagagc ctctccctgt ctcctggtaa atcccccccc    1680
cacgtgcaga agtccgttaa caacgacatg atcgtgaccg acaacaacgg cgccgtgaag    1740
ttcccccagc tgtgcaagtt ctgcgacgtg aggttctcca cctgcgacaa ccagaagtcc    1800
tgcatgtcca actgctccat cacctccatc tgcgagaagc tcaggaggt gtgcgtggct    1860 gtgtggcgga agaacgacga gaacatcacc ctggagaccg tgtgccacga ccccaagctg    1920
ccctaccacg acttcatcct ggaggacgcc gcctccccca gtgcatcat gaaggagaag    1980 aagaagcccg gcgagacctt ctttatgtgc tcctgctcca gcgacgagtg caacgacaac    2040
atcatcttct ccgaggagta caacacctcc aaccccgac                           2079
```

<210> SEQ ID NO 12
<211> LENGTH: 693
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ser Val Ser Ala Ser
            20                  25                  30

Val Gly Asp Arg Val Thr Ile Thr Cys Arg Ala Ser Gln Asp Ile Ser
        35                  40                  45

Arg Trp Leu Ala Trp Tyr Gln Gln Lys Pro Gly Lys Ala Pro Lys Leu
    50                  55                  60

Leu Ile Tyr Ala Ala Ser Ser Leu Gln Ser Gly Val Pro Ser Arg Phe
65                  70                  75                  80

Ser Gly Ser Gly Ser Gly Thr Asp Phe Ala Leu Thr Ile Ser Ser Leu
                85                  90                  95

Gln Pro Glu Asp Phe Ala Thr Tyr Tyr Cys Gln Gln Ala Asp Ser Arg
            100                 105                 110

Phe Ser Ile Thr Phe Gly Gln Gly Thr Arg Leu Glu Ile Lys Arg Gly
        115                 120                 125

Gly Gly Gly Ser Gly Gly Gly Gly Ser Gly Gly Gly Gly Ser Glu Val
    130                 135                 140

Gln Leu Val Gln Ser Gly Gly Gly Leu Val Gln Pro Gly Gly Ser Leu
145                 150                 155                 160
```

-continued

```
Arg Leu Ser Cys Ala Ala Ser Gly Phe Thr Phe Ser Ser Tyr Ser Met
                165                 170                 175
Asn Trp Val Arg Gln Ala Pro Gly Lys Gly Leu Glu Trp Val Ser Tyr
            180                 185                 190
Ile Ser Ser Ser Ser Ser Thr Ile Gln Tyr Ala Asp Ser Val Lys Gly
        195                 200                 205
Arg Phe Thr Ile Ser Arg Asp Asn Ala Lys Asn Ser Leu Tyr Leu Gln
    210                 215                 220
Met Asn Ser Leu Arg Asp Glu Asp Thr Ala Val Tyr Tyr Cys Ala Arg
225                 230                 235                 240
Gly Asp Tyr Tyr Tyr Gly Met Asp Val Trp Gly Gln Gly Thr Thr Val
                245                 250                 255
Thr Val Ser Ser Ile Thr Cys Pro Pro Pro Met Ser Val Glu His Ala
            260                 265                 270
Asp Ile Trp Val Lys Ser Tyr Ser Leu Tyr Ser Arg Glu Arg Tyr Ile
        275                 280                 285
Cys Asn Ser Gly Phe Lys Arg Lys Ala Gly Thr Ser Ser Leu Thr Glu
    290                 295                 300
Cys Val Leu Asn Lys Ala Thr Asn Val Ala His Trp Thr Thr Pro Ser
305                 310                 315                 320
Leu Lys Cys Ile Arg Glu Pro Lys Ser Cys Asp Lys Thr His Thr Cys
                325                 330                 335
Pro Pro Cys Pro Ala Pro Glu Leu Leu Gly Gly Pro Ser Val Phe Leu
            340                 345                 350
Phe Pro Pro Lys Pro Lys Asp Thr Leu Met Ile Ser Arg Thr Pro Glu
        355                 360                 365
Val Thr Cys Val Val Val Asp Val Ser His Glu Asp Pro Glu Val Lys
    370                 375                 380
Phe Asn Trp Tyr Val Asp Gly Val Glu Val His Asn Ala Lys Thr Lys
385                 390                 395                 400
Pro Arg Glu Glu Gln Tyr Asn Ser Thr Tyr Arg Val Val Ser Val Leu
                405                 410                 415
Thr Val Leu His Gln Asp Trp Leu Asn Gly Lys Glu Tyr Lys Cys Lys
            420                 425                 430
Val Ser Asn Lys Ala Leu Pro Ala Pro Ile Glu Lys Thr Ile Ser Lys
        435                 440                 445
Ala Lys Gly Gln Pro Arg Glu Pro Gln Val Tyr Thr Leu Pro Pro Ser
    450                 455                 460
Arg Asp Glu Leu Thr Lys Asn Gln Val Ser Leu Thr Cys Leu Val Lys
465                 470                 475                 480
Gly Phe Tyr Pro Ser Asp Ile Ala Val Glu Trp Glu Ser Asn Gly Gln
                485                 490                 495
Pro Glu Asn Asn Tyr Lys Thr Thr Pro Pro Val Leu Asp Ser Asp Gly
            500                 505                 510
Ser Phe Phe Leu Tyr Ser Lys Leu Thr Val Asp Lys Ser Arg Trp Gln
        515                 520                 525
Gln Gly Asn Val Phe Ser Cys Ser Val Met His Glu Ala Leu His Asn
    530                 535                 540
His Tyr Thr Gln Lys Ser Leu Ser Leu Ser Pro Gly Lys Ile Pro Pro
545                 550                 555                 560
His Val Gln Lys Ser Val Asn Asn Asp Met Ile Val Thr Asp Asn Asn
                565                 570                 575
Gly Ala Val Lys Phe Pro Gln Leu Cys Lys Phe Cys Asp Val Arg Phe
```

|   |   |   | 580 |   |   |   | 585 |   |   |   | 590 |   |   |
|---|---|---|---|---|---|---|---|---|---|---|---|---|---|
| Ser | Thr | Cys | Asp | Asn | Gln | Lys | Ser | Cys | Met | Ser | Asn | Cys | Ser | Ile | Thr |

Ser Thr Cys Asp Asn Gln Lys Ser Cys Met Ser Asn Cys Ser Ile Thr
                    595                 600                 605

Ser Ile Cys Glu Lys Pro Gln Glu Val Cys Val Ala Val Trp Arg Lys
        610                 615                 620

Asn Asp Glu Asn Ile Thr Leu Glu Thr Val Cys His Asp Pro Lys Leu
625                 630                 635                 640

Pro Tyr His Asp Phe Ile Leu Glu Asp Ala Ala Ser Pro Lys Cys Ile
                645                 650                 655

Met Lys Glu Lys Lys Lys Pro Gly Glu Thr Phe Phe Met Cys Ser Cys
        660                 665                 670

Ser Ser Asp Glu Cys Asn Asp Asn Ile Ile Phe Ser Glu Glu Tyr Asn
            675                 680                 685

Thr Ser Asn Pro Asp
        690

```
<210> SEQ ID NO 13
<211> LENGTH: 2142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
```

| | | | | |
|---|---|---|---|---|
| atgaagtggg | tgaccttcat | cagcctgctg | ttcctgttct | ccagcgccta ctccaacatc | 60 |
| cagatgaccc | agtccctag | ctccgtgtcc | gcctccgtgg | gagatcgggt gaccatcacc | 120 |
| tgtagggcct | cccaggacat | tccaggtgg | ctggcctggt | accagcagaa gcccggcaag | 180 |
| gcccccaagc | tgctgatcta | cgccgcctcc | tccctgcagt | ccggagtgcc tagcaggttc | 240 |
| tccggctccg | gatccggcac | agacttcgcc | ctgaccatct | cctccctgca gcccgaggac | 300 |
| ttcgccacct | actactgcca | gcaggccgac | tccaggttct | ccatcacctt cggccagggc | 360 |
| accaggctgg | agatcaagag | ggaggtggc | ggatccggag | gtggaggttc tggtggaggt | 420 |
| gggagtgagg | tgcagctggt | gcagtccgga | ggagactgg | tgcagcctgg cggatccctg | 480 |
| aggctgtcct | gtgccgcttc | cggcttcacc | ttcagctcct | actccatgaa ctgggtgagg | 540 |
| caggcccctg | gaaagggcct | ggagtgggtg | tcctacatct | ccagctcctc ctccaccatc | 600 |
| cagtacgccg | actccgtgaa | gggcaggttc | accatctcca | gggacaacgc caagaactcc | 660 |
| ctgtacctgc | agatgaacag | cctgagggac | gaggacaccg | ccgtgtacta ctgcgccagg | 720 |
| ggcgactatt | actacggcat | ggacgtgtgg | ggccagggaa | ccaccgtgac cgtgtcctcc | 780 |
| atcacgtgtc | tcctcctat | gtccgtgaaa | cacgcagaca | tctgggtcaa gagctacagc | 840 |
| ttgtactcca | gggagcggta | catttgtaac | tctggtttca | agcgtaaagc cggcacgtcc | 900 |
| agcctgacgg | agtgcgtgtt | gaacaaggcc | acgaatgtcg | cccactggac aaccccagt | 960 |
| ctcaaatgca | ttagagagcc | gaaatcttgt | gacaaaactc | acacatgccc accgtgccca | 1020 |
| gcacctgaac | tcctgggggg | accgtcagtc | ttcctcttcc | ccccaaaacc caaggacacc | 1080 |
| ctcatgatct | cccggacccc | tgaggtcaca | tgcgtggtgg | tggacgtgag ccacgaagac | 1140 |
| cctgaggtca | agttcaactg | gtacgtggac | ggcgtggagg | tgcataatgc caagacaaag | 1200 |
| ccgcgggagg | agcagtacaa | cagcacgtac | cgtgtggtca | gcgtcctcac cgtcctgcac | 1260 |
| caggactggc | tgaatggcaa | ggagtacaag | tgcaaggtct | ccaacaaagc cctcccagcc | 1320 |
| cccatcgaga | aaaccatctc | caaagccaaa | gggcagcccc | gagaaccaca ggtgtacacc | 1380 |

-continued

```
ctgcccccat cccgggatga gctgaccaag aaccaggtca gcctgacctg cctggtcaaa    1440
ggcttctatc ccagcgacat cgccgtggag tgggagagca atgggcagcc ggagaacaac    1500
tacaagacca cgcctcccgt gctggactcc gacggctcct tcttcctcta cagcaagctc    1560
accgtggaca gagcaggtg gcagcagggg aacgtcttct catgctccgt gatgcatgag    1620
gctctgcaca accactacac gcagaagagc ctctccctgt ctcctggtaa aggaggaggt    1680
ggctccggag gcgtggctc cggtggaggt ggctccggag gtggcggttc cggtatcccc    1740
ccccacgtgc agaagtccgt taacaacgac atgatcgtga ccgacaacaa cggcgccgtg    1800
aagttccccc agctgtgcaa gttctgcgac gtgaggttct ccacctgcga caaccagaag    1860
tcctgcatgt ccaactgctc catcacctcc atctgcgaga agcctcagga ggtgtgcgtg    1920
gctgtgtggc ggaagaacga cgagaacatc accctggaga ccgtgtgcca cgaccccaag    1980 ctgcccctacc acgacttcat cctggaggac gccgcctccc ccaagtgcat catgaaggag    2040
aagaagaagc ccggcgagac cttctttatg tgctcctgct ccagcgacga gtgcaacgac    2100
aacatcatct tctccgagga gtacaacacc tccaaccccg ac                     2142
```

<210> SEQ ID NO 14
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ser Val Ser Ala Ser
                20                  25                  30

Val Gly Asp Arg Val Thr Ile Thr Cys Arg Ala Ser Gln Asp Ile Ser
            35                  40                  45

Arg Trp Leu Ala Trp Tyr Gln Gln Lys Pro Gly Lys Ala Pro Lys Leu
        50                  55                  60

Leu Ile Tyr Ala Ala Ser Ser Leu Gln Ser Gly Val Pro Ser Arg Phe
65                  70                  75                  80

Ser Gly Ser Gly Ser Gly Thr Asp Phe Ala Leu Thr Ile Ser Ser Leu
                85                  90                  95

Gln Pro Glu Asp Phe Ala Thr Tyr Tyr Cys Gln Gln Ala Asp Ser Arg
            100                 105                 110

Phe Ser Ile Thr Phe Gly Gln Gly Thr Arg Leu Glu Ile Lys Arg Gly
        115                 120                 125

Gly Gly Gly Ser Gly Gly Gly Gly Ser Gly Gly Gly Gly Ser Glu Val
    130                 135                 140

Gln Leu Val Gln Ser Gly Gly Gly Leu Val Gln Pro Gly Gly Ser Leu
145                 150                 155                 160

Arg Leu Ser Cys Ala Ala Ser Gly Phe Thr Phe Ser Ser Tyr Ser Met
                165                 170                 175

Asn Trp Val Arg Gln Ala Pro Gly Lys Gly Leu Glu Trp Val Ser Tyr
            180                 185                 190

Ile Ser Ser Ser Ser Ser Thr Ile Gln Tyr Ala Asp Ser Val Lys Gly
        195                 200                 205

Arg Phe Thr Ile Ser Arg Asp Asn Ala Lys Asn Ser Leu Tyr Leu Gln
    210                 215                 220
```

```
Met Asn Ser Leu Arg Asp Glu Asp Thr Ala Val Tyr Tyr Cys Ala Arg
225                 230                 235                 240

Gly Asp Tyr Tyr Tyr Gly Met Asp Val Trp Gly Gln Gly Thr Thr Val
            245                 250                 255

Thr Val Ser Ser Ile Thr Cys Pro Pro Pro Met Ser Val Glu His Ala
        260                 265                 270

Asp Ile Trp Val Lys Ser Tyr Ser Leu Tyr Ser Arg Glu Arg Tyr Ile
        275                 280                 285

Cys Asn Ser Gly Phe Lys Arg Lys Ala Gly Thr Ser Ser Leu Thr Glu
290                 295                 300

Cys Val Leu Asn Lys Ala Thr Asn Val Ala His Trp Thr Thr Pro Ser
305                 310                 315                 320

Leu Lys Cys Ile Arg Glu Pro Lys Ser Cys Asp Lys Thr His Thr Cys
                325                 330                 335

Pro Pro Cys Pro Ala Pro Glu Leu Leu Gly Gly Pro Ser Val Phe Leu
            340                 345                 350

Phe Pro Pro Lys Pro Lys Asp Thr Leu Met Ile Ser Arg Thr Pro Glu
        355                 360                 365

Val Thr Cys Val Val Val Asp Val Ser His Glu Asp Pro Glu Val Lys
    370                 375                 380

Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
                405                 410                 415

Thr Val Leu His Gln Asp Trp Leu Asn Gly Lys Glu Tyr Lys Cys Lys
            420                 425                 430

Val Ser Asn Lys Ala Leu Pro Ala Pro Ile Glu Lys Thr Ile Ser Lys
        435                 440                 445

Ala Lys Gly Gln Pro Arg Glu Pro Gln Val Tyr Thr Leu Pro Pro Ser
    450                 455                 460

Arg Asp Glu Leu Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
    530                 535                 540

His Tyr Thr Gln Lys Ser Leu Ser Leu Ser Pro Gly Lys Gly Gly Gly
545                 550                 555                 560

Gly Ser Gly Gly Gly Gly Ser Gly Gly Gly Gly Ser Gly Gly Gly Gly
                565                 570                 575

Ser Gly Ile Pro Pro His Val Gln Lys Ser Val Asn Asn Asp Met Ile
            580                 585                 590

Val Thr Asp Asn Asn Gly Ala Val Lys Phe Pro Gln Leu Cys Lys Phe
        595                 600                 605

Cys Asp Val Arg Phe Ser Thr Cys Asp Asn Gln Lys Ser Cys Met Ser
    610                 615                 620

Asn Cys Ser Ile Thr Ser Ile Cys Glu Lys Pro Gln Glu Val Cys Val
625                 630                 635                 640
```

| | | | | | | | | | | | |
|---|---|---|---|---|---|---|---|---|---|---|---|
|Ala|Val|Trp|Arg|Lys|Asn|Asp|Glu|Asn|Ile|Thr|Leu|Glu|Thr|Val|Cys|
| | | | |645| | | |650| | | |655| | | |

His Asp Pro Lys Leu Pro Tyr His Asp Phe Ile Leu Glu Asp Ala Ala
            660                 665                 670

Ser Pro Lys Cys Ile Met Lys Glu Lys Lys Pro Gly Glu Thr Phe
        675                 680                 685

Phe Met Cys Ser Cys Ser Ser Asp Glu Cys Asn Asp Asn Ile Ile Phe
    690                 695                 700

Ser Glu Glu Tyr Asn Thr Ser Asn Pro Asp
705                 710

<210> SEQ ID NO 15
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agcccaagga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga  gacctttttc     840 atgtgctcct gcagcagcga cgaatgcaac gacaatatca tctttagcga ggaatacaat     900
accagcaacc ccgacaactg ggtgaatgta taagtgatt  tgaaaaaaat tgaagatctt     960
attcaatcta tgcatattga tgctacttta tatacggaaa gtgatgttca ccccagttgc    1020
aaagtaacag caatgaagtg ctttctcttg gagttacaag ttatttcact tgagtccgga    1080
gatgcaagta ttcatgatac agtagaaaat ctgatcatcc tagcaaacga cagtttgtct    1140
tctaatggga atgtaacaga atctggatgc aaagaatgtg aggaactgga ggaaaaaat     1200 attaaagaat ttttgcagag ttttgtacat attgtccaaa tgttcatcaa cacttcttaa    1260

<210> SEQ ID NO 16
<211> LENGTH: 1161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgaagtggg tgaccttcat cagcctgctg ttcctgttct ccagcgccta ctccatcccc    60
ccccatgtgc aaaagagcgt gaacaacgat atgatcgtga ccgacaacaa cggcgccgtg   120
aagtttcccc agctctgcaa gttctgcgat gtcaggttca gcacctgcga taatcagaag   180
tcctgcatgt ccaactgcac gatcacctcc atctgcgaga agcccaaga agtgtgcgtg    240 gccgtgtggc ggaaaaatga cgagaacatc accctggaga ccgtgtgtca cgaccccaag   300
ctcccttatc acgacttcat tctggaggac gctgcctccc ccaaatgcat catgaaggag   360
aagaagaagc ccggagagac cttctttatg tgttcctgta gcagcgacga gtgtaacgac   420
aacatcatct tcagcgaaga gtacaacacc agcaaccctg atgagcccaa atcttgtgac   480
aaaactcaca catgcccacc gtgcccagca cctgaactcc tggggggacc gtcagtcttc   540
ctcttccccc caaaacccaa ggacaccctc atgatctccc ggacccctga ggtcacatgc   600
gtggtggtgg acgtgagcca cgaagaccct gaggtcaagt tcaactggta cgtggacggc   660
gtggaggtgc ataatgccaa gacaaagccg cgggaggagc agtacaacag cacgtaccgt   720
gtggtcagcg tcctcaccgt cctgcaccag gactggctga atggcaagga gtacaagtgc   780
aaggtctcca acaaagccct cccagccccc atcgagaaaa ccatctccaa agccaaaggg   840
cagccccgag aaccacaggt gtacaccctg cccccatccc gggatgagct gaccaagaac   900
caggtcagcc tgacctgcct ggtcaaaggc ttctatccca gcgacatcgc cgtggagtgg   960
gagagcaatg ggcagccgga gaacaactac aagaccacgc ctcccgtgct ggactccgac  1020
ggctccttct tcctctacag caagctcacc gtggacaaga gcaggtggca gcagggggaac 1080 gtcttctcat gctccgtgat gcatgaggct ctgcacaacc actacacgca gaagagcctc  1140
tccctgtctc cgggtaaata a                                             1161
```

<210> SEQ ID NO 17
<211> LENGTH: 1809
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atgaagtggg tgaccttcat cagcctgctg ttcctgttct ccagcgccta ctccatcccc    60
ccccatgtgc aaaagagcgt gaacaacgat atgatcgtga ccgacaacaa cggcgccgtg   120
aagtttcccc agctctgcaa gttctgcgat gtcaggttca gcacctgcga taatcagaag   180
tcctgcatgt ccaactgcac gatcacctcc atctgcgaga agcccaaga agtgtgcgtg    240 gccgtgtggc ggaaaaatga cgagaacatc accctggaga ccgtgtgtca cgaccccaag   300
ctcccttatc acgacttcat tctggaggac gctgcctccc ccaaatgcat catgaaggag   360
aagaagaagc ccggagagac cttctttatg tgttcctgta gcagcgacga gtgtaacgac   420
aacatcatct tcagcgaaga gtacaacacc agcaaccctg atggaggtgg cggatccgga   480
ggtggaggtt ctggtggagg tgggagtatt cctccccacg tgcagaagag cgtgaataat   540
gacatgatcg tgaccgataa caatggcgcc gtgaaatttc cccagctgtg caaattctgc   600
gatgtgaggt tttccacctg cgacaaccag aagtcctgta tgagcaactg cacaatcacc   660
tccatctgtg agaagcctca ggaggtgtgc gtggctgtct ggcggaagaa tgacgagaat   720
atcaccctgg aaaccgtctg ccacgatccc aagctgccct accacgattt catcctggaa   780
gacgccgcca gccctaagtg catcatgaaa gagaaaaaga gcctggcga gaccttttc     840
```

```
atgtgctcct gcagcagcga cgaatgcaac gacaatatca tctttagcga ggaatacaat      900
accagcaacc ccgacatcac gtgtcctcct cctatgtccg tggaacacgc agacatctgg      960
gtcaagagct acagcttgta ctccagggag cggtacattt gtaactctgg tttcaagcgt     1020
aaagccggca cgtccagcct gacggagtgc gtgttgaaca aggccacgaa tgtcgcccac     1080
tggacaaccc ccagtctcaa atgtattaga gagcccaaat cttgtgacaa aactcacaca     1140
tgcccaccgt gcccagcacc tgaactcctg ggggaccgt cagtcttcct cttcccccca      1200
aaacccaagg acaccctcat gatctcccgg acccctgagg tcacatgcgt ggtggtggac     1260
gtgagccacg aagaccctga ggtcaagttc aactggtacg tggacggcgt ggaggtgcat     1320
aatgccaaga caaagccgcg ggaggagcag tacaacagca cgtaccgtgt ggtcagcgtc     1380
ctcaccgtcc tgcaccagga ctggctgaat ggcaaggagt acaagtgcaa ggtctccaac     1440
aaagccctcc cagcccccat cgagaaaacc atctccaaag ccaagggca gccccgagaa     1500
ccacaggtgt acaccctgcc cccatcccgg gatgagctga ccaagaacca ggtcagcctg     1560
acctgcctgg tcaaaggctt ctatcccagc gacatcgccg tggagtggga gagcaatggg     1620
cagccggaga caactacaa gaccacgcct cccgtgctgg actccgacgg ctccttcttc      1680
ctctacagca agctcaccgt ggacaagagc aggtggcagc aggggaacgt cttctcatgc     1740
tccgtgatgc atgaggctct gcacaaccac tacacgcaga agagcctctc cctgtctccg     1800
ggtaaataa                                                            1809

<210> SEQ ID NO 18
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
aactgggtga atgtaataag tgatttgaaa aaaattgaag atcttatcca gtccatgcac       60
atcgacgcca ccctgtacac cgagagcgac gtgcacccct cctgcaaggt gaccgccatg      120
aagtgcttcc tgctggagct gcaggtgatc tccctggagt ccggcgacgc ctccatccac      180
gacaccgtgg agaacctgat catcctggcc aacgactccc tgtcctccaa cggcaacgtg      240
accgagtccg ctgcaagga gtgcgaggag ctggaggaga gaacatcaa ggagttcctg       300
cagtccttcg tgcacatcgt ccaaatgttc atcaacactt ct                        342

<210> SEQ ID NO 19
<211> LENGTH: 2148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atggaatgga gctgggtctt tctcttcttc ctgtcagtaa ccaccggtgt ccactccaac       60
atccagatga cccagtctcc atcttctgtg tctgcatctg taggagacag agtcaccatc      120
acttgtcggg cgagtcagga tattagccgc tggttagcct ggtatcagca gaaaccaggg     180
aaagccccta aactcctgat ctatgctgca tccagtttgc aaagtggggt cccatcgagg     240
ttcagcggca gtggatctgg gacagatttc gctctcacta tcagcagcct gcagcctgaa      300
gattttgcaa cttactattg tcaacaggct gacagtcgtt tctcgatcac cttcggccaa      360
```

```
gggacacgac tggagattaa acgaggaggt ggcggatccg gaggtggagg ttctggtgga    420
ggtgggagtg aggtgcagct ggtgcagtct ggggggaggct tggtacagcc tggggggtcc    480
ctgagactct cctgtgcagc ctctggattc accttcagta gctatagcat gaactgggtc    540
cgccaggctc cagggaaggg gctggagtgg gtttcataca ttagtagtag tagtagtacc    600
atacagtacg cagactctgt gaagggccga ttcaccatct ccagagacaa tgccaagaac    660
tcactgtatc tgcaaatgaa cagcctgaga cgaggaca  cggctgtgta ttactgtgcg    720 agagggact actactacgg tatggacgtc tggggccaag ggaccacggt caccgtgagc    780
tcaatcacgt gtcctcctcc tatgtccgtg aacacgcag acatctgggt caagagctac    840
agcttgtact ccagggagcg gtacatttgt aactctggtt tcaagcgtaa agccggcacg    900
tccagcctga cggagtgcgt gttgaacaag gccacgaatg tcgcccactg acaaccccc     960 agtctcaaat gcattagaga gccgaaatct tgtgacaaaa ctcacacatg cccaccgtgc   1020
ccagcacctg aactcctggg gggaccgtca gtcttcctct tccccccaaa acccaaggac   1080
accctcatga tctcccggac ccctgaggtc acatgcgtgg tggtggacgt gagccacgaa   1140
gaccctgagg tcaagttcaa ctggtacgtg gacggcgtgg aggtgcataa tgccaagaca   1200
aagccgcggg aggagcagta caacagcacg taccgtgtgg tcagcgtcct caccgtcctg   1260
caccaggact ggctgaatgg caaggagtac aagtgcaagg tctccaacaa agccctccca   1320
gcccccatcg agaaaaccat ctccaaagcc aaagggcagc cccgagaacc acaggtgtac   1380
accctgcccc catcccggga tgagctgacc aagaaccagg tcagcctgac ctgcctggtc   1440
aaaggcttct atcccagcga catcgccgtg gagtgggaga gcaatgggca gccggagaac   1500
aactacaaga ccacgcctcc cgtgctggac tccgacggct ccttcttcct ctacagcaag   1560
ctcaccgtgg acaagagcag gtggcagcag gggaacgtct tctcatgctc cgtgatgcat   1620
gaggctctgc acaaccacta cacgcagaag agcctctccc tgtctcctgg taaaggagga   1680
ggtggctccg gaggcggtgg ctccggtgga ggtggctccg gaggtggcgg ttccggtatc   1740
cccccccacg tgcagaagtc cgttaacaac gacatgatcg tgaccgacaa caacggcgcc   1800
gtgaagttcc cccagctgtg caagttctgc gacgtgaggt tctccacctg cgacaaccag   1860
aagtcctgca tgtccaactg cccaatcacc tccatctgcg agaagcctca ggaggtgtgc   1920
gtggctgtgt ggcggaagaa cgacgagaac atcaccctgg agaccgtgtg ccacgacccc   1980
aagctgccct accacgactt catcctggag gacgccgcct cccccaagtg catcatgaag   2040
gagaagaaga agccccggcga gaccttcttt atgtgctcct gctccagcga cgagtgcaac   2100
gacaacatca tcttctccga ggagtacaac acctccaacc ccgactga              2148
```

<210> SEQ ID NO 20
<211> LENGTH: 114
<212> TYPE: PRT
<213> ORGANISM: Homo sapiens

<400> SEQUENCE: 20

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu

```
                50                  55                  60
Asn Leu Ile Ile Leu Ala Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 21
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asn Trp Val Asn Val Ile Ser Asp Leu Lys Lys Ile Glu Asp Leu Ile
  1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
                 35                  40                  45

Val Ile Ser Leu Glu Ser Gly Asp Ala Ser Ile His Asp Thr Val Glu
             50                  55                  60

Asn Leu Ile Ile Leu Ala Asn Asp Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser Asn Ile Gln Met Thr Gln Ser Pro Ser Ser Val Ser Ala Ser
                115                 120                 125

Val Gly Asp Arg Val Thr Ile Thr Cys Arg Ala Ser Gln Asp Ile Ser
            130                 135                 140

Arg Trp Leu Ala Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Asp Phe Ala Leu Thr Ile Ser Ser Leu
                180                 185                 190

Gln Pro Glu Asp Phe Ala Thr Tyr Tyr Cys Gln Gln Ala Asp Ser Arg
                195                 200                 205

Phe Ser Ile Thr Phe Gly Gln Gly Thr Arg Leu Glu Ile Lys Arg Gly
            210                 215                 220

Gly Gly Gly Ser Gly Gly Gly Gly Ser Gly Gly Gly Gly Ser Glu Val
225                 230                 235                 240

Gln Leu Val Gln Ser Gly Gly Gly Leu Val Gln Pro Gly Gly Ser Leu
                245                 250                 255

Arg Leu Ser Cys Ala Ala Ser Gly Phe Thr Phe Ser Ser Tyr Ser Met
                260                 265                 270

Asn Trp Val Arg Gln Ala Pro Gly Lys Gly Leu Glu Trp Val Ser Tyr
                275                 280                 285

Ile Ser Ser Ser Ser Ser Thr Ile Gln Tyr Ala Asp Ser Val Lys Gly
```

```
                290             295             300
Arg Phe Thr Ile Ser Arg Asp Asn Ala Lys Asn Ser Leu Tyr Leu Gln
305                 310                 315                 320

Met Asn Ser Leu Arg Asp Glu Asp Thr Ala Val Tyr Tyr Cys Ala Arg
                325                 330                 335

Gly Asp Tyr Tyr Tyr Gly Met Asp Val Trp Gly Gln Gly Thr Thr Val
                340                 345                 350

Thr Val Ser Ser Ile Thr Cys Pro Pro Met Ser Val Glu His Ala
                355                 360                 365

Asp Ile Trp Val Lys Ser Tyr Ser Leu Tyr Ser Arg Glu Arg Tyr Ile
                370                 375                 380

Cys Asn Ser Gly Phe Lys Arg Lys Ala Gly Thr Ser Ser Leu Thr Glu
385                 390                 395                 400

Cys Val Leu Asn Lys Ala Thr Asn Val Ala His Trp Thr Thr Pro Ser
                405                 410                 415

Leu Lys Cys Ile Arg Glu Pro Lys Ser Cys Asp Lys Thr His Thr Cys
                420                 425                 430

Pro Pro Cys Pro Ala Pro Glu Leu Leu Gly Gly Pro Ser Val Phe Leu
                435                 440                 445

Phe Pro Pro Lys Pro Lys Asp Thr Leu Met Ile Ser Arg Thr Pro Glu
                450                 455                 460

Val Thr Cys Val Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Asn Ser Thr Tyr Arg Val Val Ser Val Leu
                500                 505                 510

Thr Val Leu His Gln Asp Trp Leu Asn Gly Lys Glu Tyr Lys Cys Lys
                515                 520                 525

Val Ser Asn Lys Ala Leu Pro Ala Pro Ile Glu Lys Thr Ile Ser Lys
                530                 535                 540

Ala Lys Gly Gln Pro Arg Glu Pro Gln Val Tyr Thr Leu Pro Pro Ser
545                 550                 555                 560

Arg Asp Glu Leu Thr Lys Asn Gln Val Ser Leu Thr Cys Leu Val Lys
                565                 570                 575

Gly Phe Tyr Pro Ser Asp Ile Ala Val Glu Trp Glu Ser Asn Gly Gln
                580                 585                 590

Pro Glu Asn Asn Tyr Lys Thr Thr Pro Pro Val Leu Asp Ser Asp Gly
                595                 600                 605

Ser Phe Phe Leu Tyr Ser Lys Leu Thr Val Asp Lys Ser Arg Trp Gln
                610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys Gly Gly Gly
                645                 650                 655

Gly Ser Gly Gly Gly Gly Ser Gly Gly Gly Gly Ser Gly Gly Gly Gly
                660                 665                 670

Ser Gly Ile Pro Pro His Val Gln Lys Ser Val Asn Asn Asp Met Ile
                675                 680                 685

Val Thr Asp Asn Asn Gly Ala Val Lys Phe Pro Gln Leu Cys Lys Phe
                690                 695                 700

Cys Asp Val Arg Phe Ser Thr Cys Asp Asn Gln Lys Ser Cys Met Gln
705                 710                 715                 720
```

```
Asn Cys Pro Ile Thr Ser Ile Cys Glu Lys Pro Gln Glu Val Cys Val
                725                 730                 735

Ala Val Trp Arg Lys Gln Asp Glu Asn Ile Thr Leu Glu Thr Val Cys
            740                 745                 750

His Asp Pro Lys Leu Pro Tyr His Asp Phe Ile Leu Glu Asp Ala Ala
        755                 760                 765

Ser Pro Lys Cys Ile Met Lys Glu Lys Lys Pro Gly Glu Thr Phe
770                 775                 780

Phe Met Cys Ser Cys Ser Ser Asp Glu Cys Asn Asp Asn Ile Ile Phe
785                 790                 795                 800

Ser Glu Glu Tyr Gln Thr Ser Asn Pro Asp
            805                 810

<210> SEQ ID NO 22
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Asn Ile Gln Met Thr Gln Ser Pro Ser Ser Val Ser Ala Ser
        115                 120                 125

Val Gly Asp Arg Val Thr Ile Thr Cys Arg Ala Ser Gln Asp Ile Ser
    130                 135                 140

Arg Trp Leu Ala Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Asp Phe Ala Leu Thr Ile Ser Ser Leu
            180                 185                 190

Gln Pro Glu Asp Phe Ala Thr Tyr Tyr Cys Gln Gln Ala Asp Ser Arg
        195                 200                 205

Phe Ser Ile Thr Phe Gly Gln Gly Thr Arg Leu Glu Ile Lys Arg Gly
    210                 215                 220

Gly Gly Gly Ser Gly Gly Gly Gly Ser Gly Gly Gly Gly Ser Glu Val
225                 230                 235                 240

Gln Leu Val Gln Ser Gly Gly Gly Leu Val Gln Pro Gly Gly Ser Leu
                245                 250                 255

Arg Leu Ser Cys Ala Ala Ser Gly Phe Thr Phe Ser Ser Tyr Ser Met
```

```
              260                 265                 270
Asn Trp Val Arg Gln Ala Pro Gly Lys Gly Leu Glu Trp Val Ser Tyr
            275                 280                 285
Ile Ser Ser Ser Ser Thr Ile Gln Tyr Ala Asp Ser Val Lys Gly
            290                 295             300
Arg Phe Thr Ile Ser Arg Asp Asn Ala Lys Asn Ser Leu Tyr Leu Gln
305                 310                 315                 320
Met Asn Ser Leu Arg Asp Glu Asp Thr Ala Val Tyr Tyr Cys Ala Arg
                325                 330                 335
Gly Asp Tyr Tyr Tyr Gly Met Asp Val Trp Gly Gln Gly Thr Thr Val
            340                 345                 350
Thr Val Ser Ser Ile Thr Cys Pro Pro Pro Met Ser Val Glu His Ala
            355                 360                 365
Asp Ile Trp Val Lys Ser Tyr Ser Leu Tyr Ser Arg Glu Arg Tyr Ile
            370                 375                 380
Cys Asn Ser Gly Phe Lys Arg Lys Ala Gly Thr Ser Ser Leu Thr Glu
385                 390                 395                 400
Cys Val Leu Asn Lys Ala Thr Asn Val Ala His Trp Thr Thr Pro Ser
                405                 410                 415
Leu Lys Cys Ile Arg Glu Pro Lys Ser Cys Asp Lys Thr His Thr Cys
                420                 425                 430
Pro Pro Cys Pro Ala Pro Glu Leu Leu Gly Gly Pro Ser Val Phe Leu
            435                 440                 445
Phe Pro Pro Lys Pro Lys Asp Thr Leu Met Ile Ser Arg Thr Pro Glu
            450                 455                 460
Val Thr Cys Val Val Val Asp Val Ser His Glu Asp Pro Glu Val Lys
465                 470                 475                 480
Phe Asn Trp Tyr Val Asp Gly Val Glu Val His Asn Ala Lys Thr Lys
                485                 490                 495
Pro Arg Glu Glu Gln Tyr Asn Ser Thr Tyr Arg Val Val Ser Val Leu
                500                 505                 510
Thr Val Leu His Gln Asp Trp Leu Asn Gly Lys Glu Tyr Lys Cys Lys
            515                 520                 525
Val Ser Asn Lys Ala Leu Pro Ala Pro Ile Glu Lys Thr Ile Ser Lys
            530                 535                 540
Ala Lys Gly Gln Pro Arg Glu Pro Gln Val Tyr Thr Leu Pro Pro Ser
545                 550                 555                 560
Arg Asp Glu Leu Thr Lys Asn Gln Val Ser Leu Thr Cys Leu Val Lys
                565                 570                 575
Gly Phe Tyr Pro Ser Asp Ile Ala Val Glu Trp Glu Ser Asn Gly Gln
            580                 585                 590
Pro Glu Asn Asn Tyr Lys Thr Thr Pro Pro Val Leu Asp Ser Asp Gly
            595                 600                 605
Ser Phe Phe Leu Tyr Ser Lys Leu Thr Val Asp Lys Ser Arg Trp Gln
            610                 615                 620
Gln Gly Asn Val Phe Ser Cys Ser Val Met His Glu Ala Leu His Asn
625                 630                 635                 640
His Tyr Thr Gln Lys Ser Leu Ser Leu Ser Pro Gly Lys Gly Gly Gly
                645                 650                 655
Gly Ser Gly Gly Gly Gly Ser Gly Gly Gly Gly Ser Gly Gly Gly Gly
            660                 665                 670
Ser Gly Ile Pro Pro His Val Gln Lys Ser Val Asn Asn Asp Met Ile
            675                 680                 685
```

```
Val Thr Asp Asn Asn Gly Ala Val Lys Phe Pro Gln Leu Cys Lys Phe
    690                 695                 700

Cys Asp Val Arg Phe Ser Thr Cys Asp Asn Gln Lys Ser Cys Met Gln
705                 710                 715                 720

Asn Cys Pro Ile Thr Ser Ile Cys Glu Lys Pro Gln Glu Val Cys Val
                725                 730                 735

Ala Val Trp Arg Lys Gln Asp Glu Asn Ile Thr Leu Glu Thr Val Cys
            740                 745                 750

His Asp Pro Lys Leu Pro Tyr His Asp Phe Ile Leu Glu Asp Ala Ala
        755                 760                 765

Ser Pro Lys Cys Ile Met Lys Glu Lys Lys Pro Gly Glu Thr Phe
770                 775                 780

Phe Met Cys Ser Cys Ser Ser Asp Glu Cys Asn Asp Asn Ile Ile Phe
785                 790                 795                 800

Ser Glu Glu Tyr Gln Thr Ser Asn Pro Asp
                805                 810

<210> SEQ ID NO 23
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Asn Ile Gln Met Thr Gln Ser Pro Ser Ser Val Ser Ala Ser
        115                 120                 125

Val Gly Asp Arg Val Thr Ile Thr Cys Arg Ala Ser Gln Asp Ile Ser
    130                 135                 140

Arg Trp Leu Ala Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Asp Phe Ala Leu Thr Ile Ser Ser Leu
            180                 185                 190

Gln Pro Glu Asp Phe Ala Thr Tyr Tyr Cys Gln Gln Ala Asp Ser Arg
        195                 200                 205

Phe Ser Ile Thr Phe Gly Gln Gly Thr Arg Leu Glu Ile Lys Arg Gly
    210                 215                 220

Gly Gly Gly Ser Gly Gly Gly Gly Ser Gly Gly Gly Gly Ser Glu Val
```

-continued

```
            225                 230                 235                 240
        Gln Leu Val Gln Ser Gly Gly Leu Val Gln Pro Gly Gly Ser Leu
                            245                 250                 255
        Arg Leu Ser Cys Ala Ala Ser Gly Phe Thr Phe Ser Ser Tyr Ser Met
                        260                 265                 270
        Asn Trp Val Arg Gln Ala Pro Gly Lys Gly Leu Glu Trp Val Ser Tyr
                    275                 280                 285
        Ile Ser Ser Ser Ser Ser Thr Ile Gln Tyr Ala Asp Ser Val Lys Gly
                290                 295                 300
        Arg Phe Thr Ile Ser Arg Asp Asn Ala Lys Asn Ser Leu Tyr Leu Gln
        305                 310                 315                 320
        Met Asn Ser Leu Arg Asp Glu Asp Thr Ala Val Tyr Tyr Cys Ala Arg
                        325                 330                 335
        Gly Asp Tyr Tyr Tyr Gly Met Asp Val Trp Gly Gln Gly Thr Thr Val
                        340                 345                 350
        Thr Val Ser Ser Ile Thr Cys Pro Pro Pro Met Ser Val Glu His Ala
                    355                 360                 365
        Asp Ile Trp Val Lys Ser Tyr Ser Leu Tyr Ser Arg Glu Arg Tyr Ile
                370                 375                 380
        Cys Asn Ser Gly Phe Lys Arg Lys Ala Gly Thr Ser Ser Leu Thr Glu
        385                 390                 395                 400
        Cys Val Leu Asn Lys Ala Thr Asn Val Ala His Trp Thr Thr Pro Ser
                        405                 410                 415
        Leu Lys Cys Ile Arg Glu Pro Lys Ser Ser Asp Lys Thr His Thr Cys
                    420                 425                 430
        Pro Pro Cys Pro Ala Pro Glu Leu Leu Gly Gly Pro Ser Val Phe Leu
                        435                 440                 445
        Phe Pro Pro Lys Pro Lys Asp Thr Leu Met Ile Ser Arg Thr Pro Glu
                    450                 455                 460
        Val Thr Cys Val Val Val Asp Val Ser His Glu Asp Pro Glu Val Lys
        465                 470                 475                 480
        Phe Asn Trp Tyr Val Asp Gly Val Glu Val His Asn Ala Lys Thr Lys
                        485                 490                 495
        Pro Arg Glu Glu Gln Tyr Asn Ser Thr Tyr Arg Val Val Ser Val Leu
                    500                 505                 510
        Thr Val Leu His Gln Asp Trp Leu Asn Gly Lys Glu Tyr Lys Cys Lys
                    515                 520                 525
        Val Ser Asn Lys Ala Leu Pro Ala Pro Ile Glu Lys Thr Ile Ser Lys
        530                 535                 540
        Ala Lys Gly Gln Pro Arg Glu Pro Gln Val Tyr Thr Leu Pro Pro Ser
        545                 550                 555                 560
        Arg Asp Glu Leu Thr Lys Asn Gln Val Ser Leu Thr Cys Leu Val Lys
                        565                 570                 575
        Gly Phe Tyr Pro Ser Asp Ile Ala Val Glu Trp Glu Ser Asn Gly Gln
                    580                 585                 590
        Pro Glu Asn Asn Tyr Lys Thr Thr Pro Pro Val Leu Asp Ser Asp Gly
                    595                 600                 605
        Ser Phe Phe Leu Tyr Ser Lys Leu Thr Val Asp Lys Ser Arg Trp Gln
                610                 615                 620
        Gln Gly Asn Val Phe Ser Cys Ser Val Met His Glu Ala Leu His Asn
        625                 630                 635                 640
        His Tyr Thr Gln Lys Ser Leu Ser Leu Ser Pro Gly Lys Gly Gly Gly
                        645                 650                 655
```

```
Gly Ser Gly Gly Gly Ser Gly Gly Gly Ser Gly Gly Gly
            660                 665                 670

Ser Gly Ile Pro Pro His Val Gln Lys Ser Val Asn Asp Met Ile
        675                 680                 685

Val Thr Asp Asn Asn Gly Ala Val Lys Phe Pro Gln Leu Cys Lys Phe
690                 695                 700

Cys Asp Val Arg Phe Ser Thr Cys Asp Asn Gln Lys Ser Cys Met Gln
705                 710                 715                 720

Asn Cys Pro Ile Thr Ser Ile Cys Glu Lys Pro Gln Glu Val Cys Val
                725                 730                 735

Ala Val Trp Arg Lys Gln Asp Glu Asn Ile Thr Leu Glu Thr Val Cys
            740                 745                 750

His Asp Pro Lys Leu Pro Tyr His Asp Phe Ile Leu Glu Asp Ala Ala
            755                 760                 765

Ser Pro Lys Cys Ile Met Lys Glu Lys Lys Pro Gly Glu Thr Phe
        770                 775                 780

Phe Met Cys Ser Cys Ser Ser Asp Glu Cys Asn Asp Asn Ile Ile Phe
785                 790                 795                 800

Ser Glu Glu Tyr Gln Thr Ser Asn Pro Asp
            805                 810

<210> SEQ ID NO 24
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Asn Ile Gln Met Thr Gln Ser Pro Ser Ser Val Ser Ala Ser
        115                 120                 125

Val Gly Asp Arg Val Thr Ile Thr Cys Arg Ala Ser Gln Asp Ile Ser
    130                 135                 140

Arg Trp Leu Ala Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Asp Phe Ala Leu Thr Ile Ser Ser Leu
            180                 185                 190

Gln Pro Glu Asp Phe Ala Thr Tyr Tyr Cys Gln Gln Ala Asp Ser Arg
```

```
            195                 200                 205
Phe Ser Ile Thr Phe Gly Gln Gly Thr Arg Leu Glu Ile Lys Arg Gly
210                 215                 220

Gly Gly Gly Ser Gly Gly Gly Ser Gly Gly Gly Ser Glu Val
225                 230                 235                 240

Gln Leu Val Gln Ser Gly Gly Leu Val Gln Pro Gly Gly Ser Leu
                245                 250                 255

Arg Leu Ser Cys Ala Ala Ser Gly Phe Thr Phe Ser Tyr Ser Met
            260                 265                 270

Asn Trp Val Arg Gln Ala Pro Gly Lys Gly Leu Glu Trp Val Ser Tyr
        275                 280                 285

Ile Ser Ser Ser Ser Thr Ile Gln Tyr Ala Asp Ser Val Lys Gly
    290                 295                 300

Arg Phe Thr Ile Ser Arg Asp Asn Ala Lys Asn Ser Leu Tyr Leu Gln
305                 310                 315                 320

Met Asn Ser Leu Arg Asp Glu Asp Thr Ala Val Tyr Tyr Cys Ala Arg
                325                 330                 335

Gly Asp Tyr Tyr Tyr Gly Met Asp Val Trp Gly Gln Gly Thr Thr Val
                340                 345                 350

Thr Val Ser Ser Ile Thr Cys Pro Pro Met Ser Val Glu His Ala
            355                 360                 365

Asp Ile Trp Val Lys Ser Tyr Ser Leu Tyr Ser Arg Glu Arg Tyr Ile
        370                 375                 380

Cys Asn Ser Gly Phe Lys Arg Lys Ala Gly Thr Ser Ser Leu Thr Glu
385                 390                 395                 400

Cys Val Leu Asn Lys Ala Thr Asn Val Ala His Trp Thr Thr Pro Ser
                405                 410                 415

Leu Lys Cys Ile Arg Asp Lys Thr His Thr Cys Pro Pro Cys Pro Ala
                420                 425                 430

Pro Glu Leu Leu Gly Gly Pro Ser Val Phe Leu Phe Pro Pro Lys Pro
            435                 440                 445

Lys Asp Thr Leu Met Ile Ser Arg Thr Pro Glu Val Thr Cys Val Val
        450                 455                 460

Val Asp Val Ser His Glu Asp Pro Glu Val Lys Phe Asn Trp Tyr Val
465                 470                 475                 480

Asp Gly Val Glu Val His Asn Ala Lys Thr Lys Pro Arg Glu Glu Gln
                485                 490                 495

Tyr Asn Ser Thr Tyr Arg Val Val Ser Val Leu Thr Val Leu His Gln
                500                 505                 510

Asp Trp Leu Asn Gly Lys Glu Tyr Lys Cys Lys Val Ser Asn Lys Ala
            515                 520                 525

Leu Pro Ala Pro Ile Glu Lys Thr Ile Ser Lys Ala Lys Gly Gln Pro
        530                 535                 540

Arg Glu Pro Gln Val Tyr Thr Leu Pro Pro Ser Arg Asp Glu Leu Thr
545                 550                 555                 560

Lys Asn Gln Val Ser Leu Thr Cys Leu Val Lys Gly Phe Tyr Pro Ser
                565                 570                 575

Asp Ile Ala Val Glu Trp Glu Ser Asn Gly Gln Pro Glu Asn Asn Tyr
                580                 585                 590

Lys Thr Thr Pro Pro Val Leu Asp Ser Asp Gly Ser Phe Phe Leu Tyr
            595                 600                 605

Ser Lys Leu Thr Val Asp Lys Ser Arg Trp Gln Gln Gly Asn Val Phe
        610                 615                 620
```

Ser Cys Ser Val Met His Glu Ala Leu His Asn His Tyr Thr Gln Lys
625                 630                 635                 640

Ser Leu Ser Leu Ser Pro Gly Lys Gly Gly Gly Ser Gly Gly Gly
            645                 650                 655

Gly Ser Gly Gly Gly Ser Gly Gly Gly Ser Gly Ile Pro Pro
        660                 665                 670

His Val Gln Lys Ser Val Asn Asn Asp Met Ile Val Thr Asp Asn Asn
        675                 680                 685

Gly Ala Val Lys Phe Pro Gln Leu Cys Lys Phe Cys Asp Val Arg Phe
690                 695                 700

Ser Thr Cys Asp Asn Gln Lys Ser Cys Met Asn Asn Cys Pro Ile Thr
705                 710                 715                 720

Ser Ile Cys Glu Lys Pro Gln Glu Val Cys Val Ala Val Trp Arg Lys
            725                 730                 735

Asn Asp Glu Asn Ile Thr Leu Glu Thr Val Cys His Asp Pro Lys Leu
            740                 745                 750

Pro Tyr His Asp Phe Ile Leu Glu Asp Ala Ala Ser Pro Lys Cys Ile
            755                 760                 765

Met Lys Glu Lys Lys Pro Gly Glu Thr Phe Phe Met Cys Ser Cys
770                 775                 780

Ser Ser Asp Glu Cys Asn Asp Asn Ile Ile Phe Ser Glu Glu Tyr Asn
785                 790                 795                 800

Thr Ser Asn Pro Asp
            805

<210> SEQ ID NO 25
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Gln Cys Phe Leu Ser Glu Leu Gln
        35                  40                  45

Val Ile Ser Leu Glu Ser Gly Asp Ala Ser Ile His Asp Thr Val Glu
50                  55                  60

Asn Leu Thr Ile Leu Ala Asn Asp Ser Leu Ser Ser Asn Gly Tyr Val
65                  70                  75                  80

Thr Glu Ser Gly Cys Lys Glu Cys Glu Glu Leu Glu Ala Lys Asn Ile
            85                  90                  95

Lys Glu Phe Leu Gln Ser Phe Val His Ile Val Gln Met Phe Ile Asn
            100                 105                 110

Thr Ser Asn Ile Gln Met Thr Gln Ser Pro Ser Ser Val Ser Ala Ser
        115                 120                 125

Val Gly Asp Arg Val Thr Ile Thr Cys Arg Ala Ser Gln Asp Ile Ser
130                 135                 140

Arg Trp Leu Ala Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe

-continued

```
            165                 170                 175
Ser Gly Ser Gly Ser Gly Thr Asp Phe Ala Leu Thr Ile Ser Ser Leu
        180                 185                 190
Gln Pro Glu Asp Phe Ala Thr Tyr Tyr Cys Gln Gln Ala Asp Ser Arg
        195                 200                 205
Phe Ser Ile Thr Phe Gly Gln Gly Thr Arg Leu Glu Ile Lys Arg Gly
        210                 215                 220
Gly Gly Gly Ser Gly Gly Gly Ser Gly Gly Gly Ser Glu Val
225                 230                 235                 240
Gln Leu Val Gln Ser Gly Gly Leu Val Gln Pro Gly Gly Ser Leu
            245                 250                 255
Arg Leu Ser Cys Ala Ala Ser Gly Phe Thr Phe Ser Ser Tyr Ser Met
            260                 265                 270
Asn Trp Val Arg Gln Ala Pro Gly Lys Gly Leu Glu Trp Val Ser Tyr
            275                 280                 285
Ile Ser Ser Ser Ser Ser Thr Ile Gln Tyr Ala Asp Ser Val Lys Gly
            290                 295                 300
Arg Phe Thr Ile Ser Arg Asp Asn Ala Lys Asn Ser Leu Tyr Leu Gln
305                 310                 315                 320
Met Asn Ser Leu Arg Asp Glu Asp Thr Ala Val Tyr Tyr Cys Ala Arg
            325                 330                 335
Gly Asp Tyr Tyr Tyr Gly Met Asp Val Trp Gly Gln Gly Thr Thr Val
            340                 345                 350
Thr Val Ser Ser Ile Thr Cys Pro Pro Pro Met Ser Val Glu His Ala
            355                 360                 365
Asp Ile Trp Val Lys Ser Tyr Ser Leu Tyr Ser Arg Glu Arg Tyr Ile
            370                 375                 380
Cys Asn Ser Gly Phe Lys Arg Lys Ala Gly Thr Ser Ser Leu Thr Glu
385                 390                 395                 400
Cys Val Leu Asn Lys Ala Thr Asn Val Ala His Trp Thr Thr Pro Ser
            405                 410                 415
Leu Lys Cys Ile Arg Glu Pro Lys Ser Cys Asp Lys Thr His Thr Cys
            420                 425                 430
Pro Pro Cys Pro Ala Pro Glu Leu Leu Gly Gly Pro Ser Val Phe Leu
            435                 440                 445
Phe Pro Pro Lys Pro Lys Asp Thr Leu Met Ile Ser Arg Thr Pro Glu
            450                 455                 460
Val Thr Cys Val Val Val Asp Val Ser His Glu Asp Pro Glu Val Lys
465                 470                 475                 480
Phe Asn Trp Tyr Val Asp Gly Val Glu Val His Asn Ala Lys Thr Lys
            485                 490                 495
Pro Arg Glu Glu Gln Tyr Asn Ser Thr Tyr Arg Val Val Ser Val Leu
            500                 505                 510
Thr Val Leu His Gln Asp Trp Leu Asn Gly Lys Glu Tyr Lys Cys Lys
            515                 520                 525
Val Ser Asn Lys Ala Leu Pro Ala Pro Ile Glu Lys Thr Ile Ser Lys
            530                 535                 540
Ala Lys Gly Gln Pro Arg Glu Pro Gln Val Tyr Thr Leu Pro Pro Ser
545                 550                 555                 560
Arg Asp Glu Leu Thr Lys Asn Gln Val Ser Leu Thr Cys Leu Val Lys
            565                 570                 575
Gly Phe Tyr Pro Ser Asp Ile Ala Val Glu Trp Glu Ser Asn Gly Gln
            580                 585                 590
```

```
Pro Glu Asn Asn Tyr Lys Thr Thr Pro Pro Val Leu Asp Ser Asp Gly
            595                 600                 605

Ser Phe Phe Leu Tyr Ser Lys Leu Thr Val Asp Lys Ser Arg Trp Gln
    610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys Gly Gly Gly
                645                 650                 655

Gly Ser Gly Gly Gly Gly Ser Gly Gly Gly Ser Gly Gly Gly Gly
            660                 665                 670

Ser Gly Ile Pro Pro His Val Gln Lys Ser Val Asn Asn Asp Met Ile
            675                 680                 685

Val Thr Asp Asn Asn Gly Ala Val Lys Phe Pro Gln Leu Cys Lys Phe
            690                 695                 700

Cys Asp Val Arg Phe Ser Thr Cys Asp Asn Gln Lys Ser Cys Met Ser
705                 710                 715                 720

Asn Cys Pro Ile Thr Ser Ile Cys Glu Lys Pro Gln Glu Val Cys Val
                725                 730                 735

Ala Val Trp Arg Lys Asn Asp Glu Asn Ile Thr Leu Glu Thr Val Cys
            740                 745                 750

His Asp Pro Lys Leu Pro Tyr His Asp Phe Ile Leu Glu Asp Ala Ala
            755                 760                 765

Ser Pro Lys Cys Ile Met Lys Glu Lys Lys Pro Gly Glu Thr Phe
    770                 775                 780

Phe Met Cys Ser Cys Ser Ser Asp Glu Cys Asn Asp Asn Ile Ile Phe
785                 790                 795                 800

Ser Glu Glu Tyr Asn Thr Ser Asn Pro Asp
                805                 810

<210> SEQ ID NO 26
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Ser Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Asn Ile Gln Met Thr Gln Ser Pro Ser Ser Val Ser Ala Ser
        115                 120                 125

Val Gly Asp Arg Val Thr Ile Thr Cys Arg Ala Ser Gln Asp Ile Ser
```

-continued

```
            130                 135                 140
Arg Trp Leu Ala Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Asp Phe Ala Leu Thr Ile Ser Ser Leu
            180                 185                 190

Gln Pro Glu Asp Phe Ala Thr Tyr Tyr Cys Gln Gln Ala Asp Ser Arg
        195                 200                 205

Phe Ser Ile Thr Phe Gly Gln Gly Thr Arg Leu Glu Ile Lys Arg Gly
    210                 215                 220

Gly Gly Gly Ser Gly Gly Gly Gly Ser Gly Gly Gly Gly Ser Glu Val
225                 230                 235                 240

Gln Leu Val Gln Ser Gly Gly Gly Leu Val Gln Pro Gly Gly Ser Leu
                245                 250                 255

Arg Leu Ser Cys Ala Ala Ser Gly Phe Thr Phe Ser Ser Tyr Ser Met
            260                 265                 270

Asn Trp Val Arg Gln Ala Pro Gly Lys Gly Leu Glu Trp Val Ser Tyr
        275                 280                 285

Ile Ser Ser Ser Ser Ser Thr Ile Gln Tyr Ala Asp Ser Val Lys Gly
    290                 295                 300

Arg Phe Thr Ile Ser Arg Asp Asn Ala Lys Asn Ser Leu Tyr Leu Gln
305                 310                 315                 320

Met Asn Ser Leu Arg Asp Glu Asp Thr Ala Val Tyr Tyr Cys Ala Arg
                325                 330                 335

Gly Asp Tyr Tyr Tyr Gly Met Asp Val Trp Gly Gln Gly Thr Thr Val
            340                 345                 350

Thr Val Ser Ser Ile Thr Cys Pro Pro Pro Met Ser Val Glu His Ala
        355                 360                 365

Asp Ile Trp Val Lys Ser Tyr Ser Leu Tyr Ser Arg Glu Arg Tyr Ile
    370                 375                 380

Cys Asn Ser Gly Phe Lys Arg Lys Ala Gly Thr Ser Ser Leu Thr Glu
385                 390                 395                 400

Cys Val Leu Asn Lys Ala Thr Asn Val Ala His Trp Thr Thr Pro Ser
                405                 410                 415

Leu Lys Cys Ile Arg Glu Pro Lys Ser Cys Asp Lys Thr His Thr Cys
            420                 425                 430

Pro Pro Cys Pro Ala Pro Glu Leu Leu Gly Gly Pro Ser Val Phe Leu
        435                 440                 445

Phe Pro Pro Lys Pro Lys Asp Thr Leu Met Ile Ser Arg Thr Pro Glu
    450                 455                 460

Val Thr Cys Val Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Asn Ser Thr Tyr Arg Val Val Ser Val Leu
            500                 505                 510

Thr Val Leu His Gln Asp Trp Leu Asn Gly Lys Glu Tyr Lys Cys Lys
        515                 520                 525

Val Ser Asn Lys Ala Leu Pro Ala Pro Ile Glu Lys Thr Ile Ser Lys
    530                 535                 540

Ala Lys Gly Gln Pro Arg Glu Pro Gln Val Tyr Thr Leu Pro Pro Ser
545                 550                 555                 560
```

Arg Asp Glu Leu Thr Lys Asn Gln Val Ser Leu Thr Cys Leu Val Lys
            565                 570                 575

Gly Phe Tyr Pro Ser Asp Ile Ala Val Glu Trp Glu Ser Asn Gly Gln
            580                 585                 590

Pro Glu Asn Asn Tyr Lys Thr Thr Pro Pro Val Leu Asp Ser Asp Gly
            595                 600                 605

Ser Phe Phe Leu Tyr Ser Lys Leu Thr Val Asp Lys Ser Arg Trp Gln
            610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys Gly Gly Gly
            645                 650                 655

Gly Ser Gly Gly Gly Gly Ser Gly Gly Gly Gly Ser Gly Gly Gly Gly
            660                 665                 670

Ser Gly Ile Pro Pro His Val Gln Lys Ser Val Asn Asn Asp Met Ile
            675                 680                 685

Val Thr Asp Asn Asn Gly Ala Val Lys Phe Pro Gln Leu Cys Lys Phe
            690                 695                 700

Cys Asp Val Arg Phe Ser Thr Cys Asp Asn Gln Lys Ser Cys Met Ser
705                 710                 715                 720

Asn Cys Pro Ile Thr Ser Ile Cys Glu Lys Pro Gln Glu Val Cys Val
            725                 730                 735

Ala Val Trp Arg Lys Asn Asp Glu Asn Ile Thr Leu Glu Thr Val Cys
            740                 745                 750

His Asp Pro Lys Leu Pro Tyr His Asp Phe Ile Leu Glu Asp Ala Ala
            755                 760                 765

Ser Pro Lys Cys Ile Met Lys Glu Lys Lys Pro Gly Glu Thr Phe
            770                 775                 780

Phe Met Cys Ser Cys Ser Ser Asp Glu Cys Asn Asp Asn Ile Ile Phe
785                 790                 795                 800

Ser Glu Glu Tyr Asn Thr Ser Asn Pro Asp
            805                 810

<210> SEQ ID NO 27
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asn Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ala Asp Ser Arg Phe Ser
            85                  90                  95

Ile Thr Phe Gly Gln Gly Thr Arg Leu Glu Ile Lys Arg Gly Gly Gly

```
                   100                 105                 110
Gly Ser Gly Gly Gly Ser Gly Gly Gly Ser Glu Val Gln Leu
            115                 120                 125

Val Gln Ser Gly Gly Gly Leu Val Gln Pro Gly Gly Ser Leu Arg Leu
            130                 135                 140

Ser Cys Ala Ala Ser Gly Phe Thr Phe Ser Ser Tyr Ser Met Asn Trp
145                 150                 155                 160

Val Arg Gln Ala Pro Gly Lys Gly Leu Glu Trp Val Ser Tyr Ile Ser
                165                 170                 175

Ser Ser Ser Ser Thr Ile Gln Tyr Ala Asp Ser Val Lys Gly Arg Phe
            180                 185                 190

Thr Ile Ser Arg Asp Asn Ala Lys Asn Ser Leu Tyr Leu Gln Met Asn
            195                 200                 205

Ser Leu Arg Asp Glu Asp Thr Ala Val Tyr Tyr Cys Ala Arg Gly Asp
            210                 215                 220

Tyr Tyr Tyr Gly Met Asp Val Trp Gly Gln Gly Thr Thr Val Thr Val
225                 230                 235                 240

Ser Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270

Val His Pro Ser Cys Lys Val Thr Ala Met Lys Cys Phe Leu Leu Glu
            275                 280                 285

Leu Gln Val Ile Ser Leu Glu Ser Gly Asp Ala Ser Ile His Asp Thr
            290                 295                 300

Val Glu Asn Leu Ile Ile Leu Ala Asn Asp Ser Leu Ser Ser Asn Gly
305                 310                 315                 320

Asn Val Thr Glu Ser Gly Cys Lys Glu Cys Glu Glu Leu Glu Glu Lys
                325                 330                 335

Asn Ile Lys Glu Phe Leu Gln Ser Phe Val His Ile Val Gln Met Phe
            340                 345                 350

Ile Asn Thr Ser
            355

<210> SEQ ID NO 28
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Glu Pro Lys Ser Cys Asp Lys Thr His Thr Cys Pro Pro Cys Pro
65              70                  75                  80

Ala Pro Glu Leu Leu Gly Gly Pro Ser Val Phe Leu Phe Pro Pro Lys
            85                  90                  95
```

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys Gly Gly Gly Ser Gly Gly
290                 295                 300

Gly Gly Ser Gly Gly Gly Ser Gly Gly Gly Ser Gly Ile Pro
305                 310                 315                 320

Pro His Val Gln Lys Ser Val Asn Asn Asp Met Ile Val Thr Asp Asn
            325                 330                 335

Asn Gly Ala Val Lys Phe Pro Gln Leu Cys Lys Phe Cys Asp Val Arg
        340                 345                 350

Phe Ser Thr Cys Asp Asn Gln Lys Ser Cys Met Ser Asn Cys Pro Ile
    355                 360                 365

Thr Ser Ile Cys Glu Lys Pro Gln Glu Val Cys Val Ala Val Trp Arg
370                 375                 380

Lys Asn Asp Glu Asn Ile Thr Leu Glu Thr Val Cys His Asp Pro Lys
385                 390                 395                 400

Leu Pro Tyr His Asp Phe Ile Leu Glu Asp Ala Ala Ser Pro Lys Cys
                405                 410                 415

Ile Met Lys Glu Lys Lys Lys Pro Gly Glu Thr Phe Phe Met Cys Ser
            420                 425                 430

Cys Ser Ser Asp Glu Cys Asn Asp Asn Ile Ile Phe Ser Glu Glu Tyr
        435                 440                 445

Asn Thr Ser Asn Pro Asp
    450

<210> SEQ ID NO 29
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asn Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ala Asp Ser Arg Phe Ser
                85                  90                  95

Ile Thr Phe Gly Gln Gly Thr Arg Leu Glu Ile Lys Arg Gly Gly Gly
            100                 105                 110

Gly Ser Gly Gly Gly Gly Ser Gly Gly Gly Ser Glu Val Gln Leu
        115                 120                 125

Val Gln Ser Gly Gly Gly Leu Val Gln Pro Gly Gly Ser Leu Arg Leu
    130                 135                 140

Ser Cys Ala Ala Ser Gly Phe Thr Phe Ser Ser Tyr Ser Met Asn Trp
145                 150                 155                 160

Val Arg Gln Ala Pro Gly Lys Gly Leu Glu Trp Val Ser Tyr Ile Ser
                165                 170                 175

Ser Ser Ser Ser Thr Ile Gln Tyr Ala Asp Ser Val Lys Gly Arg Phe
            180                 185                 190

Thr Ile Ser Arg Asp Asn Ala Lys Asn Ser Leu Tyr Leu Gln Met Asn
        195                 200                 205

Ser Leu Arg Asp Glu Asp Thr Ala Val Tyr Tyr Cys Ala Arg Gly Asp
210                 215                 220

Tyr Tyr Tyr Gly Met Asp Val Trp Gly Gln Gly Thr Thr Val Thr Val
225                 230                 235                 240

Ser Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270

Val His Pro Ser Cys Lys Val Thr Ala Met Lys Cys Phe Leu Leu Glu
        275                 280                 285

Leu Gln Val Ile Ser Leu Glu Ser Gly Asp Ala Ser Ile His Asp Thr
290                 295                 300

Val Glu Asn Leu Ile Ile Leu Ala Asn Asp Ser Leu Ser Ser Asn Gly
305                 310                 315                 320

Asn Val Thr Glu Ser Gly Cys Lys Glu Cys Glu Glu Leu Glu Glu Lys
                325                 330                 335

Asn Ile Lys Glu Phe Leu Gln Ser Phe Val His Ile Val Gln Met Phe
            340                 345                 350

Ile Asn Thr Ser
        355

<210> SEQ ID NO 30
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 30

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys Gly Gly Gly Ser Gly Gly
    290                 295                 300

Gly Gly Ser Gly Gly Gly Ser Gly Gly Gly Ser Gly Ile Pro
305                 310                 315                 320

Pro His Val Gln Lys Ser Val Asn Asn Asp Met Ile Val Thr Asp Asn
                325                 330                 335

Asn Gly Ala Val Lys Phe Pro Gln Leu Cys Lys Phe Cys Asp Val Arg
            340                 345                 350

Phe Ser Thr Cys Asp Asn Gln Lys Ser Cys Met Ser Asn Cys Pro Ile
        355                 360                 365

Thr Ser Ile Cys Glu Lys Pro Gln Glu Val Cys Val Ala Val Trp Arg
    370                 375                 380

Lys Gln Asp Glu Asn Ile Thr Leu Glu Thr Val Cys His Asp Pro Lys
385                 390                 395                 400

Leu Pro Tyr His Asp Phe Ile Leu Glu Asp Ala Ala Ser Pro Lys Cys
                405                 410                 415
```

Ile Met Lys Glu Lys Lys Pro Gly Glu Thr Phe Phe Met Cys Ser
                420                 425                 430

Cys Ser Ser Asp Glu Cys Asn Asp Asn Ile Ile Phe Ser Glu Glu Tyr
            435                 440                 445

Gln Thr Ser Asn Pro Asp
    450

<210> SEQ ID NO 31
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asn Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ala Asp Ser Arg Phe Ser
                85                  90                  95

Ile Thr Phe Gly Gln Gly Thr Arg Leu Glu Ile Lys Arg Gly Gly Gly
            100                 105                 110

Gly Ser Gly Gly Gly Gly Ser Gly Gly Gly Ser Glu Val Gln Leu
        115                 120                 125

Val Gln Ser Gly Gly Gly Leu Val Gln Pro Gly Gly Ser Leu Arg Leu
    130                 135                 140

Ser Cys Ala Ala Ser Gly Phe Thr Phe Ser Ser Tyr Ser Met Asn Trp
145                 150                 155                 160

Val Arg Gln Ala Pro Gly Lys Gly Leu Glu Trp Val Ser Tyr Ile Ser
                165                 170                 175

Ser Ser Ser Ser Thr Ile Gln Tyr Ala Asp Ser Val Lys Gly Arg Phe
            180                 185                 190

Thr Ile Ser Arg Asp Asn Ala Lys Asn Ser Leu Tyr Leu Gln Met Asn
        195                 200                 205

Ser Leu Arg Asp Glu Asp Thr Ala Val Tyr Tyr Cys Ala Arg Gly Asp
    210                 215                 220

Tyr Tyr Tyr Gly Met Asp Val Trp Gly Gln Gly Thr Thr Val Thr Val
225                 230                 235                 240

Ser Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270

Val His Pro Ser Cys Lys Val Thr Ala Met Lys Cys Phe Leu Leu Glu
        275                 280                 285

Leu Gln Val Ile Ser Leu Glu Ser Gly Asp Ala Ser Ile His Asp Thr
    290                 295                 300

Val Glu Asn Leu Ile Ile Leu Ala Asn Asp Ser Leu Ser Ser Asn Gly

```
                    305                 310                 315                 320
Asn Val Thr Glu Ser Gly Cys Lys Glu Cys Glu Glu Leu Gly Glu Lys
                325                 330                 335
Asn Ile Lys Glu Phe Leu Gln Ser Phe Val His Ile Val Gln Met Phe
                340                 345                 350
Ile Asn Thr Ser
        355

<210> SEQ ID NO 32
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Ile Thr Cys Pro Pro Pro Met Ser
        130                 135                 140

Val Glu His Ala Asp Ile Trp Val Lys Ser Tyr Ser Leu Tyr Ser Arg
145                 150                 155                 160

Glu Arg Tyr Ile Cys Asn Ser Gly Phe Lys Arg Lys Ala Gly Thr Ser
                165                 170                 175

Ser Leu Thr Glu Cys Val Leu Asn Lys Ala Thr Asn Val Ala His Trp
                180                 185                 190

Thr Thr Pro Ser Leu Lys Cys Ile Arg Glu Pro Lys Ser Cys Asp Lys
            195                 200                 205

Thr His Thr Cys Pro Pro Cys Pro Ala Pro Glu Leu Leu Gly Gly Pro
        210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
                260                 265                 270

Ala Lys Thr Lys Pro Arg Glu Glu Gln Tyr Asn Ser Thr Tyr Arg Val
            275                 280                 285

Val Ser Val Leu Thr Val Leu His Gln Asp Trp Leu Asn Gly Lys Glu
        290                 295                 300
```

```
Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Tyr Thr
            325                 330                 335

Leu Pro Pro Ser Arg Asp Glu Leu Thr Lys Asn Gln Val Ser Leu Thr
            340                 345                 350

Cys Leu Val Lys Gly Phe Tyr Pro Ser Asp Ile Ala Val Glu Trp Glu
                355                 360                 365

Ser Asn Gly Gln Pro Glu Asn Asn Tyr Lys Thr Thr Pro Pro Val Leu
            370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
                420                 425                 430

Lys

<210> SEQ ID NO 33
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asn Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ala Asp Ser Arg Phe Ser
                85                  90                  95

Ile Thr Phe Gly Gln Gly Thr Arg Leu Glu Ile Lys Arg Gly Gly Gly
            100                 105                 110

Gly Ser Gly Gly Gly Gly Ser Gly Gly Gly Gly Ser Glu Val Gln Leu
        115                 120                 125

Val Gln Ser Gly Gly Gly Leu Val Gln Pro Gly Gly Ser Leu Arg Leu
    130                 135                 140

Ser Cys Ala Ala Ser Gly Phe Thr Phe Ser Ser Tyr Ser Met Asn Trp
145                 150                 155                 160

Val Arg Gln Ala Pro Gly Lys Gly Leu Glu Trp Val Ser Tyr Ile Ser
                165                 170                 175

Ser Ser Ser Ser Thr Ile Gln Tyr Ala Asp Ser Val Lys Gly Arg Phe
            180                 185                 190

Thr Ile Ser Arg Asp Asn Ala Lys Asn Ser Leu Tyr Leu Gln Met Asn
        195                 200                 205

Ser Leu Arg Asp Glu Asp Thr Ala Val Tyr Tyr Cys Ala Arg Gly Asp
    210                 215                 220
```

Tyr Tyr Tyr Gly Met Asp Val Trp Gly Gln Gly Thr Thr Val Thr Val
225                 230                 235                 240

Ser Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270

Val His Pro Ser Cys Lys Val Thr Ala Met Lys Cys Phe Leu Leu Glu
        275                 280                 285

Leu Gln Val Ile Ser Leu Glu Ser Gly Asp Ala Ser Ile His Asp Thr
    290                 295                 300

Val Glu Asn Leu Ile Ile Leu Ala Asn Asp Ser Leu Ser Ser Asn Gly
305                 310                 315                 320

Asn Val Thr Glu Ser Gly Cys Lys Glu Cys Glu Glu Leu Glu Glu Lys
                325                 330                 335

Asn Ile Lys Glu Phe Leu Gln Ser Phe Val His Ile Val Gln Met Phe
            340                 345                 350

Ile Asn Thr Ser
        355

<210> SEQ ID NO 34
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Gln Asn Cys
        35                  40                  45

Pro Ile Thr Ser Ile Cys Glu Lys Pro Gln Glu Val Cys Val Ala Val
    50                  55                  60

Trp Arg Lys Gln Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Gln Thr Ser Asn Pro Asp Ile Thr Cys Pro Pro Pro Met Ser
    130                 135                 140

Val Glu His Ala Asp Ile Trp Val Lys Ser Tyr Ser Leu Tyr Ser Arg
145                 150                 155                 160

Glu Arg Tyr Ile Cys Asn Ser Gly Phe Lys Arg Lys Ala Gly Thr Ser
                165                 170                 175

Ser Leu Thr Glu Cys Val Leu Asn Lys Ala Thr Asn Val Ala His Trp
            180                 185                 190

Thr Thr Pro Ser Leu Lys Cys Ile Arg Glu Pro Lys Ser Cys Asp Lys
        195                 200                 205

Thr His Thr Cys Pro Pro Cys Pro Ala Pro Glu Leu Leu Gly Gly Pro
    210                 215                 220

```
Ser Val Phe Leu Phe Pro Lys Pro Lys Asp Thr Leu Met Ile Ser
225                 230                 235                 240

Arg Thr Pro Glu Val Thr Cys Val Val Asp Val Ser His Glu Asp
                    245                 250                 255

Pro Glu Val Lys Phe Asn Trp Tyr Val Asp Gly Val Glu Val His Asn
                260                 265                 270

Ala Lys Thr Lys Pro Arg Glu Glu Gln Tyr Asn Ser Thr Tyr Arg Val
            275                 280                 285

Val Ser Val Leu Thr Val Leu His Gln Asp Trp Leu Asn Gly Lys Glu
        290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Arg Asp Glu Leu Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys

<210> SEQ ID NO 35
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Gln Asn Cys
            35                  40                  45

Pro Ile Thr Ser Ile Cys Glu Lys Pro Gln Glu Val Cys Val Ala Val
        50                  55                  60

Trp Arg Lys Gln Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Gln Thr Ser Asn Pro Asp
    130                 135
```

<210> SEQ ID NO 36
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 37
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Asp Glu Leu Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290

<210> SEQ ID NO 38
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Gln Cys Phe Leu Ser Glu Leu Gln
        35                  40                  45

Val Ile Ser Leu Glu Ser Gly Asp Ala Ser Ile His Asp Thr Val Glu
```

```
                    50                  55                  60

Asn Leu Thr Ile Leu Ala Asn Asp Ser Leu Ser Ser Asn Gly Tyr Val
 65                  70                  75                  80

Thr Glu Ser Gly Cys Lys Glu Cys Glu Glu Leu Glu Ala Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 39
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Ser Glu Leu Gln
             35                  40                  45

Val Ile Ser Leu Glu Ser Gly Asp Ala Ser Ile His Asp Thr Val Glu
 50                  55                  60

Asn Leu Ile Ile Leu Ala Asn Asp Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Pro Lys Ser Cys
 1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Glu Leu Leu Gly Gly
 1               5

<210> SEQ ID NO 42
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 42

Pro Glu Ala Ala Gly Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Cys Lys Ser Leu
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Cys Ala Ser Leu
1               5

<210> SEQ ID NO 45
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160
```

```
Gln Asp Trp Leu Asn Gly Lys Glu Tyr Lys Cys Lys Val Ser Asn Lys
            165                 170                 175

Ala Leu Pro Ala Pro Ile Glu Lys Thr Ile Ser Lys Ala Lys Gly Gln
        180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
        210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
            245                 250                 255

Tyr Ser Lys Leu Thr Val Asp Lys Ser Arg Trp Gln Gln Gly Asn Val
        260                 265                 270

Phe Ser Cys Ser Val Met His Glu Ala Leu His Asn His Tyr Thr Gln
        275                 280                 285

Lys Ser Leu Ser Leu Ser Pro Gly Lys
        290                 295

<210> SEQ ID NO 46
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Asn Ile Gln Met Thr Gln Ser Pro Ser Ser Val Ser Ala Ser
        115                 120                 125

Val Gly Asp Arg Val Thr Ile Thr Cys Arg Ala Ser Gln Asp Ile Ser
    130                 135                 140

Arg Trp Leu Ala Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Asp Phe Ala Leu Thr Ile Ser Ser Leu
            180                 185                 190

Gln Pro Glu Asp Phe Ala Thr Tyr Tyr Cys Gln Gln Ala Asp Ser Arg
        195                 200                 205

Phe Ser Ile Thr Phe Gly Gln Gly Thr Arg Leu Glu Ile Lys Arg Gly
    210                 215                 220
```

```
Gly Gly Gly Ser Gly Gly Gly Ser Gly Gly Gly Ser Glu Val
225                 230                 235                 240

Gln Leu Val Gln Ser Gly Gly Leu Val Gln Pro Gly Gly Ser Leu
        245                 250                 255

Arg Leu Ser Cys Ala Ala Ser Gly Phe Thr Phe Ser Tyr Ser Met
            260                 265                 270

Asn Trp Val Arg Gln Ala Pro Gly Lys Gly Leu Glu Trp Val Ser Tyr
        275                 280                 285

Ile Ser Ser Ser Ser Thr Ile Gln Tyr Ala Asp Ser Val Lys Gly
    290                 295                 300

Arg Phe Thr Ile Ser Arg Asp Asn Ala Lys Asn Ser Leu Tyr Leu Gln
305                 310                 315                 320

Met Asn Ser Leu Arg Asp Glu Asp Thr Ala Val Tyr Tyr Cys Ala Arg
                325                 330                 335

Gly Asp Tyr Tyr Tyr Gly Met Asp Val Trp Gly Gln Gly Thr Thr Val
            340                 345                 350

Thr Val Ser Ser Ile Thr Cys Pro Pro Met Ser Val Glu His Ala
        355                 360                 365

Asp Ile Trp Val Lys Ser Tyr Ser Leu Tyr Ser Arg Glu Arg Tyr Ile
370                 375                 380

Cys Asn Ser Gly Phe Lys Arg Lys Ala Gly Thr Ser Ser Leu Thr Glu
385                 390                 395                 400

Cys Val Leu Asn Lys Ala Thr Asn Val Ala His Trp Thr Thr Pro Ser
            405                 410                 415

Leu Lys Cys Ile Arg Glu Pro Lys Ser Cys Asp Lys Thr His Thr Cys
            420                 425                 430

Pro Pro Cys Pro Ala Pro Glu Leu Leu Gly Gly Pro Ser Val Phe Leu
        435                 440                 445

Phe Pro Pro Lys Pro Lys Asp Thr Leu Met Ile Ser Arg Thr Pro Glu
    450                 455                 460

Val Thr Cys Val Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Asn Ser Thr Tyr Arg Val Val Ser Val Leu
            500                 505                 510

Thr Val Leu His Gln Asp Trp Leu Asn Gly Lys Glu Tyr Lys Cys Lys
        515                 520                 525

Val Ser Asn Lys Ala Leu Pro Ala Pro Ile Glu Lys Thr Ile Ser Lys
    530                 535                 540

Ala Lys Gly Gln Pro Arg Glu Pro Gln Val Tyr Thr Leu Pro Pro Ser
545                 550                 555                 560

Arg Asp Glu Leu Thr Lys Asn Gln Val Ser Leu Thr Cys Leu Val Lys
                565                 570                 575

Gly Phe Tyr Pro Ser Asp Ile Ala Val Glu Trp Glu Ser Asn Gly Gln
            580                 585                 590

Pro Glu Asn Asn Tyr Lys Thr Thr Pro Pro Val Leu Asp Ser Asp Gly
        595                 600                 605

Ser Phe Phe Leu Tyr Ser Lys Leu Thr Val Asp Lys Ser Arg Trp Gln
    610                 615                 620

Gln Gly Asn Val Phe Ser Cys Ser Val Met His Glu Ala Leu His Asn
625                 630                 635                 640
```

-continued

```
His Tyr Thr Gln Lys Ser Leu Ser Leu Ser Pro Gly Lys Gly Gly Gly
                645                 650                 655

Gly Ser Gly Gly Gly Ser Gly Gly Gly Ser Gly Gly Gly Gly
            660             665             670

Ser Gly Ile Pro Pro His Val Gln Lys Ser Val Asn Asn Asp Met Ile
        675             680             685

Val Thr Asp Asn Asn Gly Ala Val Lys Phe Pro Gln Leu Cys Lys Phe
    690             695             700

Cys Asp Val Arg Phe Ser Thr Cys Asp Asn Gln Lys Ser Cys Met Asn
705             710             715             720

Asn Cys Pro Ile Thr Ser Ile Cys Glu Lys Pro Gln Glu Val Cys Val
            725             730             735

Ala Val Trp Arg Lys Asn Asp Glu Asn Ile Thr Leu Glu Thr Val Cys
            740             745             750

His Asp Pro Lys Leu Pro Tyr His Asp Phe Ile Leu Glu Asp Ala Ala
        755             760             765

Ser Pro Lys Cys Ile Met Lys Glu Lys Lys Pro Gly Glu Thr Phe
    770             775             780

Phe Met Cys Ser Cys Ser Ser Asp Glu Cys Asn Asp Asn Ile Ile Phe
785             790             795             800

Ser Glu Glu Tyr Asn Thr Ser Asn Pro Asp
                805             810
```

ANTI-PDL1, IL-15 AND TGF-BETA RECEPTOR COMBINATION MOLECULES

CROSS REFERENCE TO RELATED APPLICATIONS

This application claims the benefit of priority under 35 U.S.C. § 119(e) to U.S. Provisional Application No. 62/648,373 filed Mar. 26, 2018, and U.S. Provisional Application No. 62/734,994 filed Sep. 21, 2018. The entire contents of these applications are incorporated herein by reference in their entirety.

INCORPORATION BY REFERENCE OF SEQUENCE LISTING

The instant application contains a Sequence Listing which has been filed electronically in ASCII format and is hereby incorporated by reference in its entirety. Said ASCII copy, created on Aug. 26, 2019, is named 055537-508001US-_SL.txt and is 146,969 bytes in size.

FIELD OF THE INVENTION

This invention relates generally to the field of multimeric fusion molecules.

BACKGROUND OF THE INVENTION

Cancer immunotherapy studies have now demonstrated promising clinical response rates in patients with melanoma and subsets of patients with other solid tumors. Those studies have involved monoclonal antibody (MAb) checkpoint inhibitors such as anti-CTLA4, anti-programmed cell death-1 (PD-1), and anti-programmed cell death protein-1 ligand (PD-L1), as well as cytokines such as IL-2 and IL-15.[1-5]

Most antibodies directed against PD-1/PD-L1 are of the IgG4 isotype, or of the IgG1 isotype engineered with an Fc domain mutation to impair antibody dependent cellular cytotoxicity (ADCC) activity. Multiple anti-cancer MAbs, such as anti-CTLA4 (ipilimumab), anti-CD20 (rituximab), anti-HER2 (trastuzumab, pertuzumab), and anti-EGFR (cetuximab), however, are of the IgG1 isotype, and thus have the potential to mediate ADCC. The ADCC mechanism has been implicated to contribute to clinical efficacy,[9-11] although other studies have not supported this finding. Atezolizumab (TECENTRIQ®, Genentech) and avelumab (BAVENCIO®, EMD Serono) are fully human anti-PD-L therapies of the IgG1 isotype that have been FDA approved for the treatment of non-small cell lung cancer (NSCLC), bladder cancer, urothelial cancer, and metastatic Merkel cell carcinoma.[2-15]

Since PD-L1 is expressed on some immune cells, studies were conducted to evaluate avelumab-mediated ADCC using whole peripheral blood mononuclear cells (PBMC) as targets. Using natural killer (NK) cells from healthy donors and cancer patients, substantial lysis of a range of human tumor cell types was observed, with little or no lysis when human PBMC subsets were used as targets. Similar results were also seen in the analysis of 123 immune cell subsets from PBMC of patients treated with up to nine doses of avelumab.[13,16] Moreover, while clinical benefit of using avelumab has been observed in a range of human tumors, adverse events beyond those seen with other anti-PD1/PD-L1 MAbs have not been observed.[3,14,17,18]

Despite the promising results described above, only 10-30% of patients with most carcinomas achieve objective responses when treated with anti-PD-1/PD-L1 monotherapies, even in trials that enrolled only those patients whose pre-treatment tumor specimens expressed PD-L1.[19]

Prior to the invention described herein, there was a pressing need to develop new strategies to target various effector molecules to a disease site to provide therapeutic benefit without the side effects associated with non-specific immune activity.

SUMMARY

The invention is based, at least in part, on the surprising discovery that multi-specific IL-15-based protein complexes enhance the stimulation of immune cells and promote their activity against disease cells, thereby resulting in reduction or prevention of disease. These IL-15-based protein complexes also show increased binding to disease and target antigens. Provided herein are multi-specific protein complexes with at least one domain comprising IL-15 or a functional variant, a transforming growth factor-beta receptor type 2 (TGFβRII) domain, and a binding domain specific to a disease antigen, immune checkpoint or signaling molecule. In particular, the complexes comprise an IL-15N72D:IL-15Rα Su/Fc scaffold fused to an antibody or antibody binding fragment and a TGFβRII domain which binds transforming growth factor-beta (TGFβ).

Specifically, described herein are protein complexes comprising binding domains that specifically bind to programmed death ligand 1 (PD-L1), programmed death 1 (PD-1), cytotoxic T-lymphocyte associated protein 4 (CTLA-4), cluster of differentiation 47 (CD47), T-cell immunoglobulin and mucin-domain containing-3 (TIM-3, TIM3) or glucocorticoid-induced tumor necrosis factor receptor (TNFR) family related gene (GITR). These complexes augment immune activity by providing immunostimulatory cytokines to the immune cells. Such cytokines are known in the art and can be used alone or in combination with other cytokines or agents. These complexes further augment immune responses through immune checkpoint blockade via the anti-PD-L1, PD-1, CTLA-4, CD47, TIM3 or GITR binding domains. Finally, the complexes can bind TGFβ and block its immunosuppressive activities that in turn promote tumor growth and metastasis and other diseases.

In some cases, these complexes also recognize antigens, such as PD-L1, single stranded deoxyribonucleic acid (ssDNA), CD20, human epidermal growth factor receptor 2 (HER2), epidermal growth factor receptor (EGFR), CD19, CD38, CD52, disialoganglioside (GD2), CD33, Notch1, intercellular adhesion molecule 1 (ICAM-1), tissue factor or HIV envelope, expressed on disease cells and stimulate antibody-dependent cell-mediated cytotoxicity (ADCC) and complement-dependent cytotoxicity (CDC) against the disease cell via the Fc binding domain.

Provided is an isolated soluble fusion protein complex comprising at least two soluble proteins. For example, the first protein comprises an interleukin-15 (IL-15) polypeptide, e.g., a variant IL-15 polypeptide comprising an N72D mutation (IL-15N72D). The second protein comprises a soluble IL-15 receptor alpha sushi-binding domain (IL-15RαSu) fused to an immunoglobulin Fc domain (IL-15RαSu/Fc). A third component of the isolated soluble fusion protein complex comprises a binding domain that recognizes a disease antigen, immune checkpoint molecule or a signaling molecule, e.g., PD-L1, PD-1, CTLA-4, CD47, TIM3 or GITR, wherein the binding domain is fused to the either the IL-15N72D or the IL-15RαSu/Fc protein. A fourth component of the soluble fusion immune complex comprises a cytokine receptor, e.g. TGFβRII, or cytokine. In some aspects, these binding domains are fused to both the IL-15N72D and IL-15RαSu/Fc proteins. In other aspects, one of these binding domains is fused to the IL-15N72D or the IL-15RαSu/Fc proteins and a second binding domain, i.e. specific to an immune checkpoint or signaling molecule or a disease antigen, is fused to the same or other protein. In some aspects, the cytokine receptor, e.g. TGFβRII, is fused to the IL-15N72D and/or IL-15RαSu/Fc proteins. In some aspects the cytokine receptor, e.g. TGFβRII, is fused or linked to the IgG1 Fc via a linker molecule. In another aspect, the cytokine receptor, e.g. TGFβRII, is a dimer fused to IL-15N72D and IL-15RαSu/Fc proteins. In one aspect, the disease antigen is associated with neoplasia, infectious disease, or autoimmune disease. In some cases, the first and/or second soluble protein further comprises a binding domain that recognizes a disease antigen, e.g., PD-L1, ssDNA, CD20, HER2, EGFR, CD19, CD38, CD52, GD2, CD33, Notch1, intercellular adhesion molecule 1 (ICAM-1), tissue factor or HIV envelope or other known antigens, expressed on disease cells. Alternatively, either the IL-15N72D or the IL-15RαSu/Fc protein comprise the binding domain specific to a disease antigen, immune checkpoint or signaling molecule and the other protein (IL-15RαSu/Fc or IL-15N72D protein, respectively) do not comprise an additional fused binding domain. The IL-15N72D domain of the first protein binds to the soluble IL-15RαSu domain of the second protein to form a soluble fusion protein complex. An exemplary fusion protein complex comprises an anti-PD-L1 antibody covalently linked to an IL-15N72D and/or an IL-15RαSu/Fc fusion protein. In other aspects, a cytokine receptor, e.g. TGFβRII, and/or the binding domain are covalently linked to a soluble IL-15 receptor alpha sushi-binding domain (IL-15RαSu) fused to an immunoglobulin Fc domain whereas the second protein comprises a binding domain that recognizes disease antigens covalently linked and a variant interleukin-15 (IL-15) polypeptide comprising an N72D mutation (IL-15N72D). In another aspect, the second protein comprises a cytokine receptor, e.g. TGFβRII.

In certain embodiments, an isolated soluble fusion protein complex comprises at least two soluble proteins, wherein a first soluble protein comprises an interleukin-15 (IL-15) polypeptide domain and a second soluble protein comprises a soluble IL-15 receptor alpha sushi-binding domain (IL-15RαSu) fused to an immunoglobulin Fc domain, wherein the immunoglobulin Fc (IgG Fc) domain is fused or linked to a glycosylate or an aglycosylated transforming growth factor-beta receptor type 2 (TGFβRII) domain; the first and/or second soluble protein further comprises a binding domain that specifically binds to a disease antigen, immune checkpoint molecule or immune signaling molecule, and the IL-15 domain of the first soluble protein binds to the IL-15RαSu domain of the second soluble protein to form a soluble fusion protein complex. An example of an aglycosylated TGFβRII amino acid sequence is as follows:

(SEQ ID NO: 35)
IPPHVQKSVNNDMIVTDNNGAVKFPQLCKFCDVRFSTCDNQKSCMQNCPI

TSICEKPQEVCVAVWRKQDENITLETVCHDPKLPYHDFILEDAASPKCIM

KEKKKPGETFFMCSCSSDECNDNIIFSEEYQTSNPD.

In this and other embodiments, the immunoglobulin Fc domain is linked to a transforming growth factor-beta receptor type 2 (TGFβRII) domain via a linker molecule. In these and other embodiments, the immunoglobulin Fc domain is an IgG Fc variant comprising a hinge region lacking a free cysteine at residue position 70. In certain embodiments, the cysteine is substituted with a serine at residue position 70 (IgGFcC70S). An example of Δfree cysteine IL15RαSuFc amino acid sequence is as follows:

(SEQ ID NO: 36)
ITCPPPMSVEHADIWVKSYSLYSRERYICNSGFKRKAGTSSLTECVLNKA

TNVAHWTTPSLKCIREPKSSDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK.

In certain embodiments, the immunoglobulin Fc domain is an IgG-Fc variant lacking a hinge region. For example, the IL15RαSuFc lacks the amino acid residues EPKSC (SEQ ID NO: 40) at positions 66 to 70. An example of Δhinge IL15RαSuFc amino acid sequence is as follows:

(SEQ ID NOS 37
ITCPPPMSVEHADIWVKSYSLYSRERYICNSGFKRKAGTSSLTECVLNKA

TNVAHWTTPSLKCIRDKTHTCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGK and 45 with the "EPKSC" region deleted and included, respectively)

In these and other embodiments, one of the first or second soluble protein further comprises a second binding domain that specifically binds to a disease antigen, immune checkpoint molecule, or immune signaling molecule. In these and other embodiments, the IL-15 polypeptide is an IL-15 variant comprising an N72D mutation (IL-15N72D), an IL-15K41Q mutation, an IL-15L45S mutation, an IL-15I67T mutation, an IL-15N79Y mutation, an IL-15E93A mutation or combinations thereof. An example of IL-15-K41Q, L45S, I67T, N79Y, E93A amino acid sequence is as follows:

(SEQ ID NO: 38)
NWVNVISDLKKIEDLIQSMHIDATLYTESDVHPSCKVTAMQCFLSELQVI

SLESGDASIHDTVENLTILANDSLSSNGYVTESGCKECEELEAKNIKEFL

QSFVHIVQMFINTS.

In certain embodiments, the IL-15 polypeptide is an IL-15 variant comprising an L45S mutation. An example of IL15-L45S amino acid sequence is as follows:

(SEQ ID NO: 39)
NWVNVISDLKKIEDLIQSMHIDATLYTESDVHPSCKVTAMKCFLSELQVI

SLESGDASIHDTVENLIILANDSLSSNGNVTESGCKECEELEEKNIKEFL

QSFVHIVQMFINTS.

In certain embodiments, the binding domain comprises an immunoglobulin light chain variable domain covalently linked to an immunoglobulin heavy chain variable domain by a polypeptide linker sequence. In these and other embodiments, the binding domain specifically binds to one or more molecules comprising: programmed death ligand 1 (PD-L1), programmed death 1 (PD-1), cytotoxic T-lymphocyte associated protein 4 (CTLA-4), cluster of differentiation 33 (CD33), cluster of differentiation 47 (CD47), glucocorticoid-induced tumor necrosis factor receptor (TNFR) family related gene (GITR), lymphocyte function-associated antigen 1 (LFA-1), tissue factor (TF), delta-like protein 4 (DLL4), single strand DNA or T-cell immunoglobulin and mucin-domain containing-3 (Tim-3). In certain embodiments, the binding domain specifically binds to one or more molecules comprising: programmed death ligand 1 (PD-L1). In these and other embodiments, the TGFβRII domain binds to transforming factor beta (TGFβ). In these and other embodiments, the first fusion protein complex is covalently linked to a second fusion protein complex by a disulfide bond linking the Fc domain of the first soluble fusion protein complex to the Fc domain of the second soluble fusion protein complex.

In certain embodiments, an isolated soluble fusion protein complex comprises at least two soluble proteins, wherein a first soluble protein comprises an interleukin-15 (IL-15) polypeptide domain and a second soluble protein comprises a soluble IL-15 receptor alpha sushi-binding domain (IL-15RαSu) fused to an immunoglobulin Fc domain, the first and/or second soluble protein further comprises a binding domain that specifically binds to a disease antigen, immune checkpoint molecule or immune signaling molecule, and the IL-15 domain of the first soluble protein binds to the IL-15Rα Su domain of the second soluble protein to form a soluble fusion protein complex. In certain embodiments, the immunoglobulin Fc (IgG Fc) domain further comprises a glycosylate or an aglycosylated transforming growth factor-beta receptor type 2 (TGFβRII) domain which is fused or linked to the IgG Fc domain via a linker molecule. In certain embodiments, the immunoglobulin Fc (IgG Fc) domain lacks the TGFβRII domain. In these and other embodiments, the immunoglobulin Fc domain is an IgG Fc variant comprising a hinge region lacking a free cysteine at residue position 70. In these and other embodiments, the cysteine is substituted with a serine at residue position 70 (IgG-FcC70S). In these and other embodiments, the immunoglobulin Fc domain is an IgG-Fc variant lacking a hinge region. In these and other embodiments, one of the first or second soluble protein further comprises a second binding domain that specifically binds to a disease antigen, immune checkpoint molecule, or immune signaling molecule. In these and other embodiments, the IL-15 polypeptide is an IL-15 variant comprising an N72D mutation (IL-15N72D), an IL-15K41Q mutation, an IL-15L45S mutation, an IL-15I67T mutation, an IL-15N79Y mutation, an IL-15E93A mutation or combinations thereof. In these and other embodiments, the binding domain comprises an immunoglobulin light chain variable domain covalently linked to an immunoglobulin heavy chain variable domain by a polypeptide linker sequence. In these and other embodiments, the binding domain specifically binds to one or more molecules comprising: programmed death ligand 1 (PD-L1), programmed death 1 (PD-1), cytotoxic T-lymphocyte associated protein 4 (CTLA-4), cluster of differentiation 33 (CD33), cluster of differentiation 47 (CD47), glucocorticoid-induced tumor necrosis factor receptor (TNFR) family related gene (GITR), lymphocyte function-associated antigen 1 (LFA-1), tissue factor (TF), delta-like protein 4 (DLL4), single strand DNA or T-cell immunoglobulin and mucin-domain containing-3 (Tim-3). In certain embodiments, the binding domain specifically binds to one or more molecules comprising: programmed death ligand 1 (PD-L1). In certain embodiments, the first fusion protein complex is covalently linked to a second fusion protein complex by a disulfide bond linking the Fc domain of the first soluble fusion protein complex to the Fc domain of the second soluble fusion protein complex.

In certain embodiments, the binding domain comprises a single chain antibody (scAb or scFv) wherein an immunoglobulin light chain variable domain is covalently linked to an immunoglobulin heavy chain variable domain by a polypeptide linker sequence. Alternatively, the binding domain comprises a soluble or extracellular ligand or receptor domain capable of acting as an immune checkpoint inhibitor or immune agonist.

Exemplary polynucleotide molecules comprise nucleic acid sequences comprising SEQ ID NOS: 1, 3, 5, 7, 9, 11, 13, 15, 16, 17, 18, 19 or combinations thereof. In one aspect, the nucleic acid sequence(s) further comprises a promoter, translation initiation signal, and leader sequence operably linked to the sequence encoding the fusion protein. In certain embodiments, an expression vector comprises a nucleic acid sequence comprising SEQ ID NOS: 1, 3, 5, 7, 9, 11, 13, 15, 16, 17, 18, 19 or combinations thereof.

Exemplary polypeptide molecules comprise amino acid sequences comprising SEQ ID NOS: 2, 4, 6, 8, 10, 12, 14, 20, 21, 22, 23, 24 or 46, 25, 26, 27, 28, 29, 30, 31, 32, 33, 34 or combinations thereof.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 1.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 3.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 5.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 7.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 9.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 11.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 13.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 15.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 16.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 17.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 18.

In some embodiments, the isolated soluble fusion protein complexes are encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 19.

Also provided are expression vector(s) comprising the nucleic acid sequences described herein. For example, the nucleic acid sequence is in a vector for replication, expression, or both.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 2.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 4.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 6.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 8.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 10.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 12.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 14.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 20.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 21.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 22.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 23.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 24 or 46.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 25.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 26.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 27.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 28.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 29.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 302.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 31.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 32.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 33.

In some embodiments, the isolated soluble fusion protein complexes comprise an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 34.

Also provided is a soluble fusion protein complex comprising a first soluble fusion protein complex covalently linked to a second soluble fusion protein complex. For example, the soluble fusion protein complexes of the invention are multimerized, e.g., dimerized, trimerized, or otherwise multimerized (e.g., 4 complexes, 5 complexes, etc.). For example, the multimers are homomultimers or heteromultimers. The soluble fusion protein complexes are joined by covalent bonds, e.g., disulfide bonds, chemical cross-linking agents. In some cases, one soluble fusion protein is covalently linked to another soluble fusion protein by a disulfide bond linking the Fc domain of the first soluble protein to the Fc domain of the second soluble protein.

The Fc domain or functional fragment thereof includes an Fc domain selected from the group consisting of IgG Fc domain, human IgG1 Fc domain, human IgG2 Fc domain, human IgG3 Fc domain, human IgG4 Fc domain, IgA Fc domain, IgD Fc domain, IgE Fc domain, and IgM Fc domain; mouse IgG2A domain, or any combination thereof. Optionally, the Fc domain includes an amino acid change that results in an Fc domain with altered complement or Fc receptor binding properties or altered dimerization or glycosylation profiles. Amino acid changes to produce an Fc domain with altered complement or Fc receptor binding properties or altered dimerization or glycosylation profiles are known in the art. For example, a substitution of leucine residues at positions 234 and 235 of the IgG1 CH2 (numbering based on antibody consensus sequence) (i.e., . . . P E L L G G . . . (SEQ ID NO: 41) with alanine residues (i.e., . . . P E A A G G . . . (SEQ ID NO: 42) results in a loss of Fc gamma receptor binding, whereas the substitution of the lysine residue at position 322 of the IgG1 CH2 (numbering based on antibody consensus sequence) (i.e., . . . K C K S L . . . (SEQ ID NO: 43) with an alanine residue (i.e., . . . K C A S L . . . (SEQ ID NO: 44) results in a loss of complement activation. In some examples, such mutations are combined.

In some aspects, the binding domain and/or the cytokine receptor domain are covalently linked to an IL-15 polypeptide (or functional fragment thereof) by a polypeptide linker sequence. Similarly, the binding domain and/or the cytokine receptor domain are covalently linked to an IL-15Rα polypeptide (or functional fragment thereof) by polypeptide linker sequence. Optionally, the IL-15Rα polypeptide (or functional fragment thereof) is covalently linked to the Fc domain (or functional fragment thereof) by polypeptide linker sequence. Each polypeptide linker sequence can be selected independently. Optionally, the polypeptide linker sequences are the same. Alternatively, they are different.

Optionally, the soluble fusion protein complexes of the invention are provided wherein at least one of the soluble fusion proteins comprise a detectable label. Detectable labels include, but are not limited to, biotin, streptavidin, an enzyme, or catalytically active fragment thereof, a radionuclide, a nanoparticle, a paramagnetic metal ion, or a fluorescent, phosphorescent, or chemiluminescent molecule, or any combination thereof.

The invention provides method for making the soluble fusion protein complexes of the invention. The method includes the steps of: a) introducing into a first host cell a DNA vector with appropriate control sequences encoding the first protein, b) culturing the first host cell in media under conditions sufficient to express the first protein in the cell or the media; c) purifying the first protein from the host cells or media, d) introducing into a second host cell a DNA vector with appropriate control sequences encoding the second protein, e) culturing the second host cell in media under conditions sufficient to express the second protein in the cell or the media; and f) purifying the second protein from the host cells or media, and g) mixing the first and second proteins under conditions sufficient to allow binding between IL-15 domain of a first protein and the soluble IL-15Rα domain of a second protein to form the soluble fusion protein complex.

In some cases, the method further includes mixing the first and second protein under conditions sufficient to allow formation of a disulfide bond between the polypeptides expressed from the expression vectors.

Alternatively, methods for making soluble fusion protein complexes of the invention are carried out by a) introducing into a host cell a DNA vector with appropriate control sequences encoding the first protein and a DNA vector with appropriate control sequences encoding the second protein, b) culturing the host cell in media under conditions sufficient to express the proteins in the cell or the media and allow association between IL-15 domain of a first protein and the soluble IL-15Rα domain of a second protein to form the soluble fusion protein complex; and c) purifying the soluble fusion protein complex from the host cells or media.

In one aspect, the method further includes mixing the first and second protein under conditions sufficient to allow formation of a disulfide bond between the polypeptides expressed from the expression vectors.

Also provided are methods for making soluble fusion protein complexes comprising a) introducing into a host cell a DNA vector with appropriate control sequences encoding the first and second proteins, b) culturing the host cell in media under conditions sufficient to express the proteins in the cell or the media and allow association between IL-15 domain of a first protein and the soluble IL-15Rα domain of a second protein to form the soluble fusion protein complex, and to allow formation of a disulfide bond between the polypeptides; and c) purifying the soluble fusion protein complex from the host cells or media.

Optionally, the method further includes mixing the first and second protein under conditions sufficient to allow formation of a disulfide bond between the polypeptides expressed from the expression vectors.

Methods for treating a neoplasia, infectious disease, or autoimmune disease in a subject in need thereof are carried out by administering to a subject an effective amount of a pharmaceutical composition comprising a soluble fusion protein complex described herein, e.g., a soluble anti-PD-L1 scAb/IL-15N72D:TGFβRII/IL-15RαSu/Fc fusion protein complex, thereby treating the neoplasia, infectious disease, or autoimmune disease. For example, methods for treating solid or hematological malignancies in a subject in need thereof are carried out by administering to a subject an effective amount of a pharmaceutical composition comprising a soluble TGFβRII dimer/huIL-15N72D:anti-human PD-L1 scAb/huIL-15RαSu/huIgG1 Fc fusion protein complex, thereby treating the malignancy.

Suitable neoplasias for treatment with the methods described herein include a glioblastoma, prostate cancer, acute myeloid leukemia, B-cell neoplasm, multiple myeloma, B-cell lymphoma, B cell non-Hodgkin's lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, prostate cancer, pancreatic cancer, colorectal cancer, ovarian cancer, non-small cell lung carcinoma, and squamous cell head and neck carcinoma.

The pharmaceutical composition comprising a fusion protein complex is administered in an effective amount. For example, an effective amount of the pharmaceutical composition is between about 1 µg/kg and 100 µg/kg, e.g., 1, 5, 10, 15, 20, 25, 30, 35, 40, 45, 50, 55, 60, 65, 70, 75, 80, 85, 90, 95, or 100 µg/kg. Alternatively, TxM complex is administered as a fixed dose or based on body surface area (i.e., per $m^2$).

The pharmaceutical composition comprising the fusion protein complex is administered at least one time per month, e.g., twice per month, once per week, twice per week, once per day, twice per day, every 8 hours, every 4 hours, every 2 hours, or every hour. Suitable modes of administration for the pharmaceutical composition include systemic administration, intravenous administration, local administration, subcutaneous administration, intramuscular administration, intratumoral administration, inhalation, and intraperitoneal administration.

Preferably, the fusion protein complex increases serum levels of interferon gamma (IFN-γ), and/or stimulates $CD4^+$ and $CD8^+$ T cells and NK cells to kill diseased cells or tumor cells in a subject.

In certain embodiments, a method of inducing antibody-dependent cell-mediated cytotoxicity (ADCC) or antibody-dependent cell-mediated phagocytosis (ADCP) in a subject in need thereof is provided for, comprising administering to a subject in need thereof, an effective amount of a soluble fusion protein complex embodied herein.

In certain embodiments, a method of inhibiting transforming growth factor beta (TGFβ) activity in vitro or in vivo, comprising contacting a TGFβ-responsive cell in vitro or administering to a subject in need thereof, an effective amount of a soluble fusion protein complex embodied herein.

In certain embodiments, a method of decreasing the amount of transforming growth factor beta (TGFβ) in vivo, comprising administering to a subject in need thereof, an effective amount of a soluble fusion protein complex embodied herein.

In certain embodiments, a method of inhibiting transforming growth factor beta (TGFβ) mediated phosphorylation and activation of SMAD polypeptides in vivo, comprising administering to a subject in need thereof, a therapeutically effective amount of a soluble fusion protein complex embodied herein.

In certain aspects of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt), and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15/IL-2 βγc receptors (IL-15R) compared to the native IL-15 polypeptide. Alternatively, the IL-15 variant functions as an IL-15 antagonist as demonstrated by e.g., decreased binding activity for the IL-15R compared to the native IL-15 polypeptide.

Methods for killing a target cell are carried out by a) contacting a plurality of cells with a soluble fusion protein complex of the invention, wherein the plurality of cells further include immune cells bearing the IL-15R chains recognized by the IL-15 domain, or immune cells bearing checkpoint and/or cytokine receptors or signaling molecules modulated by the checkpoint inhibitor, TGFβ molecules or immune agonist binding domains, and the target disease cells; b) activating the immune cells via the IL-15R or signaling molecules, via inhibiting TGFβ immunosuppression or via blockade of the checkpoint molecules; and c) killing the target disease cells by the activated immune cells. For example, the target disease cells are tumor cells, autoimmune cells, or virally infected cells. In some cases, the binding domain comprises an anti-PD-L1 antibody.

Methods for killing a target cell further comprise a) contacting a plurality of cells with a soluble fusion protein complex of the invention, wherein the plurality of cells further include immune cells bearing Fc receptor chains recognized by the Fc domain, and the target disease cells bearing an antigen recognized by binding domain such as an antigen-specific scab and/or a immunostimulatory cytokines or receptors thereof; b) forming a specific binding complex (bridge) between the antigen on the target disease cells and Fc receptor chains on the immune cells and an immunostimulatory cytokines or receptors thereof sufficient to bind and activate the immune cells; and c) killing the target disease cells by the bound activated immune cells. For example, the target disease cells are tumor cells, autoimmune cells, or virally infected cells. In some cases, the binding domain comprises an anti-PD-L1 antibody.

Also provided are methods for preventing or treating disease in a patient, the method including the steps of: a) administering to the patient a soluble fusion protein complex of the invention; b) activating the immune cells in the patient; and c) damaging or killing the disease cells via the activated immune cells sufficient to prevent or treat the disease in the patient.

The invention also provides methods for preventing or treating disease in a patient in the method including the steps of: a) mixing immune cells bearing IL-15R chains, cytokine receptors and/or checkpoint or signaling molecules with a soluble fusion protein complex of the invention; b) activating the immune cells; c) administering to the patient the activated immune cells; and d) damaging or killing the disease cells via the activated immune cells sufficient to prevent or treat the disease in the patient. The immune cells can also be contacted with specific antigen to expand the number of activated immune cells.

Administration of the fusion protein complexes of the invention induces an immune response in a subject. For example, administration of the fusion protein complexes of the invention induces an immune response against cells associated with neoplasia, infectious disease, or autoimmune disease. In one aspect, the fusion protein complex of the invention increases immune cell proliferation.

The invention provides methods of stimulating immune responses in a mammal by administering to the mammal an effective amount of the soluble fusion protein complex of the invention. The invention also provides methods of suppressing immune responses in a mammal by administering to the mammal an effective amount of the soluble fusion protein complex of any one of the invention.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, or small compound.

By "TxM" is meant a complex comprising an IL-15N72D:IL-15RαSu/Fc scaffold linked to a binding domain. An exemplary TxM is an IL-15N72D:IL-15RαSu/Fc complex comprising a fusion to a binding domain that specifically recognizes PD-L1 (PD-L1 TxM).

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The term "binding domain" is intended to encompass an antibody, single chain antibody, Fab, Fv, T-cell receptor binding domain, ligand binding domain, receptor binding domain, or other antigen-specific polypeptides known in the art.

The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. F(ab')$_2$, Fab', Fab, Fv) capable of binding the epitope, antigen, or antigenic fragment of interest.

By "binding to" a molecule is meant having a physico-chemical affinity for that molecule.

"Detect" refers to identifying the presence, absence, or amount of the analyte to be detected.

By "disease" is meant any condition or disorder that damages or interferes with the normal function of a cell, tissue, or organ. Examples of diseases include neoplasias, autoimmune diseases and viral infections.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full-length polypeptides and nucleic acid, respectively. A nucleic acid fragment of almost any length is employed. For example, illustrative polynucleotide segments with total lengths of about 10,000, about 5,000, about 3,000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The terms "isolated", "purified", or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In particular embodiments, the neoplasia is multiple myeloma, beta-cell lymphoma, urothelial/bladder carcinoma, or melanoma. As used herein, "obtaining" as in "obtaining an agent" includes synthesizing, purchasing, or otherwise acquiring the agent.

By "reduces" is meant a negative alteration of at least 5%, 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequencher, Gene Codes Corporation, 775 Technology Drive, Ann Arbor, Mich.; Vector NTI, Life Technologies, 3175 Staley Rd. Grand Island, N.Y.). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline. The subject is preferably a mammal in need of such treatment, e.g., a subject that has been diagnosed with B cell lymphoma or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to affect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition, or symptoms associated therewith be completely eliminated.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference.

Genbank and NCBI submissions indicated by accession number cited herein are incorporated herein by reference. All other published references, documents, manuscripts, and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 28A:
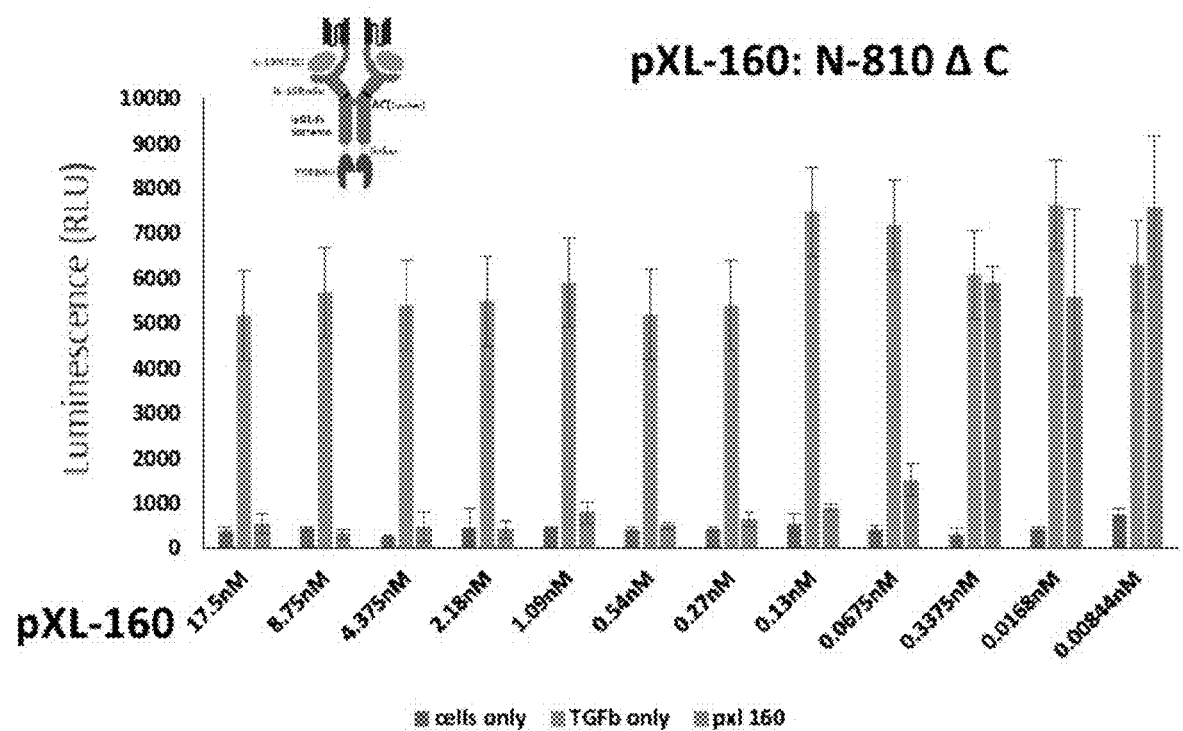
Figure 28B:
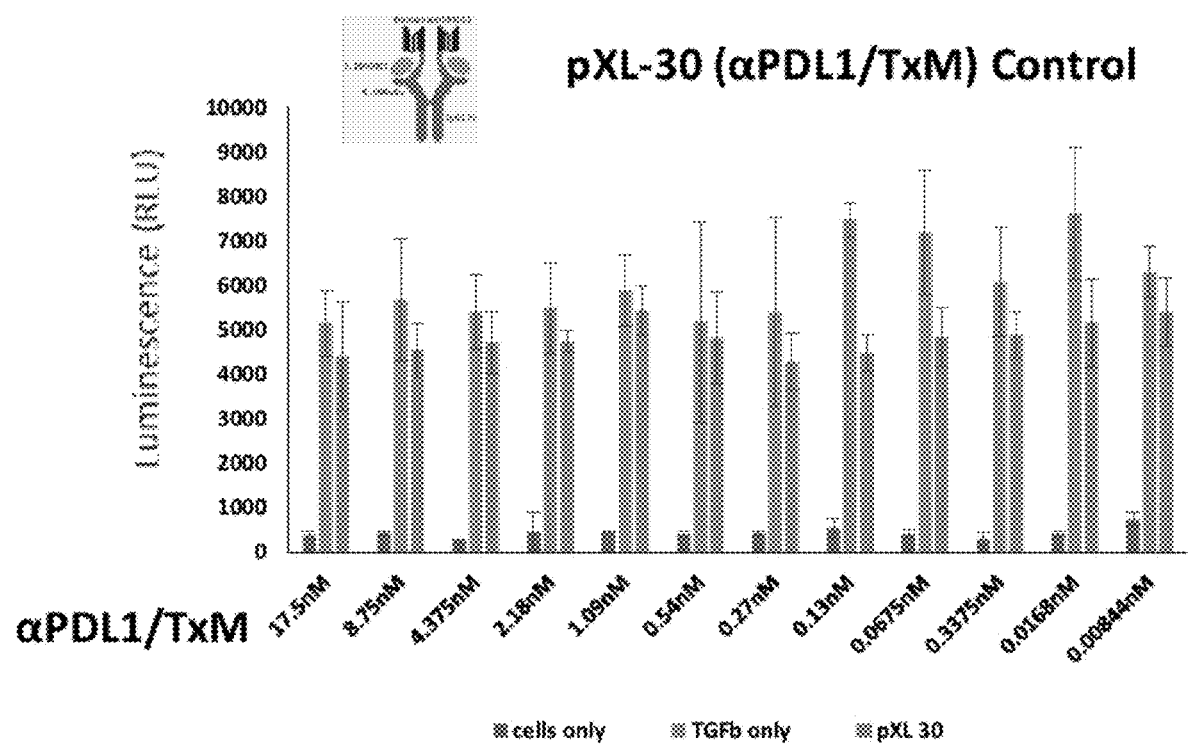

FIGS. 28A and 28B are graphs demonstrating specific hTGFβ1 blocking activity for each molecule (N-810 Δ C, FIG. 28A) compared against the activity of the parental control molecule (αPDL1/TxM, FIG. 28B). A stable cellular luciferase-based reporter system (HEK-293T-luc2P/SBE) was used in order to assess the specific TGFβ-blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.

Figure 29A:
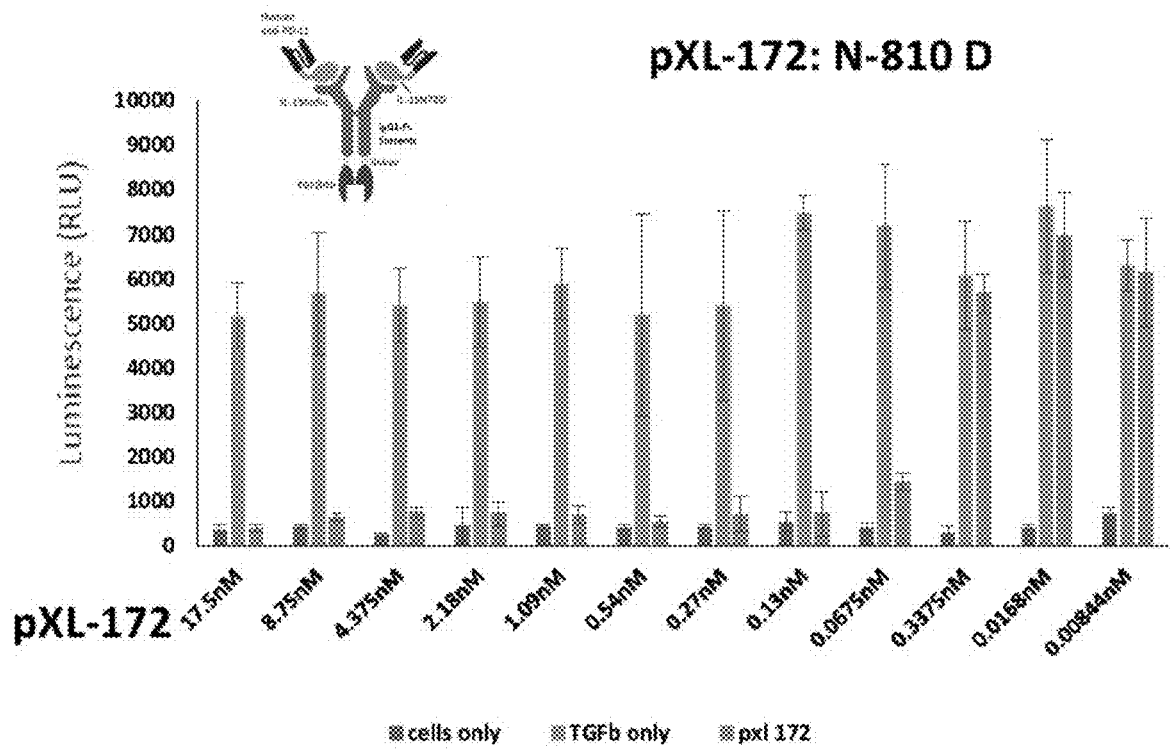
Figure 29B:
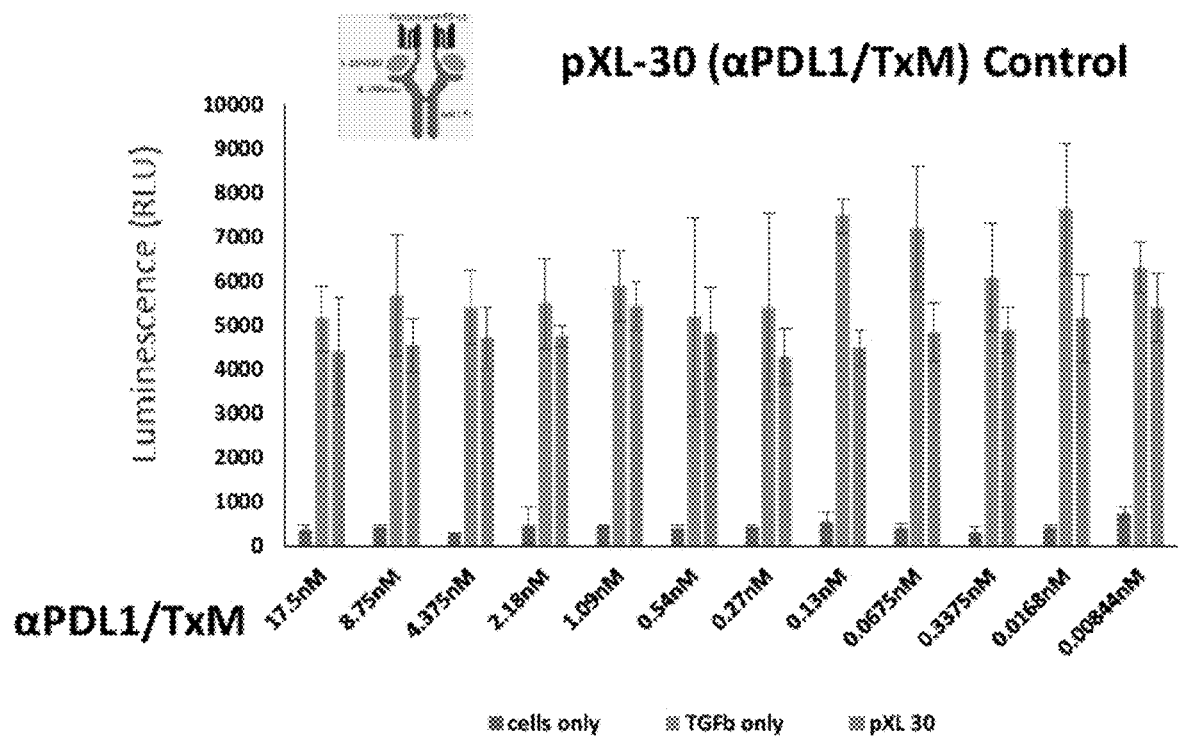

FIGS. 29A and 29B are graphs demonstrating specific hTGFβ1 blocking activity for each molecule (N-810D, FIG. 29A) compared against the activity of the parental control molecule (αPDL1/TxM, FIG. 29B). A stable cellular luciferase-based reporter system (HEK-293T-luc2P/SBE) was used in order to assess the specific TGFβ-blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.

Figure 30:
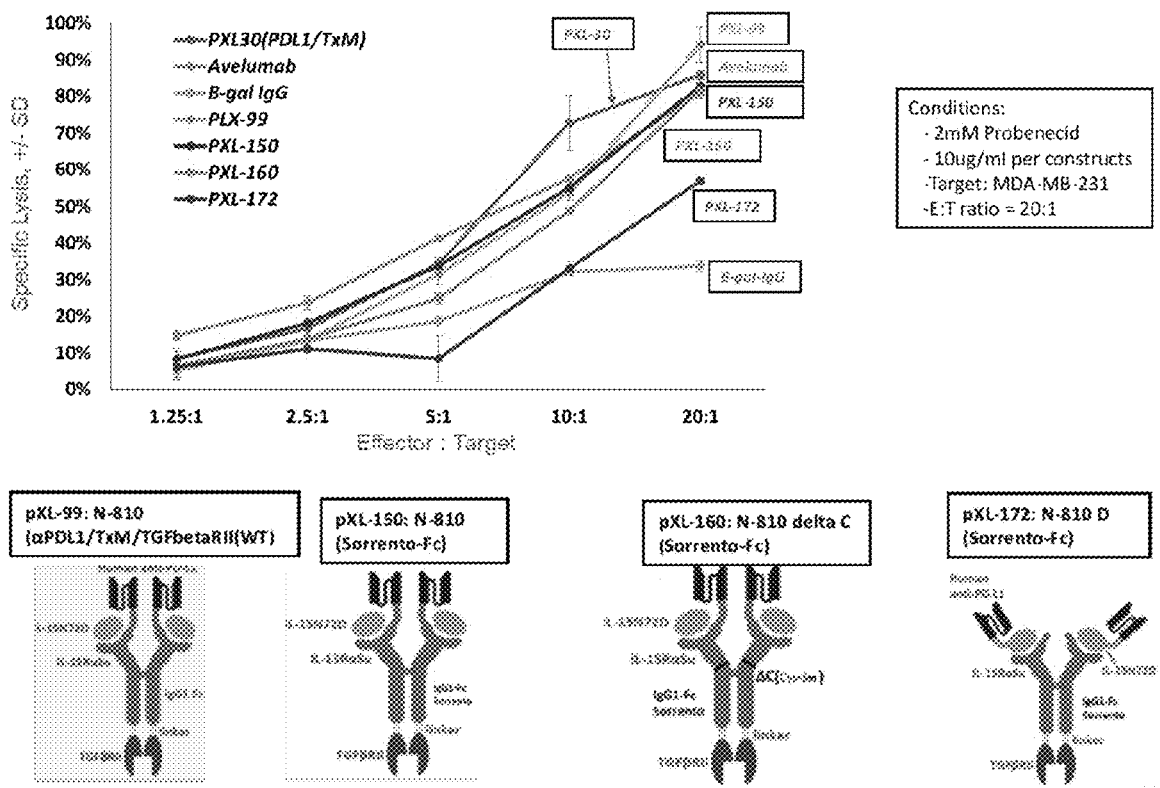

FIG. 30 is a graph demonstrating the antibody-dependent cellular cytotoxicity (ADCC) of the TxM constructs in mammary adenocarcinoma cells (MDA-MB-231). Antibody-Dependent Cellular Cytotoxicity (ADCC) was used in order to determine the specific αPD-L1 activity. Effector cells: haNK (NK-92 derivative).

Figure 31A:
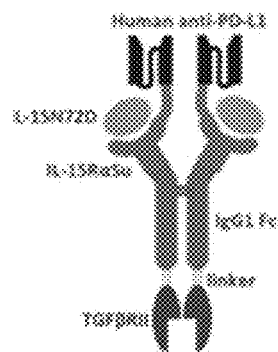
Figure 31B:
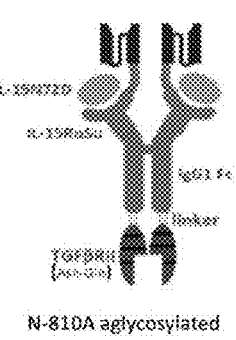
Figure 31C:
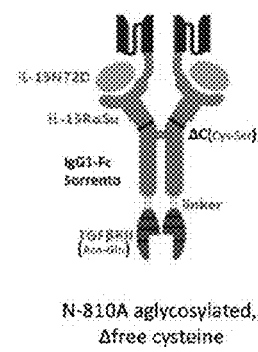
Figure 31D:
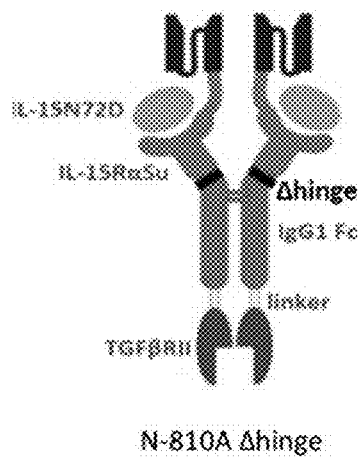
Figure 31E:
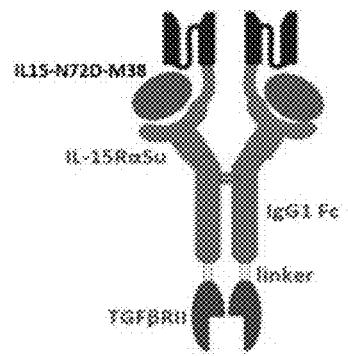
Figure 31F:
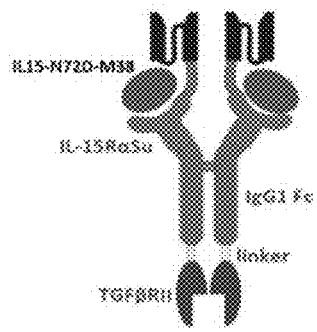
Figure 31G:
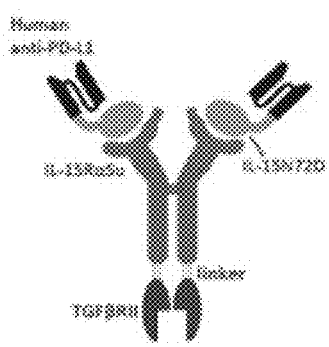
Figure 31H:
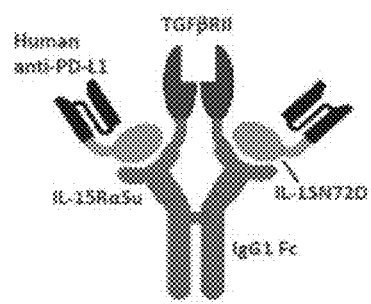

FIGS. 31A-31H are schematic representations showing the various constructs. FIG. 31A: N-810A. FIG. 31B: N-810A aglycosylated. FIG. 31C: N-810A aglycosylated, Δ free cysteine. FIG. 31D: N-810A Δ hinge. FIG. 31E: N-810A (IL15-K41Q, L45S, I67T, N79Y, E93A). The mutations in IL15 enhance the solubility and expression of the molecule. FIG. 31F: N-810A (IL15-L45S). The mutations in IL15 enhance solubility and expression of the molecule. FIG. 31G: N-810D. FIG. 31H: N-810E.

FIG. 32 is a table demonstrating that IL15 mutations increase protein yield and decrease aggregation. N-810D variation also increases yield and decreases aggregation.

DETAILED DESCRIPTION

The invention is based, at least in part, on the surprising discovery that multi-specific IL-15-based protein complexes enhance the activity of immune cells and promote their activity against disease cells, thereby resulting in reduction or prevention of disease. These protein complexes also show increased binding to disease and target antigens. Provided herein are multi-specific protein complexes with one domain comprising IL-15 or a functional variant, a cytokine receptor or cytokine ligand, and a binding domain comprising a disease-specific binding domain, immune checkpoint inhibitor or immune agonist. Such protein complexes have utility in methods for treating a neoplasia, infectious disease, or autoimmune disease in a subject. Thus, provided herein are compositions featuring PD-L1/TGFβRII/TxM and methods of using such compositions to enhance an immune response against a neoplasia (e.g., solid and hematologic tumors).

As described herein, the use of proteins with the capability of targeting diseased cells for host immune recognition and response is an effective strategy for treating cancer, infectious diseases, and autoimmune diseases. As described in U.S. Pat. No. 8,507,222 (incorporated herein by reference), a protein scaffold comprising IL-15 and IL-15 receptor α domains has been used to generate multi-specific proteins capable of recognizing antigens on disease cells and receptors on immune cells. See, U.S. Pat. No. 8,507,222 at Example 15. Described herein is the generation of soluble multi-specific protein complexes comprising IL-15 and IL-15 receptor α linked to one or more binding domains recognizing immune checkpoint or signaling molecules. In some cases, these complexes also comprise binding domains that recognize antigens, such as PD-L1, ssDNA, CD20, HER2, EGFR, CD19, CD38, CD52, GD2, CD33, Notch1, intercellular adhesion molecule 1 (ICAM-1), tissue factor, HIV envelope or other tumor antigens, expressed on disease cells.

In some cases, the binding domain comprises a single chain antibody wherein an immunoglobulin light chain variable domain covalently linked to an immunoglobulin heavy chain variable domain by a polypeptide linker sequence. The single chain antibody domain can be arranged in either the VH-linker-VL or VL-linker-VH format. Alternatively, the binding domain comprises a soluble or extracellular ligand or receptor domain capable of acting as an immune checkpoint inhibitor or immune agonist. The binding domains recognizing an immune checkpoint or signaling molecule are linked to either the N- or C-termini of the IL-15 or IL-15 receptor α proteins with or without an additional linker sequence so long as binding activity is maintained. Preferably, the binding domain is linked to the N-terminus of the human IL-15N72D superagonist protein (huIL-15N72D). Alternatively, the binding domain is linked to the C-terminus of the human IL-15N72D protein. Preferably, the binding domain is linked to the N-terminus of the human IL-15 receptor α sushi domain (huIL-15RαSu). Alternatively, the binding domain is linked to the C-terminus of the huIL-15RαSuFc protein. In some cases, the multi-specific protein complexes of the invention further comprise an IgG Fc domain for protein dimerization and recognition of CD16 receptors on immune cells. Such a domain mediates stimulation of antibody-dependent cellular cytotoxicity (ADCC), antibody-dependent cellular phagocytosis (ADCP) and complement-dependent cytotoxicity (CDC) against target cells. In some examples, it is useful to employ Fc domains with enhanced or decreased CD16 binding activity. In one aspect, the Fc domain contains amino acid substitutions L234A and L235A (LALA) (number based on Fc consensus sequence) that reduce ADCC activity, but retain the ability to form disulfide-bound dimers.

Accordingly, in certain embodiments, an isolated soluble fusion protein complex comprises at least two soluble protein complexes, a first soluble protein complex comprises an interleukin-15 (IL-15) polypeptide domain and a second soluble protein comprises a soluble IL-15 receptor alpha sushi-binding domain (IL-15RαSu) fused to an immunoglobulin Fc domain, wherein the immunoglobulin Fc domain is fused or linked to a transforming growth factor-beta receptor type 2 (TGFβRII) domain; the first and/or second soluble protein further comprises a binding domain that specifically binds to a disease antigen, immune checkpoint molecule or immune signaling molecule, and the IL-15 domain of the first soluble protein binds to the IL-15RαSu domain of the second soluble protein to form a soluble fusion protein complex. In certain aspects, the immunoglobulin Fc domain is linked to a transforming growth factor-beta receptor type 2 (TGFβRII) domain via a linker molecule.

In certain embodiments, a soluble fusion complex comprises at least two soluble proteins a first fusion protein and a second fusion protein, wherein the first fusion protein comprises a transforming growth factor-beta receptor type 2 (TGFβRII) dimer comprising a first TGFβRII domain linked to a second TGFβRII domain wherein the TGFβRII dimer is fused or linked to an interleukin-15 (IL-15) polypeptide domain; the second fusion protein comprises a soluble IL-15 receptor alpha sushi-binding domain (IL-15RαSu) fused to an immunoglobulin Fc domain; wherein the second fusion protein further comprises a binding domain that specifically binds to a disease antigen, immune checkpoint molecule or immune signaling molecule, and wherein the IL-15 domain of the first fusion protein binds to the IL-15RαSu domain of the second fusion protein to form a soluble fusion protein complex.

In certain embodiments, a soluble fusion complex comprises at least two soluble proteins a first fusion protein and a second fusion protein, wherein the first fusion protein comprises an interleukin-15 (IL-15) polypeptide domain fused to a binding domain that specifically binds to a disease antigen, immune checkpoint molecule or immune signaling molecule; the second fusion protein comprises a transforming growth factor-beta receptor type 2 (TGFβRII) dimer comprising a first TGFβRII domain linked to a second TGFβRII domain wherein the TGFβRII dimer and a soluble IL-15 receptor alpha sushi-binding domain (IL-15RαSu) fused to an immunoglobulin Fc domain; wherein the first or second TGFβRII domain is fused to the IL-15RαSu domain wherein the IL-15 polypeptide domain of the first fusion protein binds to the IL-15RαSu domain of the second fusion protein to form a soluble fusion protein complex.

In certain embodiments, one of the first or second soluble protein further comprises a second binding domain that specifically binds to a disease antigen, immune checkpoint molecule, or immune signaling molecule.

In certain embodiments, the IL-15 polypeptide is an IL-15 variant comprising an N72D mutation (IL-15N72D).

In certain embodiments, the binding domain comprises an immunoglobulin light chain variable domain covalently linked to an immunoglobulin heavy chain variable domain by a polypeptide linker sequence.

In certain embodiments, the binding domain specifically binds to one or more molecules comprising: programmed death ligand 1 (PD-L1), programmed death 1 (PD-1), cytotoxic T-lymphocyte associated protein 4 (CTLA-4), cluster of differentiation 33 (CD33), cluster of differentiation 47 (CD47), glucocorticoid-induced tumor necrosis factor receptor (TNFR) family related gene (GITR), lymphocyte function-associated antigen 1 (LFA-1), tissue factor (TF), delta-like protein 4 (DLL4), single strand DNA or T-cell immunoglobulin and mucin-domain containing-3 (Tim-3).

In certain embodiments, the binding domain specifically binds to one or more molecules comprising: programmed death ligand 1 (PD-L1). In certain embodiments, the TGFβRII domain binds to transforming factor beta (TGFβ).

In certain embodiments, a first fusion protein complex is covalently linked to a second fusion protein complex by a disulfide bond linking the Fc domain of the first soluble fusion protein complex to the Fc domain of the second soluble fusion protein complex.

Interleukin-15

Interleukin-15 (IL-15) is an important cytokine for the development, proliferation, and activation of effector NK cells and CD8$^+$ memory T cells. IL-15 binds to the IL-15 receptor α (IL-15Rα) and is presented in trans to the IL-2/IL-15 receptor β-common γ chain (IL-15Rβγ$_c$) complex on effector cells. IL-15 and IL-2 share binding to the IL-15Rβγ$_c$, and signal through STAT3 and STAT5 pathways.

However, unlike IL-2, IL-15 does not support maintenance of CD4$^+$CD25$^+$FoxP3$^+$ regulatory T (Treg) cells or induce cell death of activated CD8$^+$ T cells, effects that may have limited the therapeutic activity of IL-2 against multiple myeloma. Additionally, IL-15 is the only cytokine known to provide anti-apoptotic signaling to effector CD8$^+$ T cells. IL-15, either administered alone or as a complex with the IL-15Rα, exhibits potent anti-tumor activities against well-established solid tumors in experimental animal models and, thus, has been identified as one of the most promising immunotherapeutic drugs that could potentially cure cancer. A first-in-human clinical trial found that patients administered recombinant human (rh)IL-15 showed significant increases in γδ T cells, CD8$^+$ T cells, and NK cells, but the high doses resulted in toxicities and limited tumor responses.[2] A relatively short half-life of the prokaryotic rhIL-15 was also observed.[23]

To facilitate clinical development of an IL-15-based cancer therapeutic, an IL-15 mutant (IL-15N72D) with increased biological activity compared to IL-15 was identified (Zhu et al., J Immunol, 183: 3598-3607, 2009). The pharmacokinetics and biological activity of this IL-15 superagonist (IL-15N72D) was further improved by the creation of IL-15N72D:IL-15Rα/Fc fusion complex (ALT-803), such that the super agonist complex has at least 25-times the activity of the native cytokine in vivo (Han et al., Cytokine, 56: 804-810, 2011).

Immune Checkpoint Inhibitor and Immune Agonist Domains

In other embodiments, the binding domain is specific to an immune checkpoint or signaling molecule or its ligand and acts as an inhibitor of immune checkpoint suppressive activity or as an agonist of immune stimulatory activity. Such immune checkpoint and signaling molecules and ligands include PD-1, PD-L1, PD-L2, CTLA-4, CD28, CD80, CD86, B7-H3, B7-H4, B7-HS, ICOS-L, ICOS, BTLA, CD137L, CD137, HVEM, KIR, 4-1BB, OX40L, CD70, CD27, CD47, CIS, OX40, GITR, IDO, TIM3, GAL9, VISTA, CD155, TIGIT, LIGHT, LAIR-1, Siglecs and A2aR (Pardoll D M. 2012. Nature Rev Cancer 12:252-264, Thaventhiran T, et al. 2012. J Clin Cell Immunol S 12:004). Additionally, preferred antibody domains of the invention may include ipilimumab and/or tremelimumab (anti-CTLA4), nivolumab, pembrolizumab, pidilizumab, TSR-042, ANB011, AMP-514 and AMP-224 (a ligand-Fc fusion) (anti-PD1), atezolizumab (MPDL3280A), avelumab (MSB0010718C), durvalumab (MEDI4736), MEDI0680, and BMS-9365569 (anti-PDL1), MEDI6469 (anti-OX40 agonist), BMS-986016, IMP701, IMP731, IMP321 (anti-LAG3) and GITR ligand.

Cytokine Receptors and Cytokines

Cytokine receptors which are fused or linked to the IL-15 molecules embodied herein bind to immunostimulatory cytokines which result in the augmentation of immune activity. Examples of cytokines include but are not limited to the IL-2 family, interferon (IFN), IL-10, IL-1, IL-17, TGF and TNF cytokine families, and to IL-1 through IL-35, IFN-α, IFN-β, IFNγ, TGF-β, TNF-α, and TNFβ. An exemplary receptor is the transforming growth factor beta receptor II (TGFβRII) which binds to TGFβ. The protein encoded by this gene is a transmembrane protein that has a protein kinase domain, forms a heterodimeric complex with TGF-beta receptor type-1, and binds TGF-beta. This receptor/ligand complex phosphorylates proteins, which then enter the nucleus and regulate the transcription of genes related to cell proliferation, cell cycle arrest, wound healing, immunosuppression, and tumorigenesis. Mutations in this gene have been associated with Marfan Syndrome, Loeys-Deitz Aortic Aneurysm Syndrome, and the development of various types of tumors. The extracellular domain of TGFβRII can bind to TGF-3 and block its activity. Within the tumor microenvironment, TGF-β acts to promote tumor progression via stromal modification, angiogenesis, and induction of epithelial-mesenchymal transition (EMT). TGF-β1 can directly suppress T cell proliferation and responses and natural killer (NK) cell activity. Moreover, TGF-β signaling in myeloid cells is critical in driving metastasis.

Antigen-Specific Binding Domains

Antigen-specific binding domains consist of polypeptides that specifically bind to targets on diseased cells. Alternatively, these domains may bind to targets on other cells that support the diseased state, such as targets on stromal cells that support tumor growth or targets on immune cells that support disease-mediated immunosuppression. Antigen-specific binding domains include antibodies, single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins (Weidle, U H, et al. 2013. Cancer Genomics & Proteomics 10: 155-168)) known in the art.

In certain embodiments, the antigen for the antigen-specific binding domain comprises a cell surface receptor or ligand. In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

Preferably, the antigen-specific binding domain is capable of binding to an antigen on a tumor cell. Tumor-specific binding domain may be derived from antibodies approved for treatment of patients with cancer include rituximab, ofatumumab, and obinutuzumab (anti-CD20 Abs); trastuzumab and pertuzumab (anti-HER2 Abs); cetuximab and panitumumab (anti-EGFR Abs); and alemtuzumab (anti-CD52 Ab). Similarly, binding domains from approved antibody-effector molecule conjugates specific to CD20 ($^{90}$Y-labeled ibritumomab tiuxetan, $^{131}$I-labeled tositumomab), HER2 (ado-trastuzumab emtansine), CD30 (brentuximab vedotin) and CD33 (gemtuzumab ozogamicin) (Sliwkowski M X, Mellman I. 2013 Science 341:1192) could be used.

Additionally, preferred binding domains of the invention may include various other tumor-specific antibody domains known in the art. The antibodies and their respective targets for treatment of cancer include but are not limited to nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti-CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxorubicin immunoconjugate (anti-Lewis-Y antigen), CC49 (anti-TAG-72), cedelizumab (anti-CD4), Ch. 14.18 (anti-GD2), ch-TNT (anti-DNA associated antigens), citatuzumab bogatox (anti-EpCAM), cixutumumab (anti-IGF-1 receptor), clivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HER3), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-5AC), epitumomab cituxetan (anti-episialin), epratuzumab (anti-CD22), ertumaxomab (anti-HER2/neu, CD3), etaracizumab (anti-integrin avI33), faralimomab (anti-Interferon receptor), farletuzumab (anti-folate receptor 1), FBTAO5 (anti-CD20), ficlatuzumab (anti-HGF), figitumumab (anti-IGF-1 receptor), flanvotumab (anti-TYRP1(glycoprotein 75)), fresolimumab (anti-TGF J3), futuximab (anti-EGFR), galiximab (anti-CD80), ganitumab (anti-IGF-I), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), IMAB362 (anti-CLDN18.2), IMC-CS4 (anti-CSF1R), IMC-TR1 (TGFβRII), imgatuzumab (anti-EGFR), inclacumab (anti-selectin P), indatuximab ravtansine (anti-SDC1), inotuzumab ozogamicin (anti-CD22), intetumumab (anti-CD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (anti-PDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor α-chain), milatuzumab (anti-CD74), minretumomab (anti-TAG-72), mitumomab (anti-GD3 ganglioside), mogamulizumab (anti-CCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-Rα), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MUC1), parsatuzumab (anti-EGFL7), pascolizumab (anti-IL-4), patritumab (anti-HER3), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO 131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-FAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vantictumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (anti-integrin a5131), vorsetuzumab mafodotin (anti-CD70), votumumab (anti-tumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAPI), and GDC-0199 (anti-Bcl-2).

Other antibody domains or tumor target binding proteins useful in the invention (e.g. TCR domains) include, but are not limited to, those that bind the following antigens (note, the cancer indications indicated represent non-limiting examples): aminopeptidase N (CD13), annexin A1, B7-H3 (CD276, various cancers), CA125 (ovarian cancers), CA15-3 (carcinomas), CA19-9 (carcinomas), L6 (carcinomas), Lewis Y (carcinomas), Lewis X (carcinomas), alpha fetoprotein (carcinomas), CA242 (colorectal cancers), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma, B-cell neoplasmas, autoimmune diseases), CD21 (B-cell lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (metastatic melanoma, sarcoma), CD52 (leukemia), CD56 (small cell lung cancers, ovarian cancer, Merkel cell carcinoma, and the liquid tumor, multiple myeloma), CD66e (carcinomas), CD70 (metastatic renal cell carcinoma and non-Hodgkin lymphoma), CD74 (multiple myeloma), CD80 (lymphoma), CD98 (carcinomas), CD123 (leukemia), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (CEA, CD66e) (breast, colorectal and lung cancers), DLL4 (A-like-4), EGFR (various cancers), CTLA4 (melanoma), CXCR4 (CD 184, heme-oncology, solid tumors), Endoglin (CD 105, solid tumors), EPCAM (epithelial cell adhesion molecule, bladder, head, neck, colon, NHL prostate, and ovarian cancers), ERBB2 (lung, breast, prostate cancers), FCGR1 (autoimmune diseases), FOLR (folate receptor, ovarian cancers), FGFR (carcinomas), GD2 ganglioside (carcinomas), G-28 (a cell surface antigen glycolipid, melanoma), GD3 idiotype (carcinomas), heat shock proteins (carcinomas), HER1 (lung, stomach cancers), HER2 (breast, lung and ovarian cancers), HLA-DR10 (NHL), HLA-DRB (NHL, B cell leukemia), human chorionic gonadotropin (carcinomas), IGF1R (solid tumors, blood cancers), IL-2 receptor (T-cell leukemia and lymphomas), IL-6R (multiple myeloma, RA, Castleman's disease, IL6 dependent tumors), integrins ($\alpha v\beta 3$, $\alpha 5\beta 1$, $\alpha 6\beta 4$, $\alpha 11\beta 3$, $\alpha 5\beta 5$, $\alpha v\beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 (breast, ovarian, cervix, bronchus and gastrointestinal cancer), MUC16 (CA125) (ovarian cancers), CEA (colorectal cancer), gp100 (melanoma), MARTI (melanoma), MPG (melanoma), MS4A1 (membrane-spanning 4-domains subfamily A, small cell lung cancers, NHL), nucleolin, Neu oncogene product (carcinomas), P21 (carcinomas), nectin-4 (carcinomas), paratope of anti-(N-glycolylneuraminic acid, breast, melanoma cancers), PLAP-like testicular alkaline phosphatase (ovarian, testicular cancers), PSMA (prostate tumors), PSA (prostate), ROB04, TAG 72 (tumour associated glycoprotein 72, AML, gastric, colorectal, ovarian cancers), T cell transmembrane protein (cancers), Tie (CD202b), tissue factor, TNFRSF10B (tumor necrosis factor receptor superfamily member 10B, carcinomas), TNFRSF13B (tumor necrosis factor receptor superfamily member 13B, multiple myeloma, NHL, other cancers, RA and SLE), TPBG (trophoblast glycoprotein, renal cell carcinoma), TRAIL-R1 (tumor necrosis apoptosis inducing ligand receptor 1, lymphoma, NHL, colorectal, lung cancers), VCAM-1 (CD106, Melanoma), VEGF, VEGF-A, VEGF-2 (CD309) (various cancers). Some other tumor associated antigen targets have been reviewed (Gerber, et al, mAbs 2009 1:247-253; Novellino et al, Cancer Immunol Immunother. 2005 54:187-207, Franke, et al, Cancer Biother Radiopharm. 2000, 15:459-76, Guo, et al., Adv Cancer Res. 2013; 119: 421-475, Parmiani et al. J Immunol. 2007 178: 1975-9). Examples of these antigens include Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), annexin A1, nucleolin, endoglin (CD105), ROB04, amino-peptidase N, -like-4 (DLL4), VEGFR-2 (CD309), CXCR4 (CD184), Tie2, B7-H3, WT1, MUC1, LMP2, HPV E6 E7, EGFRvIII, HER-2/neu, idiotype, MAGE A3, p53 nonmutant, NY-ESO-1, GD2, CEA, MelanA/MART1, Ras mutant, gp100, p53 mutant, proteinase3 (PR1), bcr-abl, tyrosinase, survivin, hTERT, sarcoma translocation breakpoints, EphA2, PAP, ML-IAP, AFP, EpCAM, ERG (TMPRSS2 ETS fusion gene), NA17, PAX3, ALK, androgen receptor, cyclin B1, polysialic acid, MYCN, RhoC, TRP-2, GD3, fucosyl GM1, mesothelin, PSCA, MAGE A1, sLe(a), CYPIB I, PLAC1, GM3, BORIS, Tn, GloboH, ETV6-AML, NY-BR-1, RGS5, SART3, STn, carbonic anhydrase IX, PAX5, OY-TES 1, sperm protein 17, LCK, HMWMAA, AKAP-4, SSX2, XAGE 1, B7H3, legumain, Tie 2, Page4, VEGFR2, MAD-CT-1, FAP, PDGFR-P3, MAD-CT-2, Notch1, ICAM1 and Fos-related antigen 1.

Additionally, preferred binding domains of the invention include those specific to antigens and epitope targets associated with infected cells that are known in the art. Such targets include but are not limited those derived from the following infectious agents are of interest: HIV virus (particularly antigens derived from the HIV envelope spike and/or gp120 and gp41 epitopes), Human papilloma virus (HPV), *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum,* - *influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M arginini, Acholeplasma laidlawii, M. salivarium* and *M. pneumoniae.*

T-Cell Receptors (TCRs)

T-cells are a subgroup of cells which together with other immune cell types (polymorphonuclear cells, eosinophils, basophils, mast cells, B-cells, NK cells), constitute the cellular component of the immune system. Under physiological conditions, T-cells function in immune surveillance and in the elimination of foreign antigen. However, under pathological conditions, there is compelling evidence that T-cells play a major role in the causation and propagation of disease. In these disorders, breakdown of T-cell immunological tolerance, either central or peripheral is a fundamental process in the causation of autoimmune disease.

The TCR complex is composed of at least seven transmembrane proteins. The disulfide-linked ($\alpha\beta$ or $\gamma\delta$) heterodimer forms the monotypic antigen recognition unit, while the invariant chains of CD3, consisting of $\epsilon$, $\gamma$, $\delta$, $\zeta$, and $\eta$ chains, are responsible for coupling the ligand binding to signaling pathways that result in T-cell activation and the elaboration of the cellular immune responses. Despite the gene diversity of the TCR chains, two structural features are common to all known subunits. First, they are transmembrane proteins with a single transmembrane spanning domain—presumably alpha-helical. Second, all TCR chains have the unusual feature of possessing a charged amino acid within the predicted transmembrane domain. The invariant chains have a single negative charge, conserved between the mouse and human, and the variant chains possess one (TCR-$\beta$) or two (TCR-$\alpha$) positive charges. The transmembrane sequence of TCR-$\alpha$ is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an $\alpha$ and $\beta$ chain resembling an immunoglobulin variable (V) and constant (C) region. The TCR $\alpha$ chain includes a covalently linked V-$\alpha$ and C-$\alpha$ chain, whereas the $\beta$ chain includes a V-$\beta$ chain covalently linked to a C-$\beta$ chain. The V-$\alpha$ and V-$\beta$ chains form a pocket or cleft that can bind a superantigen or antigen in the context of a major histocompatibility complex (MHC) (known in humans as an HLA complex). See, Davis *Ann. Rev. of Immunology* 3: 537 (1985); Fundamental Immunology 3rd Ed., W. Paul Ed. Rsen Press LTD. New York (1993).

The extracellular domains of the TCR chains ($\alpha\beta$ or $\gamma\delta$) can also engineered as fusions to heterologous transmembrane domains for expression on the cell surface. Such TCRs may include fusions to CD3, CD28, CD8, 4-1BB and/or chimeric activation receptor (CAR) transmembrane or activation domains. TCRs can also be the soluble proteins comprising one or more of the antigen binding domains of $\alpha\beta$ or $\gamma\delta$ chains. Such TCRs may include the TCR variable domains or function fragments thereof with or without the TCR constant domains. Soluble TCRs may be heterodimeric or single-chain molecules.

Fc Domain

Protein complexes of the invention may contain an Fc domain. For example, PD-L1 TxM comprises an anti-PD-L1 scAb/huIL-15N72D:anti-PD-L1 scAb/huIL-15R$\alpha$Su/hu-IgG1 Fc fusion complex. Fusion proteins that combine the Fc regions of IgG with the domains of another protein, such as various cytokines and soluble receptors have been reported (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and CH domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15R$\alpha$ covalently linked to the Fc portion of the human heavy chain IgG protein are described herein.

The term "Fc" refers to the fragment crystallizable region which is the constant region of an antibody that interacts with cell surface receptors called Fc receptors and some proteins of the complement system. Such an "Fc" is in dimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins. In some embodiments, Fc domain of the complex is capable of interacting with Fc receptors to mediate antibody-dependent cell-mediated cytotoxicity (ADCC) and/or antibody dependent cellular phagocytosis (ADCP). In other applications, the complex comprises an Fc domain (e.g., IgG4 Fc) that is incapable of effectively mediating ADCC or ADCP.

In some embodiments, the term "Fc variant" refers to a molecule or sequence that is modified from a native Fc, but still comprises a binding site for the salvage receptor, FcRn. International applications WO 97/34631 and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that alters one or more native Fc sites or residues that affect or are involved in (1) disulfide bond formation, (2) incompatibility with a selected host cell (3)N-terminal heterogeneity upon expression in a selected host cell, (4) glycosylation, (5) interaction with complement, (6) binding to an Fc receptor other than a salvage receptor, (7) antibody-dependent cellular cytotoxicity (ADCC) or (8) antibody-dependent cellular phagocytosis (ADCP). Such alterations can increase or decrease any one or more of these Fc properties. In certain embodiments, the Fc region is a human IgG Fc region and comprises one or more amino acid substitution, deletion, insertion or modification (e.g., carbohydrate chemical modification) introduced at any position within the Fc region. In certain embodiments a human IgG Fc variant comprises one or more amino acid residue mutants and has an increased binding affinity for an FcRn as compared to the wild type Fc region not comprising the one or more amino acid residue mutants. Fc binding interactions are essential for hinging to neonatal receptor, but not limited to, increasing serum half-life of IgG. Accordingly, in certain embodiments, human IgG Fc variants exhibit altered binding affinity for at least one or more Fc ligands (e.g., FcRns) relative to an antibody having the same amino acid sequence but not comprising the one or more amino acid substitution, deletion, insertion or modification (referred to herein as a "comparable molecule") such as, for example, an unmodified Fc region containing naturally occurring amino acid residues at the corresponding position in the Fc region. Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Fusions Protein Complexes

The invention provides for fusion protein complexes. In some cases, the first protein comprises a first biologically active polypeptide covalently linked to interleukin-15 (IL-15) or functional fragment thereof; and the second protein comprises a second biologically active polypeptide covalently linked to soluble interleukin-15 receptor alpha (IL-15Rα) polypeptide or functional fragment thereof, where the IL-15 domain of a first protein binds to the soluble IL-15Rα domain of the second protein to form a soluble fusion protein complex. Fusion protein complexes of the invention also comprise immunoglobulin Fc domain or a functional fragment thereof linked to one or both of the first and second proteins. Preferably, the Fc domains linked to the fusion proteins interact to form a fusion protein complex. Such a complex may be stabilized by disulfide bond formation between the immunoglobulin Fc domains. In one aspect, the soluble fusion protein complexes of the invention include an IL-15 polypeptide, IL-15 variant or a functional fragment thereof and a soluble IL-15Rα polypeptide or a functional fragment thereof, wherein one or both of the IL-15 and IL-15Rα polypeptides further include an immunoglobulin Fc domain or a functional fragment thereof.

In certain examples, one or both of the first and second proteins comprises an antibody or functional fragment thereof. For example, one of the binding domain comprises a soluble anti-PD-L1 single chain antibody or functional fragment thereof. In another example, the other or second binding domain comprises an anti-CTLA4 single chain antibody or a disease antigen-specific antibody or functional fragment thereof. In one embodiment, the invention provides PD-L1 TxM, comprising a soluble anti-PD-L1 scAb/huIL-15N72D:anti-PD-L1 scAb/huIL-15RαSu/huIgG1 Fc fusion protein complex. In this complex, the huIL-15N72D and huIL-15RαSu domains interact and the huIgG1 Fc domains on two anti-PD-L1 scAb/huIL-15RαSu/huIgG1 Fc fusion protein to form a multichain fusion protein complex.

As used herein, the term "biologically active polypeptide" or "effector molecule" is meant an amino acid sequence such as a protein, polypeptide, or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally occurring or it can be synthesized from known components, e.g., by recombinant or chemical synthesis and can include heterologous components. A biologically active polypeptide or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a fusion complex of the invention and then evaluating whether the fusion complex inhibits further development of the cells.

Covalently linking the effector molecule to the fusion protein complexes of the invention in accordance with the invention provides a number of significant advantages. Fusion protein complexes of the invention can be produced that contain a single effector molecule, including a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of a fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.

Linkers

In certain embodiments, the fusion complexes of the invention also include a flexible linker sequence interposed between the IL-15 or IL-15Rα domains and the biologically active polypeptide. The linker sequence should allow effective positioning of the biologically active polypeptide with respect to the IL-15 or IL-15Rα domains to allow functional activity of both domains.

In certain cases, the soluble fusion protein complex has a linker wherein the first biologically active polypeptide is covalently linked to IL-15 (or functional fragment thereof) by polypeptide linker sequence. In other aspects, the soluble fusion protein complex as described herein has a linker wherein the second biologically active polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. For example, the IL-15 or IL-15Rα domains are effectively positioned to allow interactions with immune cells to initiate or inhibit an immune reaction, or to inhibit or stimulate cell development.

The fusion complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. For example, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generate a single-chain molecule with the desired functional activity.

Preferably, the linker sequence comprises from about 7 to 20 amino acids, more preferably from about 10 to 20 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine, and serine, to provide for flexibility. Preferably, about 80 or 90 percent or greater of the linker sequence comprises glycine, alanine, or serine residues, particularly glycine and serine residues.

Different linker sequences could be used including any of a number of flexible linker designs that have been used successfully to join antibody variable regions together (see, Whitlow, M. et al., (1991) Methods: A Companion to Methods in Enzymology, 2:97-105).

Pharmaceutical Therapeutics

The invention provides pharmaceutical compositions comprising fusion protein complexes for use as a therapeutic. In one aspect, fusion protein complex of the invention is administered systemically, for example, formulated in a pharmaceutically-acceptable buffer such as physiological saline. Preferable routes of administration include, for example, instillation into the bladder, subcutaneous, intravenous, intraperitoneal, intramuscular, intratumoral or intradermal injections that provide continuous, sustained, or effective levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, autoimmune or infectious diseases, although in certain instances lower amounts will be needed because of the increased specificity of the compound. A compound is administered at a dosage that enhances an immune response of a subject, or that reduces the proliferation, survival, or invasiveness of a neoplastic, infected, or autoimmune cell as determined by a method known to one skilled in the art.

Formulation of Pharmaceutical Compositions

The administration of the fusion protein complex of the invention for the treatment of a neoplasia, infectious or autoimmune disease is by any suitable means that results in a concentration of the therapeutic that, combined with other components, is effective in ameliorating, reducing, or stabilizing said neoplasia, infectious or autoimmune disease. The fusion protein complex of the invention may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intravesicular, intratumoral or intraperitoneal) administration route. For example, the pharmaceutical compositions are formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 µg compound/kg body weight to about 5000 mg compound/kg body weight; or from about 5 mg/kg body weight to about 4,000 mg/kg body weight or from about 10 mg/kg body weight to about 3,000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. For example, the dose is about 1, 5, 10, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,600, 1,700, 1,800, 1,900, 2,000, 2,500, 3,000, 3,500, 4,000, 4,500, or 5,000 mg/kg body weight. Alternatively, doses are in the range of about 5 mg compound/Kg body weight to about 20 mg compound/kg body weight. In another example, the doses are about 8, 10, 12, 14, 16 or 18 mg/kg body weight. Preferably, the fusion protein complex is administered at 0.5 mg/kg-about 10 mg/kg (e.g., 0.5, 1, 3, 5, 10 mg/kg). Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes. Preferably, the fusion protein complex is formulated in an excipient suitable for parenteral administration.

Parenteral Compositions

The pharmaceutical composition comprising a fusion protein complex of the invention are administered parenterally by injection, infusion, or implantation (subcutaneous, intravenous, intramuscular, intratumoral, intravesicular, intraperitoneal) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising a fusion protein complex of the invention for parenteral use are provided in unit dosage forms (e.g., in single-dose ampoules). Alternatively, the composition is provided in vials containing several doses and in which a suitable preservative may be added (see below). The composition is in the form of a solution, a suspension, an emulsion, an infusion device, or a delivery device for implantation, or it is presented as a dry powder to be reconstituted with water or another suitable vehicle before use. Apart from the active agent that reduces or ameliorates a neoplasia, infectious or autoimmune disease, the composition includes suitable parenterally acceptable carriers and/or excipients. The active therapeutic agent(s) may be incorporated into microspheres, microcapsules, nanoparticles, liposomes for controlled release. Furthermore, the composition may include suspending, solubilizing, stabilizing, pH-adjusting agents, tonicity adjusting agents, and/or dispersing, agents.

As indicated above, the pharmaceutical compositions comprising a fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol.

The present invention provides methods of treating neoplasia, infectious or autoimmune diseases or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplasia, infectious or autoimmune disease or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplasia, infectious disease, autoimmune disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The fusion protein complexes of the invention may be used in the treatment of any other disorders in which an increase in an immune response is desired.

The invention also provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some cases, a second level of Marker in the subject is determined at a time point later than the determination of the first level, and the two levels are compared to monitor the course of disease or the efficacy of the therapy. In certain aspects, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Optionally, the fusion protein complex of the invention is administered in combination with any other standard therapy; such methods are known to the skilled artisan and described in Remington's Pharmaceutical Sciences by E. W. Martin. If desired, fusion protein complexes of the invention is administered in combination with any conventional anti-neoplastic therapy, including but not limited to, immunotherapy, therapeutic antibodies, targeted therapy, surgery, radiation therapy, or chemotherapy.

Kits or Pharmaceutical Systems

Pharmaceutical compositions comprising the fusion protein complex of the invention may be assembled into kits or pharmaceutical systems for use in ameliorating a neoplasia, infectious or autoimmune disease. Kits or pharmaceutical systems according to this aspect of the invention comprise a carrier means, such as a box, carton, tube, having in close confinement therein one or more container means, such as vials, tubes, ampoules, bottles, and the like. The kits or pharmaceutical systems of the invention may also comprise associated instructions for using the fusion protein complex of the invention.

Recombinant Protein Expression

In general, preparation of the fusion protein complexes of the invention (e.g., components of a TxM complex) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transfection and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein) raised against the polypeptide may be attached to a column and used to isolate the recombinant polypeptide. Lysis and fractionation of polypeptide-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory Techniques in Biochemistry and Molecular Biology, eds., Work and Burdon, Elsevier, 1980).

As used herein, biologically active polypeptides or effector molecules of the invention may include factors such as cytokines, chemokines, growth factors, protein toxins, immunoglobulin domains or other bioactive proteins such as enzymes. Also, biologically active polypeptides may include conjugates to other compounds such as non-protein toxins, cytotoxic agents, chemotherapeutic agents, detectable labels, radioactive materials, and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-1, IL-17, TGF and TNF cytokine families, and to IL-1 through IL-35, IFN-α, IFN-β, IFNγ, TGF-β, TNF-α, and TNFβ.

In an aspect of the invention, the first protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL-2, although fundamental differences have been well characterized (Waldmann, T A, 2006, *Nature Rev. Immunol.* 6:595-601).

In another aspect of the invention, the first protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rα polypeptide and functions as an IL-15 agonist or antagonist. Preferably, IL-15 variants with agonist activity have super agonist activity. The IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some cases, the sequence of the IL-15 variant has at least one amino acid change, e.g. substitution or deletion, compared to the native IL-2 sequence, such changes resulting in IL-15 agonist or antagonist activity. Preferably, the amino acid substitutions/deletions are in the domains of IL-15 that interact with IL-15Rβ and/or γC. More preferably, the amino acid substitutions/deletions do not affect binding to the IL-15Rα polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally, suitable amino acid substitutions can be conservative or non-conservative changes and insertions of additional amino acids. Preferably, IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 variants with antagonist activity and N72D substitutions result in IL-15 variants with agonist activity.

Chemokines, similar to cytokines, are defined as any chemical factor or molecule which when exposed to other cells are responsible for any of a number of multiple effects of cellular immunity. Suitable chemokines may include but are not limited to the CXC, CC, C, and $CX_3C$ chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, *pseudomonas* exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; phosphorescent or chemiluminescent molecules or a label detectable by PET, ultrasound, or MRI such as Gd—or paramagnetic metal ion-based contrast agents. See e.g., Moskaug, et al. J. Biol. Chem. 264, 15709 (1989); Pastan, I. et al. Cell 47, 641, 1986; Pastan et al., Recombinant Toxins as Novel Therapeutic Agents, Ann. Rev. Biochem. 61, 331, (1992); "Chimeric Toxins" Olsnes and Phil, Pharmac. Ther., 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

A protein fusion or conjugate complex that includes a covalently linked IL-15 and IL-15Rα domains has several important uses. For example, the protein fusion or conjugate complex comprising an anti-PD-L1 scAb can be employed to deliver the IL-15:IL-15Rα complex to certain cells, e.g., tumor cells that express PD-L1. Accordingly, the protein fusion or conjugate complex provides means of selectively damaging or killing cells comprising the ligand. Examples of cells or tissue capable of being damaged or killed by the protein fusion or conjugate complexes include tumors and virally or bacterially infected cells expressing one or more ligands. Cells or tissue susceptible to being damaged or killed can be readily assayed by the methods disclosed herein.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammals. Sequences of these polypeptides and encoding nucleic acids are known in the literature, including human interleukin 15 (IL15) mRNA—GenBank: U14407.1 (incorporated herein by reference), *Mus musculus* interleukin 15 (IL15) mRNA—GenBank: U14332.1 (incorporated herein by reference), human interleukin-15 receptor alpha chain precursor (IL15RA) mRNA—GenBank: U31628.1 (incorporated herein by reference), *Mus musculus* interleukin 15 receptor, alpha chain—GenBank: BC095982.1 (incorporated herein by reference).

In some settings, it can be useful to make the protein fusion or conjugate complexes of the present invention polyvalent, e.g., to increase the valency of the sc-antibody. In particular, interactions between the IL-15 and IL-15Rα domains of the fusion protein complex provide a means of generating polyvalent complexes. In addition, the polyvalent fusion protein can be made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, *Aldrichimica Acta,* 26:91:101 (1993)). Exemplary dendrimers for use in accordance with the present invention include e.g. E9 starburst polyamine dendrimer and E9 combust polyamine dendrimer, which can link cystine residues. Exemplary nanoparticles include liposomes, core-shell particles, or PLGA-based particles.

In another aspect, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 $C_H2$-$C_H3$, are capable of stably interacting to create the Fc region. Preferred immunoglobulin domains including Fc domains also comprise regions with effector functions, including Fc receptor or complement protein binding activity, and/or with glycosylation sites. In some aspects, the immunoglobulin domains of the fusion protein complex contain mutations that reduce or augment Fc receptor or complement binding activity or glycosylation or dimerization, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present fusion proteins (e.g., components of TxM). Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See, Sambrook et al., supra and Ausubel et al., supra.

Included in the invention are methods for making a soluble fusion protein complex, the method comprising introducing into a host cell a DNA vector as described herein encoding the first and second proteins, culturing the host cell in media under conditions sufficient to express the fusion proteins in the cell or the media and allow association between IL-15 domain of a first protein and the soluble IL-15Rα domain of a second protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity, and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization, and wash conditions of 40-50 C, 6×SSC (sodium chloride/sodium citrate buffer) and 0.1% SDS (sodium dodecyl sulfate) indicate about 60-70% homology, hybridization, and wash conditions of 50-65 C, 1×SSC and 0.1% SDS indicate about 82-97% homology, and hybridization, and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See, e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However, it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express the components of fusion protein complex of the invention (e.g., TxM). For example, a construct encoding one or more components of fusion protein complex of the invention can be incorporated into a suitable vector using restriction enzymes to make cuts in the vector for insertion of the construct followed by ligation. The vector containing the gene construct is then introduced into a suitable host for expression of the fusion protein. See, generally, Sambrook et al., supra. Selection of suitable vectors can be made empirically based on factors relating to the cloning protocol. For example, the vector should be compatible with, and have the proper replicon for the host that is being employed. The vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically, preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See, Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immuno-blotting. Other methods for detecting expression of fusion proteins comprising biologically active polypeptides linked to IL-15 or IL-15Rα domains are disclosed in the Examples section which follows.

As mentioned generally above, a host cell can be used for preparative purposes to propagate nucleic acid encoding a desired fusion protein. Thus, a host cell can include a prokaryotic or eukaryotic cell in which production of the fusion protein is specifically intended. Thus, host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et al., *J Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired fusion protein complexes encompass non-mammalian eukaryotic cells as well, including insect (e.g., Sp. frugiperda), yeast (e.g., *S. cerevisiae, S. pombe, P. pastoris., K. lactis, H. polymorpha*; as generally reviewed by Fleer, R., *Current Opinion in Biotechnology*, 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1,000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10-fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (λZAP and pBLUESCRIPT SK-1, Stratagene, La Jolla, Calif., pET, Novagen Inc., Madison, Wis., cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization, and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically, the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion complex. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

The present fusion protein complexes are suitable for in vitro or in vivo use with a variety of cells that are cancerous or are infected or that may become infected by one or more diseases.

Human interleukin-15 (huIL-15) is trans-presented to immune effector cells by the human IL-15 receptor α chain (huIL-15Rα) expressed on antigen presenting cells. IL-15Rα binds huIL-15 with high affinity (38 pM) primarily through the extracellular sushi domain (huIL-15RαSu). As described herein, the huIL-15 and huIL-15RαSu domains can be used as a scaffold to construct multi-domain fusion complexes.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcomes for a number of different autoimmune indications.

In addition to its dimerization activity, the Fc fragment also provides cytotoxic effector functions through the complement activation and interaction with Fcγ receptors displayed on natural killer (NK) cells, neutrophils, phagocytes, and dendritic cells. In the context of anti-cancer therapeutic antibodies and other antibody domain-Fc fusion proteins, these activities likely play an important role in efficacy observed in animal tumor models and in cancer patients. However, these cytotoxic effector responses may not be sufficient in a number of therapeutic applications. Thus, there has been considerable interest in improving and expanding on the effector activity of the Fc domain and developing other means of recruiting cytolytic immune responses, including T cell activity, to the disease site via targeted therapeutic molecules. IgG domains have been used as a scaffold to form bispecific antibodies to improve the quality and quantity of products generated by the traditional hybridoma fusion technology. Although these methods bypass the shortcomings of other scaffolds, it has been difficult to produce bispecific antibodies in mammalian cells at levels sufficient to support clinical development and use.

In an effort to develop human-derived immunostimulatory multimeric scaffold, human IL-15 (huIL-15) and IL-15 receptor domains were used. huIL-15 is a member of the small four α-helix bundle family of cytokines that associates with the huIL-15 receptor α-chain (huIL-15Rα) with a high binding affinity (equilibrium dissociation constant (KD) ~$10^{-11}$ M). The resulting complex is then trans-presented to the human IL-2/15 receptor β/common γ chain (huIL-15RβγC) complexes displayed on the surface of T cells and NK cells. This cytokine/receptor interaction results in expansion and activation of effector T cells and NK cells, which play an important role in eradicating virally infected and malignant cells. Normally, huIL-15 and huIL-15Rα are co-produced in dendritic cells to form complexes intracellularly that are subsequently secreted and displayed as heterodimeric molecules on cell surfaces. Thus, the characteristics of huIL-15 and huIL-15Rα interactions suggest that these inter chain binding domains could serve as a human-derived immunostimulatory scaffold to make soluble dimeric molecules capable of target-specific binding.

As described in detail below, an huIL-15:huIL-15RαSu-based scaffold was used to create PD-L1/TGFβRII/TxM. The dimeric fusion protein complexes retained immunostimulatory and target-specific biological activity of their huIL-15 domains and binding domains, indicating that the addition of huIL-15 and huIL-15Rα did not significantly alter the spatial arrangement of the fusion domains and provided an adequate degree of conformational flexibility without impacting cytokine activity. Thus, this scaffold could be used to form multivalent fusion complexes, such as the PD-L1 TxM, to increase the overall binding affinity of molecules. The soluble fusion proteins were produced at relatively high levels in recombinant CHO cell culture (mgs per liter in cell culture supernatant without extensive cell line screening or optimization) and could be readily purified from the cell culture supernatants.

The practice of the present invention employs, unless otherwise indicated, conventional techniques of molecular biology (including recombinant techniques), microbiology, cell biology, biochemistry, and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Lymphoma

Lymphoma is a type of blood cancer that occurs when B or T lymphocytes divide faster than normal cells or live longer than intended. For example, B cell lymphomas include both Hodgkin's lymphomas and most non-Hodgkin's lymphomas. B cell lymphomas express CD20.

Lymphoma may develop in the lymph nodes, spleen, bone marrow, blood, or other organs. These malignant cells often originate in the lymph nodes, presenting as an enlargement of the node, i.e., a solid tumor of lymphoid cells. Lymphoma is definitively diagnosed by a lymph node biopsy, i.e., a partial or total excision of a lymph node, which is examined under a microscope. This examination may reveal histopathological features that may indicate lymphoma. Treatment might involve chemotherapy, radiotherapy, and/or bone marrow transplantation.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Generation and Characterization of Fusion Protein Complexes Comprising IL-15, Anti-PDL1, and TGFβRII Domains An important therapeutic approach for treating cancer or infectious disease relies on augmenting immune cell activity against the diseased cells. This strategy includes stimulating immune cells ex vivo followed by adoptive transfer and/or directly increasing immune cell levels or activity in vivo in the patient. Immune cells involved in these approaches may be those of the innate (i.e., NK cells) or adaptive (i.e., T cells) immune system.

One approach for augmenting immune activity is to provide immunostimulatory cytokines to the immune cells. Such cytokines are known in the art and can be used alone or in combination with other cytokines or agents. As described in detail below, we generated fusion protein complexes comprising an IL-15N72D:IL-15RαSu/Fc scaffold fused to an antibody (Ab) or antibody binding fragment which can binds to an immune checkpoint protein Programmed Death Ligand 1 (PD-L1), and a TGFβRII domain which are capable of binding TGFβ. These fusion protein complexes have advantages in binding to NK cells and signaling cell responses via cytokine receptors. The Fc region of Ig molecules forms a dimer to provide a soluble multi-polypeptide complex, can bind Protein A for the purpose of purification and can interact with Fcγ receptors on NK cells and macrophages, capable of mediating ADCC and ADCP. Additionally, interactions between the IL-15N72D and IL-15RαSu domains provides a means to link the IL-15N72D, TGFβRII and anti-PDL1 antibody (Ab) domains (and possibly other protein domains or agents) into a single immunostimulatory fusion protein complex.

Specifically, constructs were made linking a TGFβRII monomer or dimer or a single chain of anti-PDL1 Ab to the IL-15N72D and IL-15RαSu/Fc chains. In the case of TGFβRII dimer, the peptide consists of two TGFβRII that can be linked via a flexible linker sequence to generate an active single-chain form. In some cases, either TGFβRII dimer and/or anti-PDL1 Ab is linked to the N-terminus of the IL-15N72D and/or IL-15RαSu/Fc chains through genetically engineered fusions. In other cases, a TGFβRII polypeptide is linked to the C-terminus of IL-15RαSu/Fc chains with/without linker. Specific fusion protein complexes comprising an IL-15N72D:IL-15RαSu/Fc scaffold fused to TGFβRII and anti-PDL1 binding domains are described below.

A: αPDL1/TGFβRII/TXM (N-810C):

A fusion protein complex was generated comprising TGFβRII dimer/IL-15RαSu/Fc and anti-PDL1-IL15N72D fusion proteins.

A1: TGFβRII/IL-15RαSu/Fc:

the human TGFβRII coding sequences were obtained from the UniProt website and optimized for CHO cell lines transfection. Specifically, gene constructs were made by linking the coding sequence for a TGFβRII to another TGFβRII by a linker to generate sequence encoding a TGFβRII dimer, and then directly linking this sequence to one encoding the N-terminus of IL-15RαSu/Fc chain. DNA sequence of the construct was synthesized by Genewiz Inc and used for molecular cloning into the expression vector.

The nucleic acid sequence of the TGFβRII/IL-15RαSu/Fc construct (including signal peptide sequence) is as follows (SEQ ID NO: 1):

(Signal peptide)
atgaagtgggtgaccttcatcagcctgctgttcctgttctccagcgccta ctcc (Human TGFβRII)
atcccccccatgtgcaaaagagcgtgaacaacgatatgatcgtgaccga caacaacggcgccgtgaagtttccccagctctgcaagttctgcgatgtca ggttcagcacctgcgataatcagaagtcctgcatgtccaactgcagcatc acctccatctgcgagaagccccaagaagtgtgcgtggccgtgtggcggaa aaatgacgagaacatcaccctggagaccgtgtgtcacgaccccaagctcc cttatcacgacttcattctggaggacgctgcctcccccaaatgcatcatg aaggagaagaagaagcccggagagaccttctttatgtgttcctgtagcag cgacgagtgtaacgacaacatcatcttcagcgaagagtacaacaccagca accctgat (Linker)
ggaggtggcggatccggaggtggaggttctggtggaggtgggagt (Human TGFβRII)
attcctccccacgtgcagaagagcgtgaataatgacatgatcgtgaccga taacaatggcgccgtgaaattccccagctgtgcaaattctgcgatgtga ggttttccacctgcgacaaccagaagtcctgtatgagcaactgctccatc acctccatctgtgagaagcctcaggaggtgtgcgtggctgtctggcggaa gaatgacgagaatatcaccctggaaaccgtctgccacgatcccaagctgc cctaccacgatttcatcctggaagacgccgcagccctaagtgcatcatg aaagagaaaaagaagcctggcgagacctttttcatgtgctcctgcagcag cgacgaatgcaacgacaatatcatctttagcgaggaatacaataccagca accccgac (Human IL-15R α sushi domain)
atcacgtgtcctcctcctatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgcattaga (Human IgG1 CH2-CH3 (Fc) domain)
gagccgaaatcttgtgacaaaactcacacatgcccaccgtgcccagcacc tgaactcctgggggaccgtcagtcttcctcttccccccaaaacccaagg acacctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca -continued

```
cgtaccgtgtggtcagcgtcctcaccgtcctgcaccaggactggctgaat ggcaaggagtacaagtgcaaggtctccaacaaagccctcccagccccat cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc aggtggcagcaggggaacgtcttctcatgctccgtgatgcatgaggctct gcacaaccactacacgcagaagagcctctccctgtctcctggtaaa
```

The amino acid sequence of the be TGFβRII/IL-15RαSu/Fc fusion protein (including signal peptide sequence) is as follows (SEQ ID NO: 2):

```
(Signal peptide)
MKWVTFISLLFLFSSAYS (Human TGFβRII)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Linker)
GGGGSGGGGSGGGGS (Human TGFβRII)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

In some cases, the leader peptide is cleaved from the intact polypeptide to generate the mature form that may be soluble or secreted.

A2: Anti-PDL1-15N72D:

Constructs were also made by linking the synthesized single chain anti-PDL1 antibody nucleotide sequence to the N-terminus coding region of IL-15N72D via overlapping PCR to generate anti-PDL1-15N72D. Specifically, the light chain and heavy chain variable domain sequences of anti-PDL1 Ab were linked by a sequence encoding flexible linker to form a single chain anti-PDL1 antibody construct, then the single chain anti-PD-L1 sequence was linked to the sequence encoding the N-terminus of IL-15N72D. The sequence of single chain anti-PDL1 Ab was synthesized by Genewiz Inc, and was then linked to the N-terminal coding region of IL-15N72D via overlapping PCR. The nucleic acid and protein sequences of a construct comprising single chain anti-PDL1 Ab linked to the N-terminus of IL15N72D are shown below.

The nucleic acid sequence of the anti-PDL1/IL-15N72D construct (including leader sequence) is as follows (SEQ ID NO: 3):

```
(Signal peptide)
atgaagtgggtgaccttcatcagcctgctgttcctgttctccagcgccta ctcc (anti-PDL1 single chain)

(anti-PDL1 light chain variable domain)
aacatccagatgacccagtcccctagctccgtgtccgcctccgtgggaga tcgggtgaccatcacctgtagggcctcccaggacatctccaggtggctgg cctggtaccagcagaagcccggcaaggcccccaagctgctgatctacgcc gcctcctccctgcagtccggagtgcctagcaggttctccggctccggatc cggcacagacttcgccctgaccatctcctccctgcagcccgaggacttcg ccacctactactgccagcaggccgactccaggttctccatcaccttcggc cagggcaccaggctggagatcaagaggg (Linker)
ggaggtggcggatccggaggtggaggttctggtggaggtgggagt (anti-PDL1 heavy chain variable domain)
gaggtgcagctggtgcagtccggaggaggactggtgcagcctggcggatc cctgaggctgtcctgtgccgcttccggcttcaccttcagctcctactcca tgaactgggtgaggcaggcccctggaaagggcctggagtgggtgtcctac atctccagctcctcctccaccatccagtacgccgactccgtgaagggcag gttcaccatctccagggacaacgccaagaactccctgtacctgcagatga acagcctgagggacgaggacaccgccgtgtactactgcgccaggggcgac tattactacggcatggacgtgtggggccagggaaccaccgtgaccgtgtc ctcc (Human IL-15N72D)
aactgggttaacgtaataagtgatttgaaaaaaattgaagatcttattca atctatgcatattgatgctactttatatacggaaagtgatgttcacccca gttgcaaagtaacagcaatgaagtgctttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaattttg cagagttttgtacatattgtccaaatgttcatcaacacttct
```

The amino acid sequence of the anti-PDL1/IL-15N72D fusion protein (including leader sequence) is as follows (SEQ ID NO: 4):

```
(Signal peptide)
MKWVTFISLLFLFSSAYS (anti-PDL1 single chain)

(anti-PDL1 light chain variable domain)
NIQMTQSPSSVSASVGDRVTITCRASQDISRWLAWYQQKPGKAPKLLIYA
```

-continued
ASSLQSGVPSRFSGSGSGTDFALTISSLQPEDFATYYCQQADSRFSITFG

QGTRLEIKR (Linker)
GGGGSGGGGSGGGGS (anti-PDL1 heavy chain variable domain)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

In some cases, the leader peptide is cleaved from the intact polypeptide to generate the mature form that may be soluble or secreted.

Co-Transfection and Protein Purification.

Figure 1:
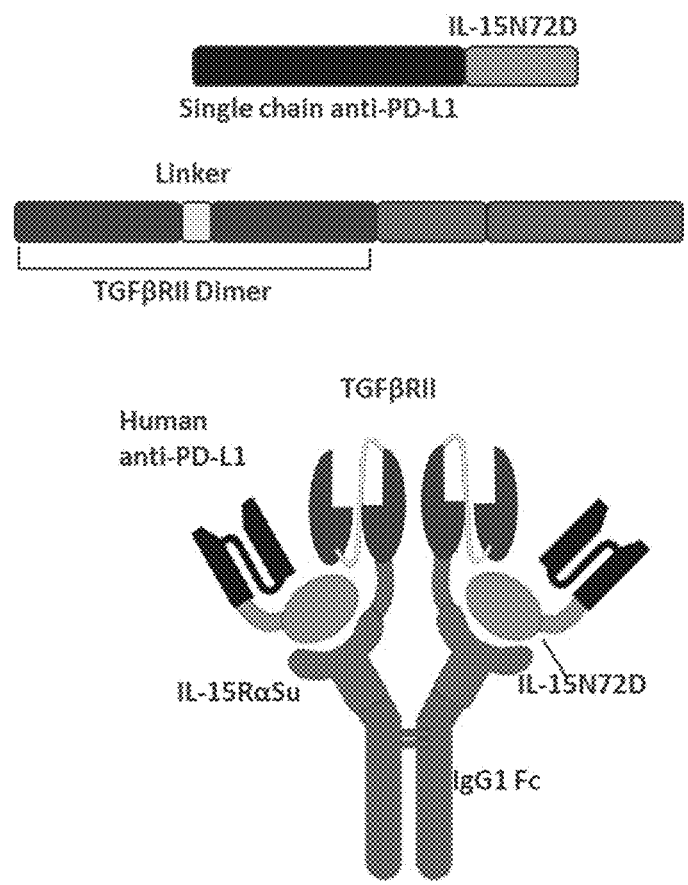
FIG. 1 is a schematic diagram illustrating an embodiment of a structure of the construct: αPDL1/TGFβRII/TXM.
Figure 2:
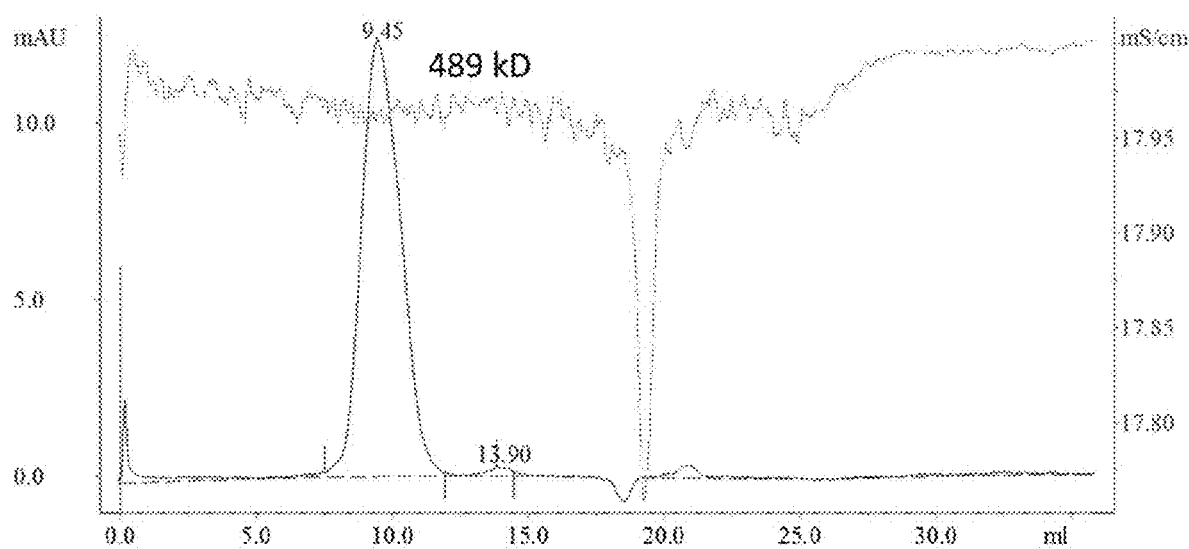
FIG. 2 is an analytical Size Exclusion Chromatography (SEC) of αPDL1/TGFβRII/TXM after rProtein A purification.

TGFβRII/IL-15RαSu/Fc and anti-PDL1-IL15N72D constructs were cloned into expression vectors as described previously (U.S. Pat. No. 8,507,222, at Example 1, incorporated herein by reference), and the expression vectors were transfected into CHO cells. Co-expression of the two constructs in CHO cells allowed for formation and secretion of a soluble anti-PDL1-IL15N72D: TGFβRII/IL-15RαSu/Fc fusion protein complex (referred to as anti-PDL1/TGFβRII/TxM). The anti-PDL1/TGFβRII/TxM protein was purified from CHO cell culture supernatant by Protein A affinity chromatography and size exclusion chromatography resulting in soluble (non-aggregated) fusion protein complexes consisting of TGFβRII/IL-15RαSu/Fc dimers and anti-PDL1-IL15N72D fusion proteins (FIG. 2).

Figure 3:
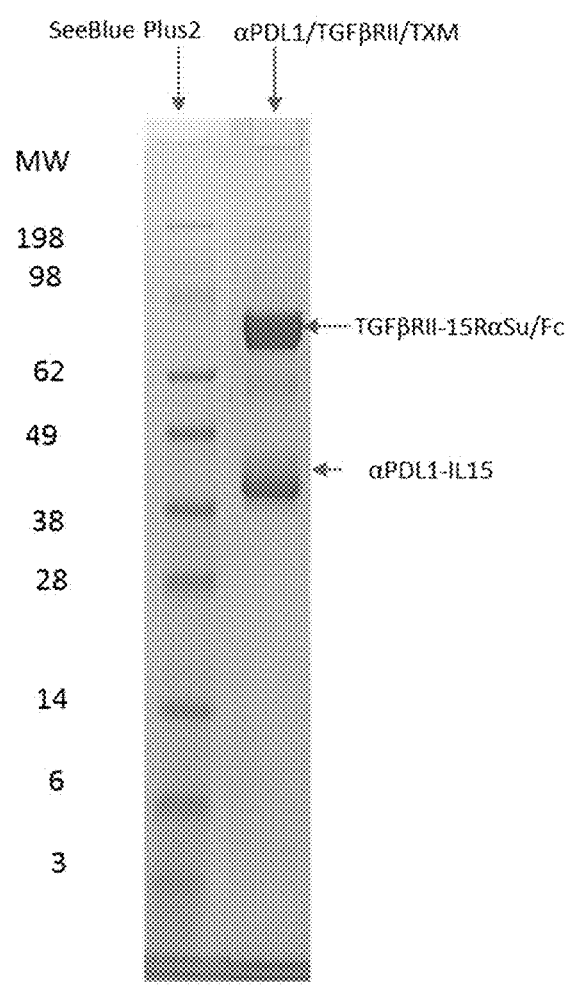
FIG. 3 is a scan of a photograph showing reduced SDS PAGE results of αPDL1/TGFβRII/TXM.
Figure 4:
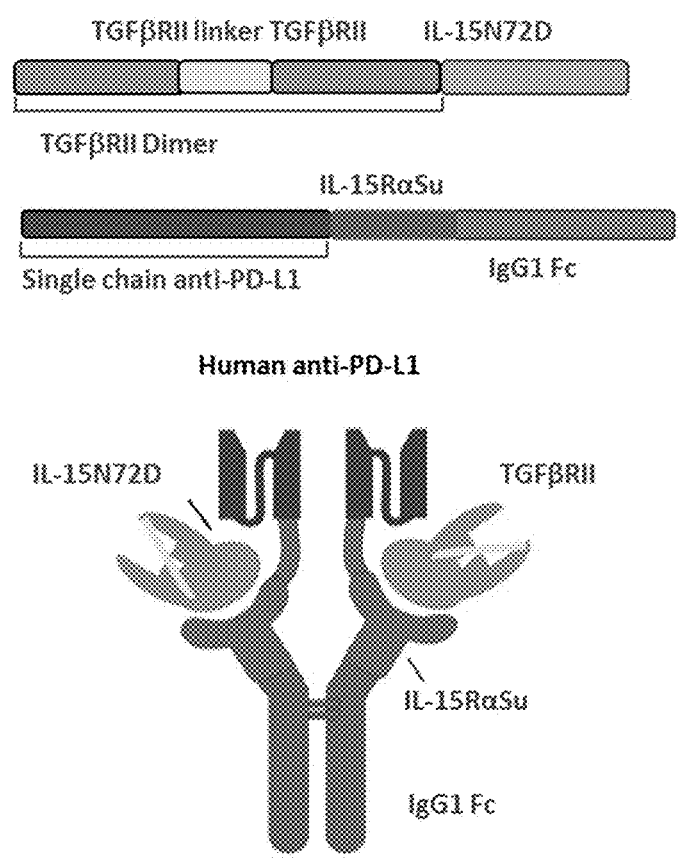
FIG. 4 is schematic diagram illustrating an embodiment of a structure of construct: TGFβRII/αPDL1/TXM.
Figure 8:
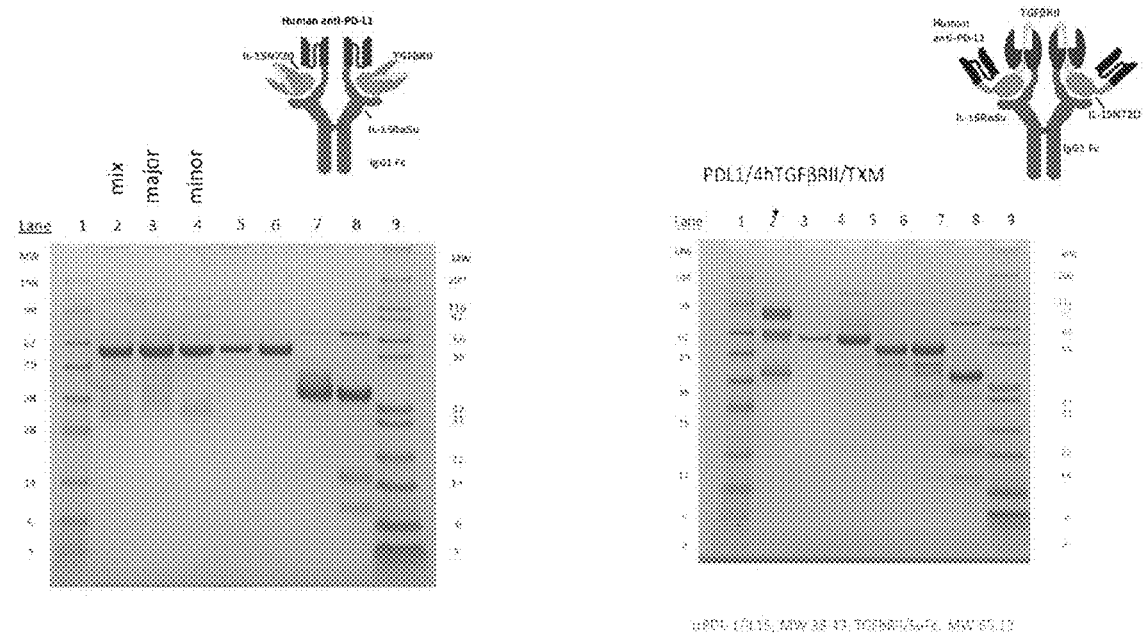
FIG. 8 shows the reduced SDS-PAGE results for TGFβRII/αPDL1/TXM and αPDL1/TGFβRII/TXM.

Reduced SDS-PAGE analysis of the Protein A-purified anti-PDL1-IL15N72D: TGFβRII/IL-15RαSu/Fc fusion protein complexes is shown in FIG. 3. Bands corresponding to the soluble anti-PDL1-IL15N72D: TGFβRII/IL-15RαSu/Fc fusion protein proteins at ~40 kDa and ~70 kDa, respectively, were observed (FIGS. 3 and 8).

B: TGFβRII/αPDL1/TXM (N-810B)

For a second approach, a similar fusion protein complex was generated comprising TGFβRII-IL15N72D: anti-PDL1-15RαSu/Fc fusion protein.

B1: Anti-PDL1-15RαSu/Fc:

The anti-PDL1-15RαSu/Fc gene construct was generated by linking the synthesized single chain anti-PDL1 Ab nucleotide sequence to the N-terminal coding region of IL-15RαSu/Fc via overlapping PCR. The nucleic acid and protein sequences of a construct comprising the anti-PDL1 Ab linked to the N-terminus of IL-15RαSu/Fc are shown below.

The nucleic acid sequence of the anti-PDL1/IL-15RαSu/Fc construct (including signal peptide sequence) is as follows (SEQ ID NO: 5):

(Signal peptide)
atgaagtgggtgaccttcatcagcctgctgttcctgttctccagcgccta ctcc (anti-PDL1 single chain)

(anti-PDL1 light chain variable domain)

-continued
aacatccagatgacccagtcccctagctccgtgtccgcctccgtgggaga tcgggtgaccatcacctgtagggcctcccaggacatctccaggtggctgg cctggtaccagcagaagcccggcaaggcccccaagctgctgatctacgcc gcctcctccctgcagtccggagtgcctagcaggttctccggctccggatc cggcacagacttcgccctgaccatctcctccctgcagcccgaggacttcg ccacctactactgccagcaggccgactccaggttctccatcaccttcggc cagggcaccaggctggagatcaagagg (Linker)
ggaggtggcggatccggaggtggaggttctggtggaggtgggagt (anti-PDL1 heavy chain variable domain)
gaggtgcagctggtgcagtccggaggaggactggtgcagcctggcggatc cctgaggctgtcctgtgccgcttccggcttcaccttcagctcctactcca tgaactgggtgaggcaggcccctggaaagggcctggagtgggtgtcctac atctccagctcctcctccaccatccagtacgccgactccgtgaagggcag gttcaccatctccagggacaacgccaagaactccctgtacctgcagatga acagcctgagggacgaggacaccgccgtgtactactgcgccaggggcgac tattacggcatggacgtgtggggccagggaaccaccgtgaccgtgtc ctcc (Human IL-15R α sushi domain)
atcacgtgtcctcctcctatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgcattaga (Human IgG1 CH2-CH3 (Fc) domain)
gagccgaaatcttgtgacaaaactcacacatgcccaccgtgcccagcacc tgaactcctggggggaccgtcagtcttcctcttccccccaaaacccaagg acaccctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca cgtaccgtgtggtcagcgtcctcaccgtcctgcaccaggactggctgaat ggcaaggagtacaagtgcaaggtctccaacaaagcctcccagccccat cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc aggtggcagcaggggaacgtcttctcatgctccgtgatgcatgaggctct gcacaaccactacacgcagaagagcctctccctgtctccggtaaa The amino acid sequence of the anti-PDL1/IL-15RαSu/Fc fusion protein (including signal peptide sequence) is as follows (SEQ ID NO: 6): (Signal peptide)

(Signal peptide)
MKWVTFISLLFLFSSAYS (anti-PDL1 single chain)

(anti-PDL1 light chain variable domain)

NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (anti-PDL1 heavy chain variable domain)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (Human IL-15R α sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some cases, the leader peptide is cleaved from the intact polypeptide to generate the mature form that may be soluble or secreted.

B2: TGFβRII-IL15N72D:

Specifically, constructs were made linking a TGFβRII to another TGFβRII by a linker to generate a TGFβRII dimer, and then directly linking the TGFβRII dimer sequence to the N-terminus of IL15N72D. The DNA fragment encoding TGFβRII-IL15N72D was synthesized by GENEWIZ.

The nucleic acid sequence of the TGFβRII-IL15N72D construct (including signal peptide sequence) is as follows (SEQ ID NO: 7):

(Signal peptide)
atgaagtgggtgaccttcatcagcctgctgttcctgttctccagcgccta ctcc (Human TGFβRII)
atcccccccatgtgcaaaagagcgtgaacaacgatatgatcgtgaccga caacaacggcgccgtgaagtttccccagctctgcaagttctgcgatgtca ggttcagcacctgcgataatcagaagtcctgcatgtccaactgcagcatc acctccatctgcgagaagcccaagaagtgtgcgtggccgtgtggcggaa aaatgacgagaacatcaccctggagaccgtgtgtcacgaccccaagctcc cttatcacgacttcattctggaggacgctgcctcccccaaatgcatcatg aaggagaagaagaagcccggagagaccttctttatgtgttcctgtagcag cgacgagtgtaacgacaacatcatcttcagcgaagagtacaacaccagca accctgat (Linker)
ggaggtggcggatccggaggtggaggttctggtggaggtgggagt (Human TGFβRII)
attcctccccacgtgcagaagagcgtgaataatgacatgatcgtgaccga taacaatggcgccgtgaaatttccccagctgtgcaaattctgcgatgtga ggttttccacctgcgacaaccagaagtcctgtatgagcaactgctccatc acctccatctgtgagaagcctcaggaggtgtgcgtggctgtctggcggaa gaatgacgagaatatcaccctggaaaccgtctgccacgatcccaagctgc cctaccacgatttcatcctggaagacgccgcagccctaagtgcatcatg aaagagaaaaagaagcctggcgagaccttttttcatgtgctcctgcagcag cgacgaatgcaacgacaatatcatctttagcgaggaatacaataccagca accccgac (Human IL-15N72D)
aactgggttaacgtaataagtgatttgaaaaaaattgaagatcttattca atctatgcatattgatgctactttatatacggaaagtgatgttcacccca gttgcaaagtaacagcaatgaagtgctttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaattttg cagagttttgtacatattgtccaaatgttcatcaacacttct The amino acid sequence of the TGFβRII-IL15N72D fusion protein (including leader sequence) is as follows (SEQ ID NO: 8):

(Signal peptide)
MKWVTFISLLFLFSSAYS (Human TGFβRII)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Linker)
GGGGSGGGGSGGGGS (Human TGFβRII)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

In some cases, the leader peptide is cleaved from the intact polypeptide to generate the mature form that may be soluble or secreted.

Co-Transfection and Protein Purification:

The TGFβRII dimer/IL-15N72D and αPDL1/IL-15RαSu/Fc constructs were cloned into expression vectors as described previously (U.S. Pat. No. 8,507,222, at Example 1, incorporated herein by reference), and the expression vectors were transfected into CHO cells. Co-expression of the two constructs in CHO cells allowed for formation and secretion of the soluble TGFβRII/IL-15N72D: αPDL1/IL-15RαSu/Fc fusion protein complex (referred to as TGFβRII/αPDL1/TxM).

Figure 5:
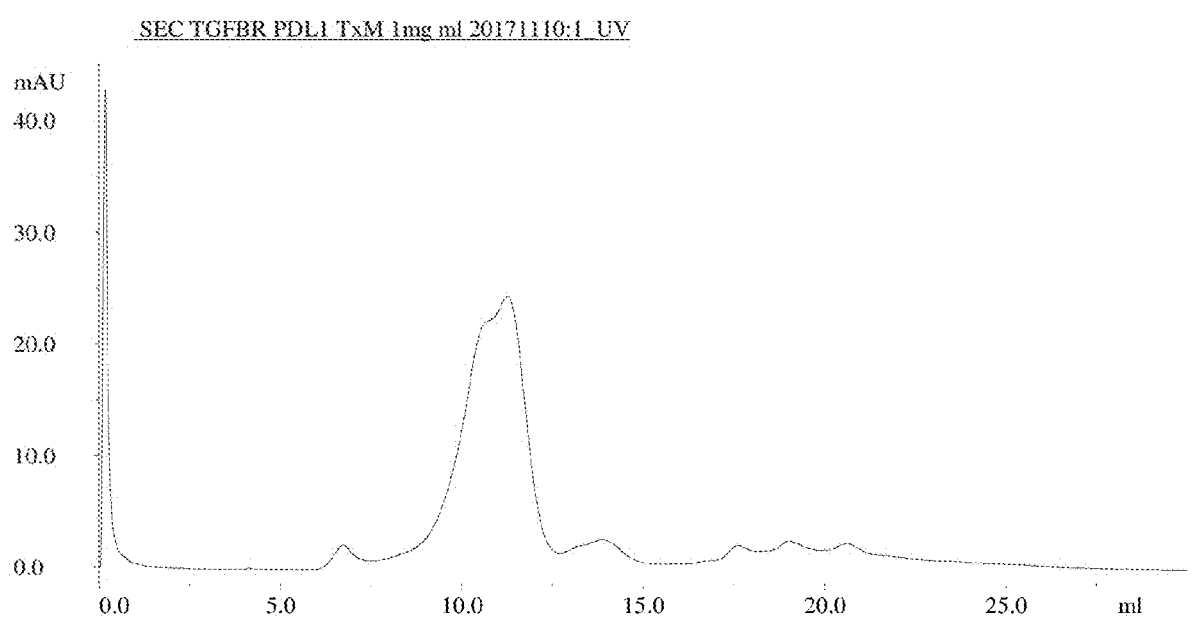
FIG. 5 is an analytical SEC of TGFβRII/αPDL1/TXM after rProtein A purification.

The TGFβRII/anti-PDL1/TxM protein was purified from CHO cell culture supernatant by Protein A affinity chromatography and size exclusion chromatography resulting in soluble (non-aggregated) fusion protein complexes (FIG. 5).

Figure 6:
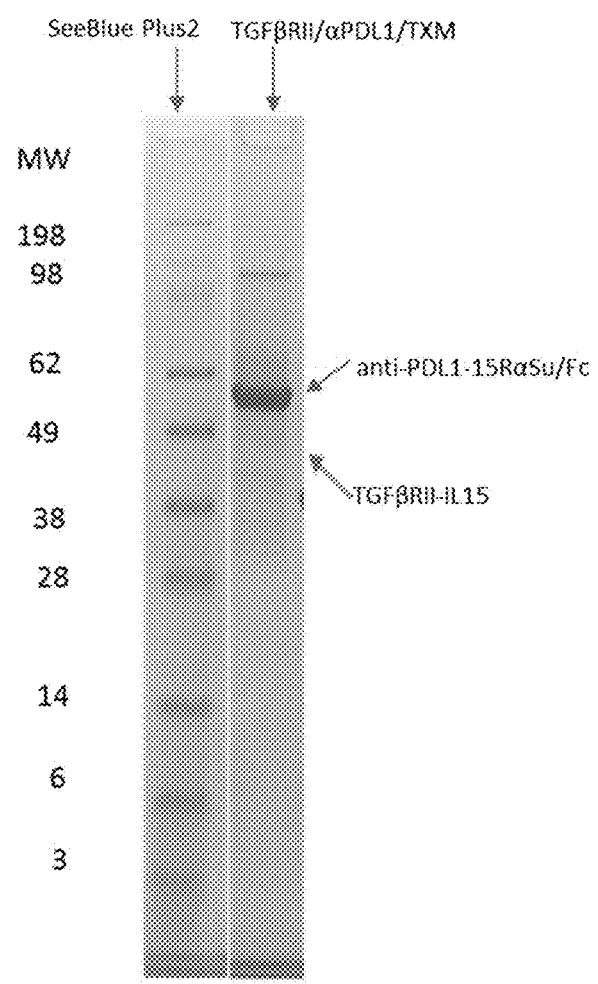
FIG. 6 is a scan of a photograph showing reduced SDS PAGE results of TGFβRII/αPDL1/TXM.

Reduced SDS-PAGE analysis of the Protein A-purified TGFβRII/anti-PDL1/TxM fusion protein complexes is shown in FIG. 6. Bands corresponding to the soluble anti-PDL1-IL15N72D: TGFβRII/IL-15RαSu/Fc fusion protein proteins at ~50 kDa and ~60 kDa, respectively, were observed (FIGS. 6 and 8).

C: αPDL1/TXM/TGFβRII (N-810A)

Figure 7:
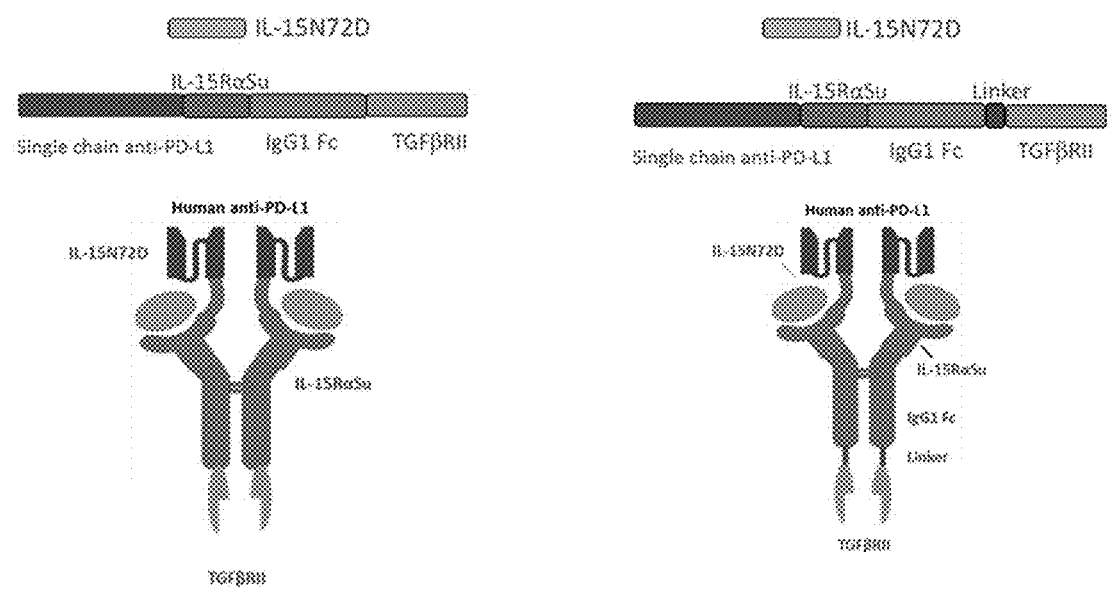
FIG. 7 is schematic diagram illustrating embodiments of a structure of construct: αPDL1/TxM/TGFβRII.

Fusion protein complexes were also generated, which comprising IL15N72D and anti-PDL1/IL-15RαSu/Fc/TGFβRII. In these constructs, TGFβRII was fused to C-terminal of anti-PDL1-IL-15RαSu/Fc with or without linker (FIG. 7).

C1: IL15N72D:

IL15N72D construct was made as described previously (U.S. Pat. No. 8,507,222, at Example 1, incorporated herein by reference).

The nucleic acid sequence of the IL15N72D construct (including signal peptide sequence) is as follows (SEQ ID NO: 9):

```
(Signal peptide)
atgaagtgggtgaccttcatcagcctgctgttcctgttctccagcgccta ctcc (Human IL-15N72D)
aactgggttaacgtaataagtgatttgaaaaaaattgaagatcttattca atctatgcatattgatgctactttatatacggaaagtgatgttcacccca gttgcaaagtaacagcaatgaagtgctttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaattttg cagagttttgtacatattgtccaaatgttcatcaacacttct
```

The amino acid sequence of the IL15N72D protein (including leader sequence) is as follows (SEQ ID NO: 10):

```
(Signal peptide)
MKWVTFISLLFLFSSAYS (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS
```

In some cases, the leader peptide is cleaved from the intact polypeptide to generate the mature form that may be soluble or secreted.

C2: Anti-PDL1/IL-15RαSu/Fc/TGFβRII:

Two constructs were made for this fusion protein (FIG. 7). In the first construct, TGFβRII was fused directly to C-terminal of anti-PDL1/IL-15RαSu/Fc. In the second construct, a linker was added between TGFβRII and anti-PDL1/IL-15RαSu/Fc to increase the flexibility. Both of the constructs, the nucleic acid sequences encoding anti-PDL1/IL-15RαSu/Fc/TGFβRII were synthesized by Genewiz. A nucleic acid mutation was made at position 27 (G to T) of the TGFβRII sequence to generate a Hap1 restriction enzyme cutting site at that position, however, there was no amino acid sequence change.

C2A: Anti-PDL1/IL-15RαSu/Fc/TGFβRII—No Linker:

The nucleic acid sequence of the anti-PDL1/IL-15RαSu/Fc/TGFβRII construct without linker (including signal peptide sequence) is as follows (SEQ ID NO: 11):

```
(Signal peptide)
atgaagtgggtgaccttcatcagcctgctgttcctgttctccagcgccta ctcc (anti-PDL1 single chain)

(anti-PDL1 light chain variable domain)
aacatccagatgacccagtcccctagctccgtgtccgcctccgtgggaga tcgggtgaccatcacctgtagggcctcccaggacatctccaggtggctgg cctggtaccagcagaagcccggcaaggcccccaagctgctgatctacgcc gcctcctccctgcagtccggagtgcctagcaggttctccggctccggatc cggcacagacttcgccctgaccatctcctccctgcagcccgaggacttcg ccacctactactgccagcaggccgactccaggttctccatcaccttcggc cagggcaccaggctggagatcaagagg (Linker)
ggaggtggcggatccggaggtggaggttctggtggaggtgggagt (anti-PDL1 heavy chain variable domain)
gaggtgcagctggtgcagtccggaggaggactggtgcagcctggcggatc cctgaggctgtcctgtgccgcttccggcttccacttcagctcctactcca tgaactgggtgaggcaggcccctggaaagggcctggagtgggtgtcctac atctccagctcctcctccaccatccagtacgccgactccgtgaagggcag gttcaccatctccagggacaacgccaagaactccctgtacctgcagatga acagcctgagggacgaggacaccgccgtgtactactgcgccaggggcgac tattactacggcatggacgtgtggggccagggaaccaccgtgaccgtgtc ctcc (Human IL-15R α sushi domain)
atcacgtgtcctcctcctatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgcattaga (Human IgG1 CH2-CH3 (Fc) domain)
gagccgaaatcttgtgacaaaactcacacatgcccaccgtgcccagcacc tgaactcctggggggaccgtcagtcttcctcttccccccaaaacccaagg acaccctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca cgtaccgtgtggtcagcgtcctcaccgtcctgcaccaggactggctgaat ggcaaggagtacaagtgcaaggtctccaacaaagccctcccagcccccat cgagaaaaccatctccaaagccaaagggcagccccgagaaccacaggtgt acaccctgcccccatcccgggatgagctgaccaagaaccaggtcagcctg
```

-continued

```
acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc aggtggcagcaggggaacgtcttctcatgctccgtgatgcatgaggctct gcacaaccactacacgcagaagagcctctccctgtctcctggtaaa (Human TGFβRII)
atccccccccacgtgcagaagtccgttaacaacgacatgatcgtgaccga caacaacggcgccgtgaagttcccccagctgtgcaagttctgcgacgtga ggttctccacctgcgacaaccagaagtcctgcatgtccaactgctccatc acctccatctgcgagaagcctcaggaggtgtgcgtggctgtgtggcggaa gaacgacgagaacatcaccctggagaccgtgtgccacgaccccaagctgc cctaccacgacttcatcctggaggacgccgcctcccccaagtgcatcatg aaggagaagaagaagcccggcgagaccttctttatgtgctcctgctccag cgacgagtgcaacgacaacatcatcttctccgaggagtacaacacctcca accccgac
```

The amino acid sequence of the anti-PDL1/IL-15RαSu/Fc/TGFβRII fusion protein (including signal peptide sequence) is as follows (SEQ ID NO: 12):

```
(Signal peptide)
MKWVTFISLLFLFSSAYS (anti-PDL1 single chain)

(anti-PDL1 light chain variable domain)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (anti-PDL1 heavy chain variable domain)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (Human IL-15R α sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK (Human TGFβRII)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD
```

C2B: Anti-PDL1/IL-15RαSu/Fc/TGFβRII with Linker:
The nucleic acid sequence of the anti-PDL1/IL-15RαSu/Fc/TGFβRII construct with linker (including signal peptide sequence) is as follows (SEQ ID NO: 13):

```
(Signal peptide)
atgaagtgggtgaccttcatcagcctgctgttcctgttctccagcgccta ctcc anti-PDL1 single chain (anti-PDL1 light chain variable domain)
aacatccagatgacccagtcccctagctccgtgtccgcctccgtgggaga tcgggtgaccatcacctgtagggcctcccaggacatctccaggtggctgg cctggtaccagcagaagcccggcaaggcccccaagctgctgatctacgcc gcctcctccctgcagtccggagtgcctagcaggttctccggctccggatc cggcacagacttcgccctgaccatctcctccctgcagcccgaggacttcg ccacctactactgccagcaggccgactccaggttctccatcaccttcggc cagggcaccaggctggagatcaagagg Linker)
ggaggtggcggatccggaggtggaggttctggtggaggtgggagt (anti-PDL1 heavy chain variable domain)
gaggtgcagctggtgcagtccggaggaggactggtgcagcctggcggatc cctgaggctgtcctgtgccgcttccggcttcaccttcagctcctactcca tgaactgggtgaggcaggcccctggaaagggcctggagtgggtgtcctac atctccagctcctcctccaccatccagtacgccgactccgtgaagggcag gttcaccatctccagggacaacgccaagaactccctgtacctgcagatga acagcctgagggacgaggacaccgccgtgtactactgcgccaggggcgac tattactacggcatggacgtgtggggccagggaaccaccgtgaccgtgtc ctcc (Human IL-15R α sushi domain)
atcacgtgtcctcctcctatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgcattaga (Human IgG1 CH2-CH3 (Fc) domain)
gagccgaaatcttgtgacaaaactcacacatgcccaccgtgcccagcacc tgaactcctggggggaccgtcagtcttcctcttccccccaaaacccaagg acaccctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca cgtaccgtgtggtcagcgtcctcaccgtcctgcaccaggactggctgaat ggcaaggagtacaagtgcaaggtctccaacaaagccctcccagcccccat cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc
```

```
                                    -continued
aggtggcagcaggggaacgtcttctcatgctccgtgatgcatgaggctct gcacaaccactacacgcagaagagcctctccctgtctcctggtaaa (Linker)
ggaggaggtggctccggaggcggtggctccggtggaggtggctccggagg tggcggttccggt (Human TGFβRII)
atcccccccacgtgcagaagtccgttaacaacgacatgatcgtgaccga caacaacggcgccgtgaagttcccccagctgtgcaagttctgcgacgtga ggttctccacctgcgacaaccagaagtcctgcatgtccaactgctccatc acctccatctgcgagaagcctcaggaggtgtgcgtggctgtgtggcgaa gaacgacgagaacatcaccctggagaccgtgtgccacgaccccaagctgc cctaccacgacttcatcctggaggacgccgcctcccccaagtgcatcatg aaggagaagaagaagcccggcgagaccttctttatgtgctcctgctccag cgacgagtgcaacgacaacatcatcttctccgaggagtacaacacctcca accccgac
```

The amino acid sequence of the anti-PDL1/IL-15RαSu/Fc/TGFβRII with linker fusion protein (including signal peptide sequence) is as follows (SEQ ID NO: 14):

```
(Signal peptide)
MKWVTFISLLFLFSSAYS (anti-PDL1 single chain)
(anti-PDL1 light chain variable domain)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (anti-PDL1 heavy chain variable domain)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (Human IL-15R α sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK(Linker)GGGGSGGGGS

GGGGSGGGGSG (Human TGFβRII)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD
```

Co-Transfection and Protein Purification:

The IL-15N72D and αPDL1/IL-15RαSu/Fc/TGFβRII constructs were cloned into expression vectors as described previously (U.S. Pat. No. 8,507,222, at Example 1, incorporated herein by reference), and the expression vectors were transfected into CHO cells. Co-expression of the two constructs in CHO cells allowed for formation and secretion of the soluble IL-15N72D: αPDL1/IL-15RαSu/Fc/TGFβRII fusion protein complex (referred to as αPDL1/TxM/TGFβRII), which can be purified by Protein A affinity and other chromatography methods and analyzed by SDS-PAGE and SEC methods to confirm purity and appropriate banding patterns (FIG. 22).

In some cases, the leader peptide is cleaved from the intact polypeptide to generate the mature form that may be soluble or secreted.

Other sequences of the invention include:

```
2x-TGFβRII-IL15(N72D) (SEQ ID NO: 15):
atgaagtgggtgaccttcatcagcctgctgttcctgttctccagcgccta ctccatccccccccatgtgcaaaagagcgtgaacaacgatatgatcgtga ccgacaacaacggcgccgtgaagtttccccagctctgcaagttctgcgat gtcaggttcagcacctgcgataatcagaagtcctgcatgtccaactgcag catcacctccatctgcgagaagcccccaagaagtgtgcgtggccgtgtggc ggaaaaatgacgagaacatcaccctggagaccgtgtgtcacgaccccaag ctcccttatcacgacttcattctggaggacgctgcctcccccaaatgcat catgaaggagaagaagaagcccggagagaccttctttatgtgttcctgta gcagcgacgagtgtaacgacaacatcatcttcagcgaagagtacaacacc agcaaccctgatggaggtggcggatccggaggtggaggttctggtggagg tgggagtattcctccccacgtgcagaagagcgtgaataatgacatgatcg tgaccgataacaatggcgccgtgaaatttccccagctgtgcaaattctgc gatgtgaggttttccacctgcgacaaccagaagtcctgtatgagcaactg ctccatcacctccatctgtgagaagcctcaggaggtgtgcgtggctgtct ggcggaagaatgacgagaatatcaccctggaaaccgtctgccacgatccc aagctgccctaccacgatttcatcctggaagacgccgccagccctaagtg catcatgaaagagaaaaagaagcctggcgagacctttttcatgtgctcct gcagcagcgacgaatgcaacgacaatatcatctttagcgaggaatacaat accagcaacccgacaactgggtgaatgtaataagtgatttgaaaaaaat tgaagatcttattcaatctatgcatattgatgctactttatatacggaaa gtgatgttcaccccagttgcaaagtaacagcaatgaagtgctttctcttg gagttacaagttatttcacttgagtccggagatgcaagtattcatgatac agtagaaatctgatcatcctagcaaacgacagtttgtcttctaatggga atgtaacagaatctggatgcaaagaatgtgaggaactggaggaaaaaaat attaaagaattttttgcagagttttgtacatattgtccaaatgttcatcaa cacttcttaa
```

```
TGFβRII-IgG1-Fc (SEQ ID NO: 16):
atgaagtgggtgaccttcatcagcctgctgttcctgttctccagcgccta ctccatccccccccatgtgcaaaagagcgtgaacaacgatatgatcgtga ccgacaacaacggcgccgtgaagtttccccagctctgcaagttctgcgat
```

-continued
gtcaggttcagcacctgcgataatcagaagtcctgcatgtccaactgcac gatcacctccatctgcgagaagccccaagaagtgtgcgtggccgtgtggc ggaaaaatgacgagaacatcaccctggagaccgtgtgtcacgaccccaag ctcccttatcacgacttcattctggaggacgctgcctcccccaaatgcat catgaaggagaagaagaagcccggagagaccttctttatgtgttcctgta gcagcgacgagtgtaacgacaacatcatcttcagcgaagagtacaacacc agcaaccctgatgagcccaaatcttgtgacaaaactcacacatgcccacc gtgcccagcacctgaactcctgggggaccgtcagtcttcctcttcccc caaaacccaaggacaccctcatgatctcccggaccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag aaccacaggtgtacaccctgcccccatcccgggatgagctgaccaagaac caggtcagcctgacctgcctggtcaaaggcttctatcccagcgacatcgc cgtggagtgggagagcaatgggcagccggagaacaactacaagaccacgc ctcccgtgctggactccgacggctccttcttcctctacagcaagctcacc gtggacaagagcaggtggcagcaggggaacgtcttctcatgctccgtgat gcatgaggctctgcacaaccactacacgcagaagagcctctccctgtctc cgggtaaataa TGFβRII-Dimer-IL15RaSu-IgG1-Fc (SEQ ID NO: 17):
atgaagtgggtgaccttcatcagcctgctgttcctgttctccagcgccta ctccatccccccccatgtgcaaaagagcgtgaacaacgatatgatcgtga ccgacaacaacggcgccgtgaagtttccccagctctgcaagttctgcgat gtcaggttcagcacctgcgataatcagaagtcctgcatgtccaactgcac gatcacctccatctgcgagaagccccaagaagtgtgcgtggccgtgtggc ggaaaaatgacgagaacatcaccctggagaccgtgtgtcacgaccccaag ctcccttatcacgacttcattctggaggacgctgcctcccccaaatgcat catgaaggagaagaagaagcccggagagaccttctttatgtgttcctgta gcagcgacgagtgtaacgacaacatcatcttcagcgaagagtacaacacc agcaaccctgatggaggtggcggatccggaggtggaggttctggtggagg tgggagtattcctccccacgtgcagaagagcgtgaataatgacatgatcg tgaccgataacaatggcgccgtgaaatttccccagctgtgcaaattctgc gatgtgaggttttccacctgcgacaaccagaagtcctgtatgagcaactg cacaatcacctccatctgtgagaagcctcaggaggtgtgcgtggctgtct ggcggaagaatgacgagaatatcaccctggaaaccgtctgccacgatccc aagctgccctaccacgatttcatcctggaagacgccgccagccctaagtg catcatgaaagagaaaaagaagcctggcgagaccttttttcatgtgctcct gcagcagcgacgaatgcaacgacaatatcatctttagcgaggaatacaat accagcaaccccgacatcacgtgtcctcctcctatgtccgtggaacacgc -continued
agacatctgggtcaagagctacagcttgtactccagggagcggtacattt gtaactctggtttcaagcgtaaagccggcacgtccagcctgacggagtgc gtgttgaacaaggccacgaatgtcgcccactggacaaccccagtctcaa atgtattagagagcccaaatcttgtgacaaaactcacacatgcccaccgt gcccagcacctgaactcctgggggaccgtcagtcttcctcttccccca aaacccaaggacaccctcatgatctcccggaccctgaggtcacatgcgt ggtggtggacgtgagccacgaagaccctgaggtcaagttcaactggtacg tggacggcgtggaggtgcataatgccaagacaaagccgcgggaggagcag tacaacagcacgtaccgtgtggtcagcgtcctcaccgtcctgcaccagga ctggctgaatggcaaggagtacaagtgcaaggtctccaacaaagccctcc cagcccccatcgagaaaaccatctccaaagccaaagggcagccccgagaa ccacaggtgtacaccctgcccccatcccgggatgagctgaccaagaacca ggtcagcctgacctgcctggtcaaaggcttctatcccagcgacatcgccg tggagtgggagagcaatgggcagccggagaacaactacaagaccacgcct cccgtgctggactccgacggctccttcttcctctacagcaagctcaccgt ggacaagagcaggtggcagcaggggaacgtcttctcatgctccgtgatgc atgaggctctgcacaaccactacacgcagaagagcctctccctgtctccg ggtaaataa IL15 (N72D) (SEQ ID NO: 18):
Aactgggtgaatgtaataagtgatttgaaaaaaattgaagatcttatcca gtccatgcacatcgacgccacccctgtacaccgagagcgacgtgcacccct cctgcaaggtgaccgccatgaagtgcttcctgctggagctgcaggtgatc tccctggagtccggcgacgcctccatccacgacaccgtggagaacctgat catcctggccaacgactccctgtcctccaacggcaacgtgaccgagtccg gctgcaaggagtgcgaggagctggaggagaagaacatcaaggagttcctg cagtccttcgtgcacatcgtccaaatgttcatcaacacttct αPD-L1/SuFc/TGF-β (SEQ ID NO: 19):
atggaatggagctgggtctttctcttcttcctgtcagtaaccaccggtgt ccactccaacatccagatgacccagtctccatcttctgtgtctgcatctg taggagacagagtcaccatcacttgtcggcgagtcaggatattagccgc tggttagcctggtatcagcagaaaccagggaaagcccctaaactcctgat ctatgctgcatccagtttgcaaagtggggtcccatcgaggttcagcggca gtggatctgggacagatttcgctctcactatcagcagcctgcagcctgaa gattttgcaacttactattgtcaacaggctgacagtcgtttctcgatcac cttcggccaagggacacgactggagattaaacgaggaggtggcggatccg gaggtggaggttctggtggaggtgggagtgaggtgcagctggtgcagtct gggggaggcttggtacagcctggggggtccctgagactctcctgtgcagc ctctggattcaccttcagtagctatagcatgaactgggtccgccaggctc cagggaaggggctggagtgggtttcatacattagtagtagtagtagtacc atacagtacgcagactctgtgaagggccgattcaccatctccagagacaa tgccaagaactcactgtatctgcaaatgaacagcctgagagacgaggaca

```
cggctgtgtattactgtgcgagaggggactactactacggtatggacgtc tggggccaagggaccacggtcaccgtgagctcaatcacgtgtcctcctcc tatgtccgtggaacacgcagacatctgggtcaagagctacagcttgtact ccagggagcggtacatttgtaactctggtttcaagcgtaaagccggcacg tccagcctgacggagtgcgtgttgaacaaggccacgaatgtcgcccactg gacaaccccagtctcaaatgcattagagagccgaaatcttgtgacaaaa ctcacacatgcccaccgtgcccagcacctgaactcctgggggaccgtca gtcttcctcttccccccaaaacccaaggacaccctcatgatctcccggac ccctgaggtcacatgcgtggtggtggacgtgagccacgaagaccctgagg tcaagttcaactggtacgtggacggcgtggaggtgcataatgccaagaca aagccgcgggaggagcagtacaacagcacgtaccgtgtggtcagcgtcct caccgtcctgcaccaggactggctgaatggcaaggagtacaagtgcaagg tctccaacaaagccctcccagcccccatcgagaaaaccatctccaaagcc aaagggcagccccgagaaccacaggtgtacaccctgcccccatcccggga tgagctgaccaagaaccaggtcagcctgacctgcctggtcaaaggcttct atcccagcgacatcgccgtggagtgggagagcaatgggcagccggagaac aactacaagaccacgcctcccgtgctggactccgacggctccttcttcct ctacagcaagctcaccgtggacaagagcaggtggcagcaggggaacgtct tctcatgctccgtgatgcatgaggctctgcacaaccactacacgcagaag agcctctccctgtctccggtaaaggaggaggtggctccggaggcggtgg ctccggtggaggtggctccggaggtggcggttccggtatccccccccacg tgcagaagtccgttaacaacgacatgatcgtgaccgacaacaacggcgcc gtgaagttcccccagctgtgcaagttctgcgacgtgaggttctccacctg cgacaaccagaagtcctgcatgtccaactgcccaatcacctccatctgcg agaagcctcaggaggtgtgcgtggctgtgtggcggaagaacgacgagaac atcaccctggagaccgtgtgccacgaccccaagctgccctaccacgactt catcctggaggacgccgcctcccccaagtgcatcatgaaggagaagaaga agcccggcgagaccttctttatgtgctcctgctccagcgacgagtgcaac gacaacatcatcttctccgaggagtacaacacctccaaccccgactga
```

In addition, the fusion proteins described above can also comprise the sequence of wild type IL-15 instead of the IL-15N72D variant. For example, the nucleic acid sequences above encoding the IL-15N72D domains could be substituted with nucleic acid sequences encoding wild type IL-15. Nucleic acid sequences of the invention could be native sequences or those optimized for expression in the host cells, i.e., codon optimized sequences.

```
The amino acid sequence of the wild type IL15
protein domain is as follows:
(Human IL-15)
                                            (SEQ ID NO: 20)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

N-810 A
The amino acid sequence of the N-810A (αPD-L1
Light Chain Fv/Linker/αPD-L1 HeavyChain
Fv/Linker/IL15RαSuFc/Linker/TGFβRII)
protein is as follows:
(IL-15 (N72D))
                                            (SEQ ID NO: 21)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS (αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVT

VSS (IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMQNCPI

TSICEKPQEVCVAVWRKQDENITLETVCHDPKLPYHDFILEDAASPKCIM

KEKKKPGETFFMCSCSSDECNDNIIFSEEYQTSNPD.
```

The amino acid of N-810A aglycosylated TGFβRII* (αPD-L1 Light Chain Fv/Linker/αPD-L1 Heavy Chain Fv/Linker/IL15RαSuFc/Linker/TGFβRII) (SEQ ID NO: 22) is as follows:

```
(IL-15 (N72D))
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS (αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR
```

(Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVT

VSS (IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMQNCPI

TSICEKPQEVCVAVWRKQDENITLETVCHDPKLPYHDFILEDAASPKCIM

KEKKKPGETFFMCSCSSDECNDNIIFSEEYQTSNPD.

The amino acid of N-810A aglycosylated TGFβRII+Δfree cysteine* (αPD-L1 Light Chain Fv/Linker/αPD-L1 Heavy Chain Fv/Linker/IL15RαSuFc/Linker/TGFβRII) (SEQ ID NO: 23) is as follows:

((IL-15 (N72D))
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS (αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (IL15RαSuFc)
ITCPPPMSVEHADIWVKSYSLYSRERYICNSGFKRKAGTSSLTECVLNKA

TNVAHWTTPSLKCIREPKSSDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMQNCPI

TSICEKPQEVCVAVWRKQDENITLETVCHDPKLPYHDFILEDAASPKCIM

KEKKKPGETFFMCSCSSDECNDNIIFSEEYQTSNPD.

The amino acid of N-810A Δ hinge** (αPD-L1 Light Chain Fv/Linker/αPD-L1 Heavy Chain Fv/Linker/IL15RαSuFc/Linker/TGFβRII) (SEQ ID NOS 24 and 46 with the "EPKSC" region of the IL15RαSuFc sequence deleted and included, respectively) is as follows:

((IL-15 (N72D))
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS (αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (IL15RαSuFc)
ITCPPPMSVEHADIWVKSYSLYSRERYICNSGFKRKAGTSSLTECVLNKA

TNVAHWTTPSLKCIRDKTHTCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMNNCPI

TSICEKPQEVCVAVWRKNDENITLETVCHDPKLPYHDFILEDAASPKCIM

KEKKKPGETFFMCSCSSDECNDNIIFSEEYNTSNPD.

The amino acid of N-810A+(IL15-K41Q, L45S, I67T, N79Y, E93A)* (αPD-L1 Light Chain Fv/Linker/αPD-L1 Heavy Chain Fv/Linker/IL15RαSuFc/Linker/TGFβRII) (SEQ ID NO: 25) is as follows:

(IL-15-K41Q, L45S, I67T, N79Y, E93A)
NWVNVISDLKKIEDLIQSMHIDATLYTESDVHPSCKVTAMQCFLSELQVI

SLESGDASIHDTVENLTILANDSLSSNGYVTESGCKECEELEAKNIKEFL

QSFVHIVQMFINTS (αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMSNCPI

TSICEKPQEVCVAVWRKNDENITLETVCHDPKLPYHDFILEDAASPKCIM

KEKKKPGETFFMCSCSSDECNDNIIFSEEYNTSNPD.

The amino acid of N-810A+(IL15-L45S)* (αPD-L1 Light Chain Fv/Linker/αPD-L1 Heavy Chain Fv/Linker/IL15RαSuFc/Linker/TGFβRII) (SEQ ID NO: 26) is as follows:

(IL15-L45S)
NWVNVISDLKKIEDLIQSMHIDATLYTESDVHPSCKVTAMKCFL<u>S</u>ELQVI

SLESGDASIHDTVENLIILANDSLSSNGNVTESGCKECEELEEKNIKEFL

QSFVHIVQMFINTS (αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVT

VSS (IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMSNCPI

TSICEKPQEVCVAVWRKNDENITLETVCHDPKLPYHDFILEDAASPKCIM

KEKKKPGETFFMCSCSSDECNDNIIFSEEYNTSNPD (αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS ((IL-15 (N72D))
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

IL15RαSuFc/Linker/TGFβRII (SEQ ID NO: 28):
(IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMSNCPI

TSICEKPQEVCVAVWRKNDENITLETVCHDPKLPYHDFILEDAASPKCIM

KEKKKPGETFFMCSCSSDECNDNIIFSEEYNTSNPD

N-810D
αPD-L1 Light Chain Fv/Linker/αPD-L1 Heavy Chain Fv/IL-15 (N72D) (SEQ ID NO: 27):
N-810D Aglycosylated TGFβRII*
αPD-L1 Light Chain Fv/Linker/αPD-L1 Heavy Chain Fv/IL-15 (N72D) (SEQ ID NO: 29) is as follows:

(αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR

-continued (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS ((IL-15 (N72D))
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

IL15RαSuFc/Linker/TGFβRII (SEQ ID NO: 30):
(IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (Linker)
GGGGSGGGGSGGGGSGGGGSG (TGFβRII)
IPPHVQKSVNNDMIVTDNNGAVKFPQLCKFCDVRFSTCDNQKSCMQNCPI

TSICEKPQEVCVAVWRKQDENITLETVCHDPKLPYHDFILEDAASPKCIM

KEKKKPGETFFMCSCSSDECNDNIIFSEEYQTSNPD

N-810E
αPD-L1 Light Chain Fv/Linker/αPD-L1 Heavy Chain Fv/IL-15 (N72D) (SEQ ID NO: 31):

(αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS ((IL-15 (N72D))
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

TGFβRII/IL15RαSuFc (SEQ ID NO: 32):
(TGFβRII)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

N-810E Aglycosylated TGFβRII*
αPD-L1 Light Chain Fv/Linker/αPD-L1 Heavy Chain Fv/IL-15 (N72D) (SEQ ID NO: 33)

(αPD-L1 Light Chain Fv)
NIQMTQSPSSVSASVGDRVTITCRASQDISRWLAWYQQKPGKAPKLLIYA

ASSLQSGVPSRFSGSGSGTDFALTISSLQPEDFATYYCQQADSRFSITFG

QGTRLEIKR (Linker)
GGGGSGGGGSGGGGS (αPD-L1 Heavy Chain Fv)
EVQLVQSGGGLVQPGGSLRLSCAASGFTFSSYSMNWVRQAPGKGLEWVSY

ISSSSSTIQYADSVKGRFTISRDNAKNSLYLQMNSLRDEDTAVYYCARGD

YYYGMDVWGQGTTVTVSS (IL-15 (N72D))
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

TGFβRII/IL15RαSuFc (SEQ ID NO: 34):
(TGFβRII)
IPPHVQKSVNNDMIVTDNNGAVKFPQLCKFCDVRFSTCDNQKSCMQNCPI

TSICEKPQEVCVAVWRKQDENITLETVCHDPKLPYHDFILEDAASPKCIM

KEKKKPGETFFMCSCSSDECNDNIIFSEEYQTSNPD (IL15RαSuFc)
ITCPPPMSVEHADIWVKSYSLYSRERYICNSGFKRKAGTSSLTECVLNKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

*New point mutations are notated within sequence with underlined residue.**Deletions are denoted with a strikethrough. Final sequence does not include these residues. Note: All aglycosylated versions, mutated free cysteine and/or hinge deletion versions can alsobe combined with the IL15-K41Q, L45S, I67T, N79Y, E93A mutations.

Figure 9:
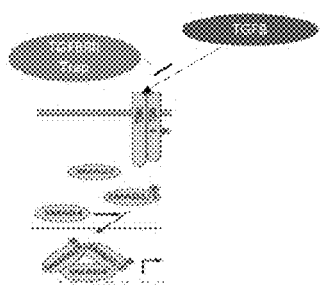
FIG. 9 is a table and a schematic representation of the early protein characterization.
Figure 10:
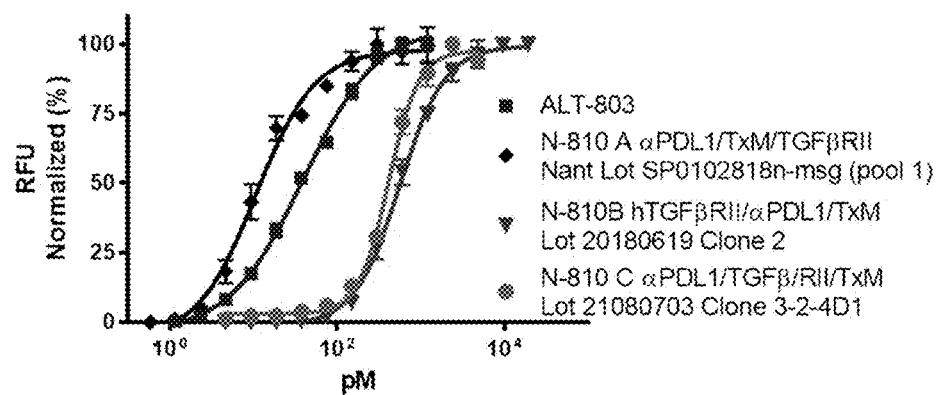
FIG. 10 is a graph and a table depicting results obtained using an IL-15 activity assay comparing αPDL1/TxM/TGFβRII, αPDL1/TGFβRII/TxM, TGFβRII/αPDL1/TxM and ALT-803.
Figure 10:
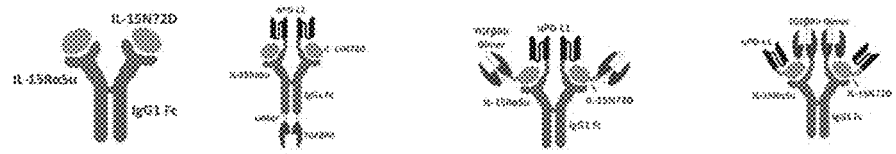
Figure 11:
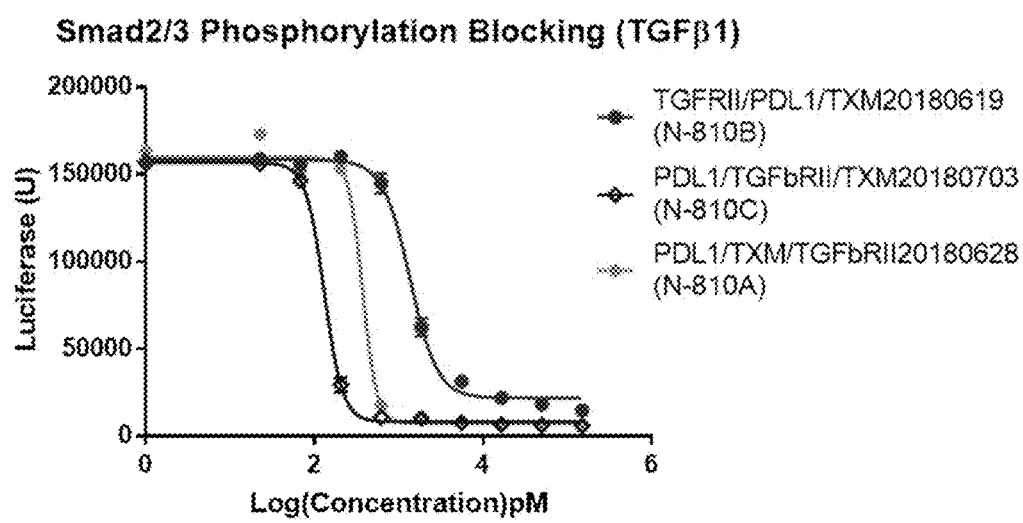
FIG. 11 is a graph and a table depicting results obtained using a TGFβ activity blocking assay comparing αPDL1/TxM/TGFβRII, TGFβRII/αPDL1/TxM and αPDL1/TGFβRII/TxM.
Figure 12:
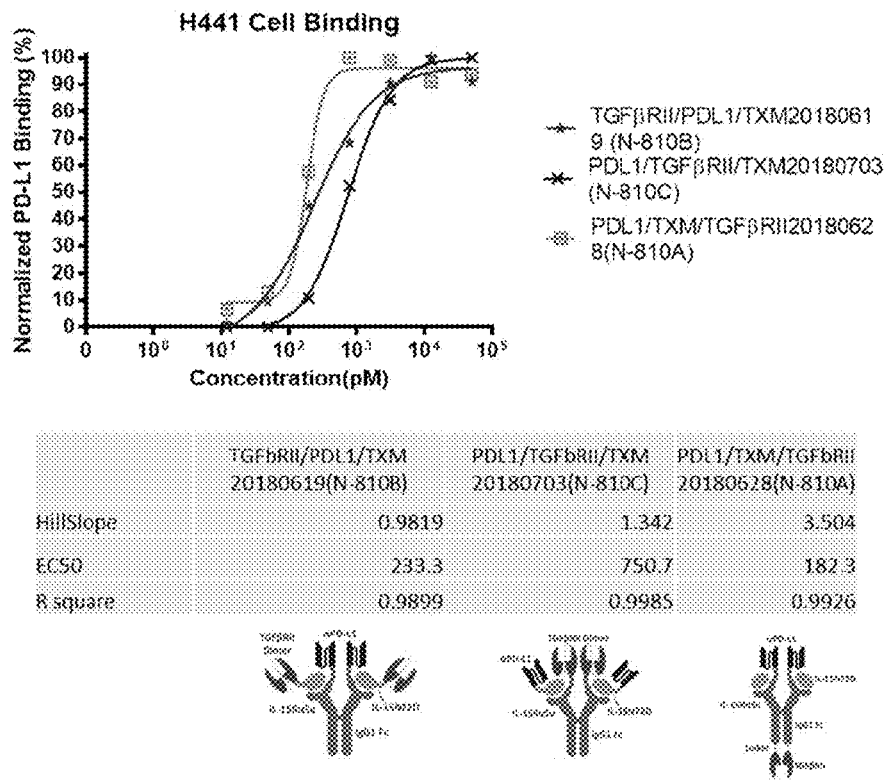
FIG. 12 is a graph and a table depicting results obtained using PDL1 binding assays comparing αPDL1/TxM/TGFβRII, TGFβRII/αPDL1/TxM, and αPDL1/TGFβRII/TxM.
Figure 13:
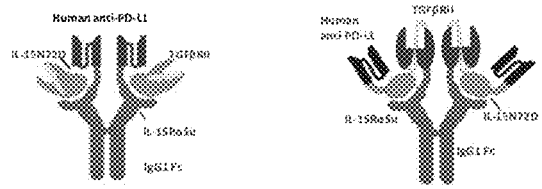
FIG. 13 is a table showing the overall comparison between TGFβRII/αPDL1/TXM and αPDL1/TGFβRII/TXM.
Figure 14A:
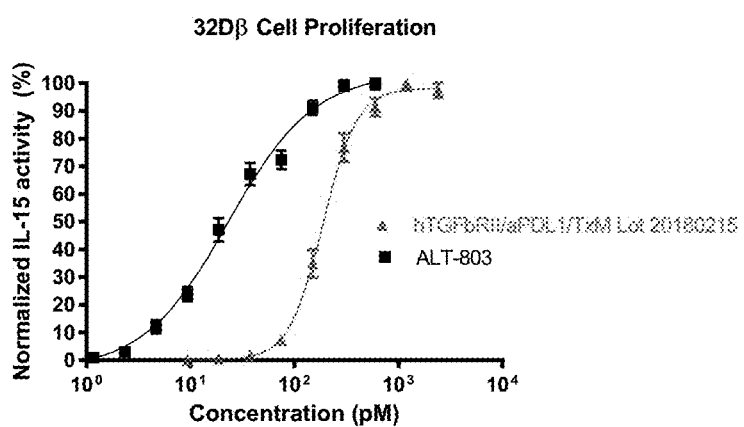
FIG. 14A is a graph showing cell proliferation after stimulation with hTGFβRII/αPDL1/TxM or ALT-803. IL-15 dependent 32D13 cells were stimulated for 3 days with hTGFβRII/αPDL1/TxM or ALT-803 and cell proliferation was assessed using PrestoBlue. The $EC_{50}$ of IL-15 was calculated by using ALT-803 as a positive control. The results that hαPDL1/TGFβRII/TxM has IL-15 activities, with an EC50 approximately 188 pM.
Figure 14B:
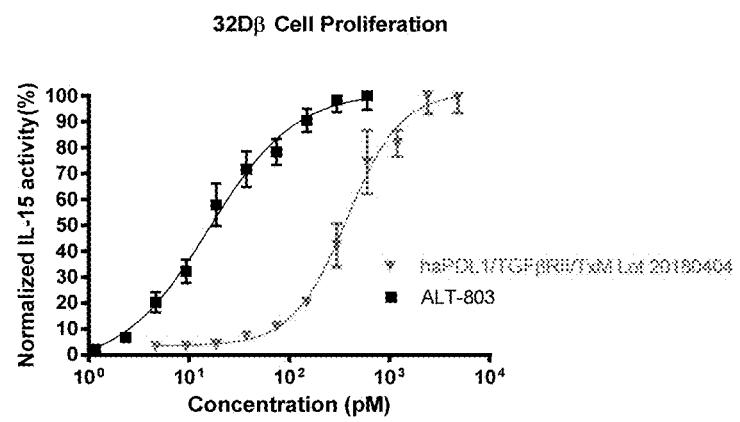
FIG. 14B is a graph showing cell proliferation after stimulation with hαPDL1/TGFβRII/TxM or ALT-803. IL-15 dependent 32D13 cells were stimulated for 3 days with hαPDL1/TGFβRII/TxM or ALT-803 and cell proliferation was assessed using PrestoBlue. The $EC_{50}$ of IL-15 was calculated by using ALT-803 as a positive control. The results that hαPDL1/TGFβRII/TxM has IL-15 activities, with an $EC_{50}$ approximately 376.5 pM.
Figure 15A:
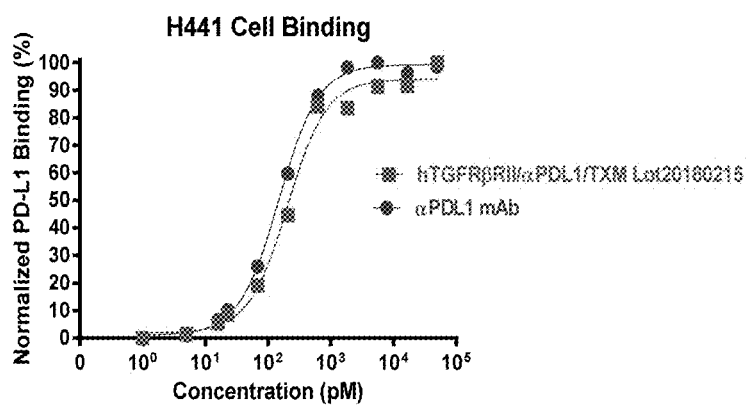
FIG. 15A is a graph showing results obtained from binding of TGFβRII/αPDL1/TxM to human lung papillary adenocarcinoma cells. Binding of TGFβRII/αPDL1/TxM to PDL1$^+$ H441 human lung papillary adenocarcinoma cells was analyzed by flow cytometry using APC labeled antibody specific for the Fc portion of hIgG. The results show TGFβRII/αPDL1/TxM has binding activity for PDL1.
Figure 15B:
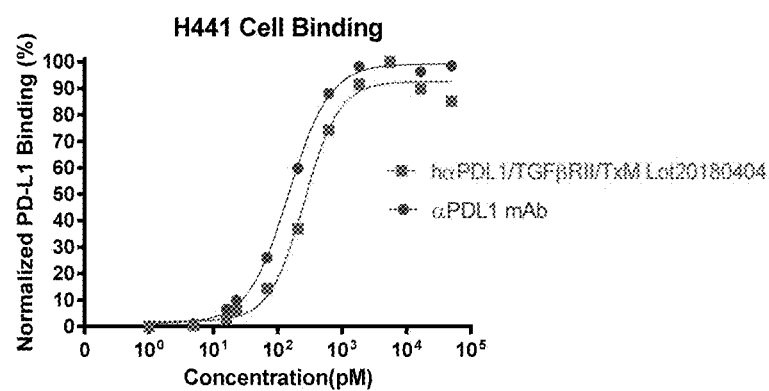
FIG. 15B is a graph showing results obtained from binding of hαPDL1/TGFβRII/TxM to human lung papillary adenocarcinoma cells. Binding of hαPDL1/TGFβRII/TxM to PDL1$^+$ H441 human lung papillary adenocarcinoma cells was analyzed by flow cytometry using APC labeled antibody specific for the Fc portion of hIgG. The results show that hαPDL1/TGFβRII/TxM has binding activity for PDL1.
Figure 16A:
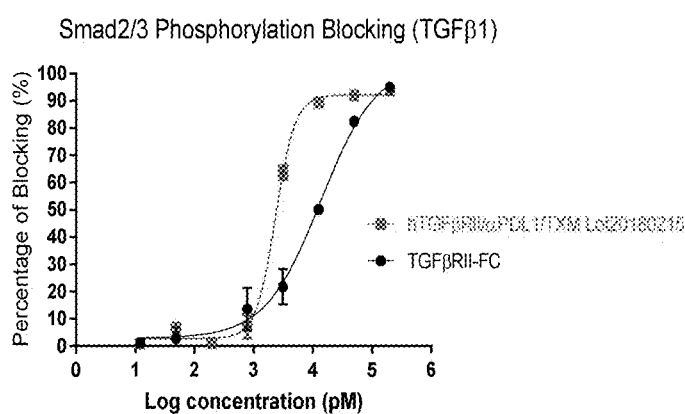
FIG. 16A is a graph showing results obtained from blocking of TGFβ1 mediated Smad2/3 phosphorylation by hTGFβRII/αPDL1/TxM. Blocking of Smad2/3 phosphorylation induced by TGFβ1 (100 ng/mL) using hTGFβRII/αPDL1/TxM was assessed with HEK293 cells containing TGF/SMAD Signaling Pathway SBE Reporter (BPS Bioscience). TGFβRII fused to IgG Fc was used as control. The results show that hTGFβRII/αPDL1/TxM can effectively block Smad phosphorylation mediated by TGFβ1, with a $IC_{50}$ approximately 2.35 nM.
Figure 16B:
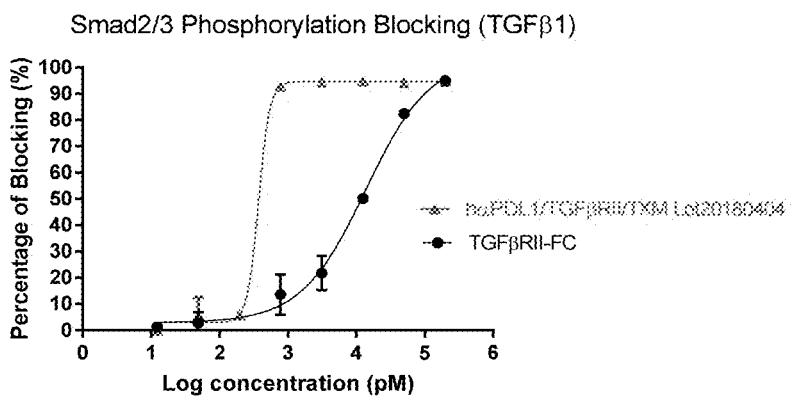
FIG. 16B is a graph showing results obtained from blocking of TGFβ1 mediated Smad2/3 phosphorylation by hαPDL1/TGFβRII/TxM. Blocking of Smad2/3 phosphorylation induced by TGFβ1 (100 ng/mL) using hαPDL1/TGFβRII/TxM was assessed with HEK293 cells containing TGF/SMAD Signaling Pathway SBE Reporter (BPS Bioscience). TGFβRII fused to IgG Fc was used as control. The results show that hαPDL1/TGFβRII/TxM can effectively block Smad phosphorylation mediated by TGFβ1, with a $IC_{50}$ approximately 0.38 nM.

Example 2. Biological Activities of Fusion Protein Complexes Comprising IL-15, Anti-PDL1, and TGFβRII Domains A variety of methods were used to characterize the biological activities of the complexes of the invention (FIG. 9)

IL-15 Immunostimulatory Activity:

The IL-15 immunostimulatory activity of the αPDL1/TxM/TGFβRII, TGFβRII/αPDL1/TXM and αPDL1/TGFβRII/TXM fusion protein complexes was assessed based on the proliferation of IL-15-dependent 32D3 cells, a mouse hematopoietic cell line. Increasing levels of αPDL1/TxM/TGFβRII, TGFβRII/αPDL1/TXM or αPDL1/TGFβRII/TXM were added to 32D13 cells ($10^4$ cell/well) in 200 μL RPMI: 10% FBS media and cells were incubated for 3 days at 37° C. PrestoBlue cell viability reagent (20 μL/well) was added then. After 4 hours, absorbance was measured at 570 nm (with a 600 nm reference wavelength for normalization) to determine cell proliferation based on reduction of PrestoBlue, a resazurin-based solution, by metabolically active cells. The half maximal effective concentration ($EC_{50}$) of IL-15 bioactivity for αPDL1/TxM/TGFβRII, TGFβRII/αPDL1/TXM and αPDL1/TGFβRII/TXM was then determined based on the relationship between absorbance and protein concentration. The bioactivity of ALT-803 was assessed as a positive control.

As shown in FIGS. 10, 13, 14A and 14B, the αPDL1/TxM/TGFβRII, TGFβRII/αPDL1/TXM and αPDL1/TGFβRII/TXM fusion protein complexes were capable of stimulating growth of 32D13 cells, demonstrating that these proteins retain IL-15 immunostimulatory activity.

Binding to PD-L:

Flow cytometry-based assays were used to assess binding of αPDL1/TxM/TGFβRII, TGFβRII/αPDL1/TXM and αPDL1/TGFβRII/TXM to PD-L1 in vitro. Specifically, serial dilutions of αPDL1/TxM/TGFβRII, TGFβRII/αPDL1/TXM, αPDL1/TGFβRII/TXM and anti-PD-L1 antibody controls were incubated with human H441 tumor cells expressing PD-L1 ($2.5 \times 10^5$ cells) in the dark on ice for 2 hours. The cells were then washed, resuspended and stained with APC Anti-Human IgG Fc Antibody (clone HP6017) in the dark at 4° C. for 30 minutes. After washing twice, cells were resuspended in 250 μl FACS buffer (1% BSA and 0.05% $NaN_3$ in phosphate buffered saline) and kept on ice until analyzed on BD FCSVerse flow cytometer with BD FD FCS Suite V1.0.6. The mean fluorescence intensity (MFI) was quantified for each concentration of protein.

As shown in FIGS. 12, 13, 15A and 15B. the αPDL1/TxM/TGFβRII, TGFβRII/αPDL1/TXM and αPDL1/TGFβRII/TXM fusion protein complexes were capable of binding PDL1 expressed on human tumor cells. Similarly, FIG. 22 shows the binding of the αPDL1/TxM/TGFβRII complex to PD-L1 by a surface plasmon resonance (SPR) assay.

Inhibition of TGFβ Activity:

TGFβ proteins bind to receptors on the cell surface, initiating a signaling cascade that leads to phosphorylation and activation of SMAD2 and SMAD3, which then form a complex with SMAD4. The SMAD complex then translocates to the nucleus and binds to the SMAD binding element (SBE) in the nucleus, leading to transcription and expression of TGF-β/SMAD responsive genes. The ability of the αPDL1/TxM/TGFβRII, TGFβRII/αPDL1/TXM and αPDL1/TGFβRII/TXM fusion protein complexes to inhibit TGF-β-induced Smad2/3 signaling was assessed.

HEK293 carrying TGFβ/SMAD signaling pathway SEB reporter (BPS Bioscience, #60653) were plated in a white clear-bottom 96-well microplate (Corning 3610) at a density of $5 \times 10^4$ cells per well in 100 μl of MEM medium, and incubated overnight at 37° C. and 5% $CO_2$. After 24 hours, wells were changed to 80 μl fresh assay medium and incubated at 37° C. and 5% CO2 for 4 hrs. Then 10 μl of serial dilutions of αPDL1/TxM/TGFβRII, TGFβRII/αPDL1/TXM, αPDL1/TGFβRII/TXM or TGFβRII-Fc control were added to each wall and incubated for 1 hour, following by addition of 10 μl recombinant human TGF-β1 or TGF-β3 (R&D Systems, 100 ng/mL) to each well to reach a total volume of 100 μl. After overnight incubation, 100 μl of ONE-Step™ Luciferase reagent (BPS Bioscience, #60690) was added and plates were incubated for at least 5 minutes at room temperature. Luminescence based on TGF-β-induced Smad2/3 signaling was measured using a GloMax Explorer plate reader (Promega). The half maximal inhibitory concentration ($EC_{50}$) of TGF-β-induced Smad2/3 signaling for αPDL1/TxM/TGFβRII, TGFβRII/αPDL1/TXM and αPDL1/TGFβRII/TXM was then determined based on the relationship between absorbance and protein concentration using Graphpad Prism7 software.

Figure 17A:
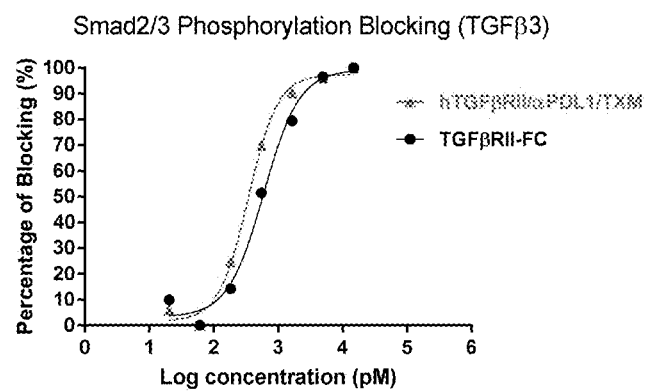
FIG. 17A is a graph showing results obtained from blocking of TGFβ1 mediated Smad2/3 phosphorylation by hTGFβRII/αPDL1/TxM. Blocking of Smad2/3 phosphorylation induced by TGFβ3 (100 ng/mL) using hTGFβRII/αPDL1/TxM was assessed with HEK293 cells containing TGF/SMAD Signaling Pathway SBE Reporter (BPS Bioscience). TGFβRII fused to IgG Fc was used as control. The results show that hTGFβRII/αPDL1/TxM can effectively block Smad phosphorylation mediated by TGFβ3, with a $IC_{50}$ approximately 0.355 nM.
Figure 17:
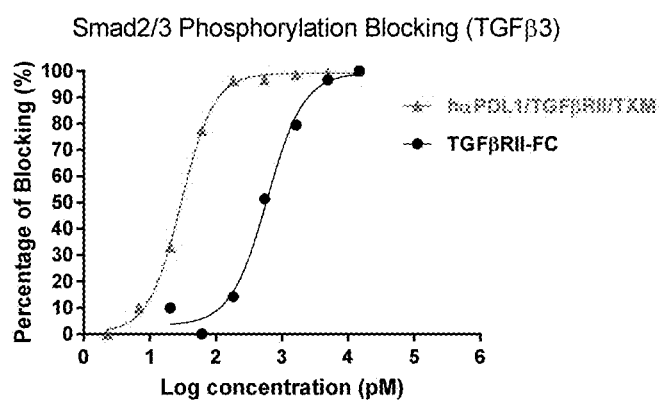
FIG. 17B is a graph showing results obtained from blocking of TGFβ3 mediated Smad2/3 phosphorylation by hαPDL1/TGFβRII/TxM. Blocking of Smad2/3 phosphorylation induced by TGFβ3 (100 ng/mL) using hαPDL1/TGFβRII/TxM was assessed with HEK293 cells containing TGF/SMAD Signaling Pathway SBE Reporter (BPS Bioscience). TGFβRII fused to IgG Fc was used as control. The results show that hαPDL1/TGFβRII/TxM can effectively block Smad phosphorylation mediated by TGFβ, with a $IC_{50}$ approximately 0.029 nM.
Figure 18A:
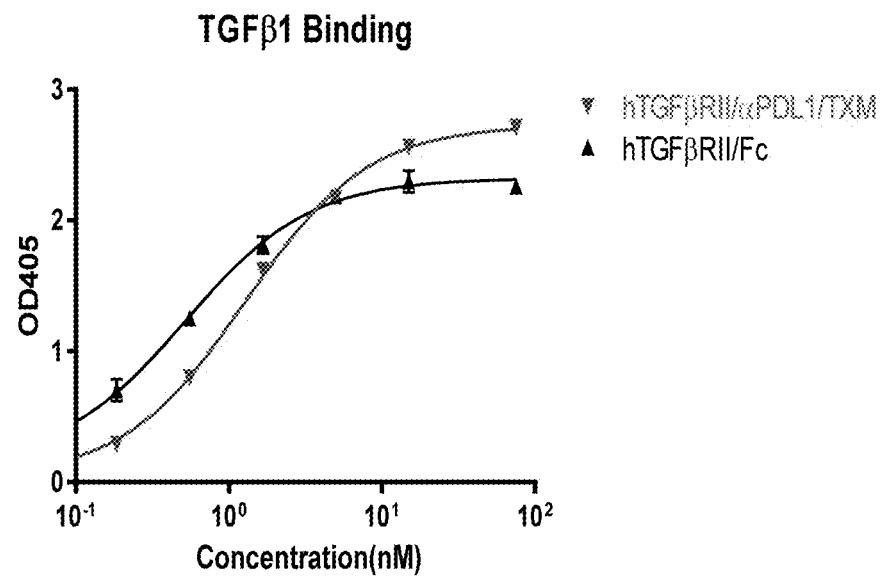
FIG. 18A is a graph showing results obtained from binding of hTGFβRII/αPDL1/TXM to TGF-β1. ELISAs were performed to assess binding of hTGFβRII/αPDL1/TXM to TGF-β1. Wells were first coated with TGFβ1 (0.5 μg/ml) overnight and then incubated with hTGFβRII/αPDL1/TXM in serial dilution. Protein binding was detected using anti-hIgG-horseradish peroxidase (HRP). The results show that hTGFβRII/αPDL1/TXM can bind to plate bound TGF-β1, with an EC50 of 1.28 nM.
Figure 18B:
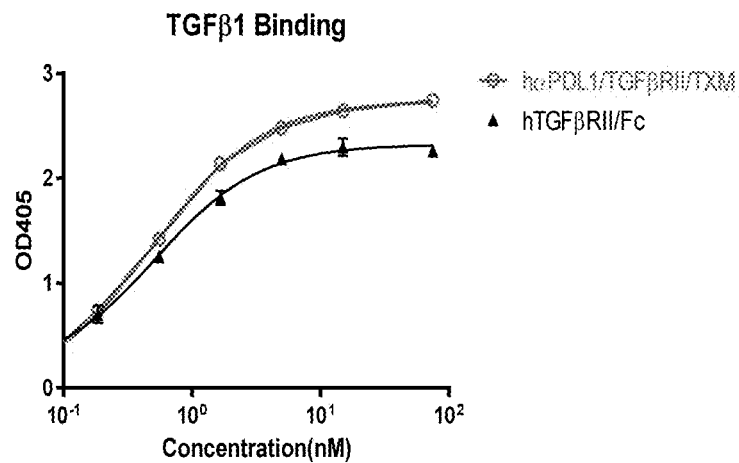
FIG. 18B is a graph showing results obtained from binding of hαPDL1/TGFβRII/TXM to TGF-β1. ELISAs were performed to assess binding of hαPDL1/TGFβRII/TXM to TGF-β1. Wells were first coated with TGFβ1 (0.5 ug/ml) overnight and then incubated with hαPDL1/TGFβRII/TXM in serial dilution. Protein binding was detected using anti-hIgG-horseradish peroxidase (HRP). The results show that hαPDL1/TGFβRII/TXM can bind to plate bound TGF-β1, with an EC50 of 0.49 nM.
Figure 19A:
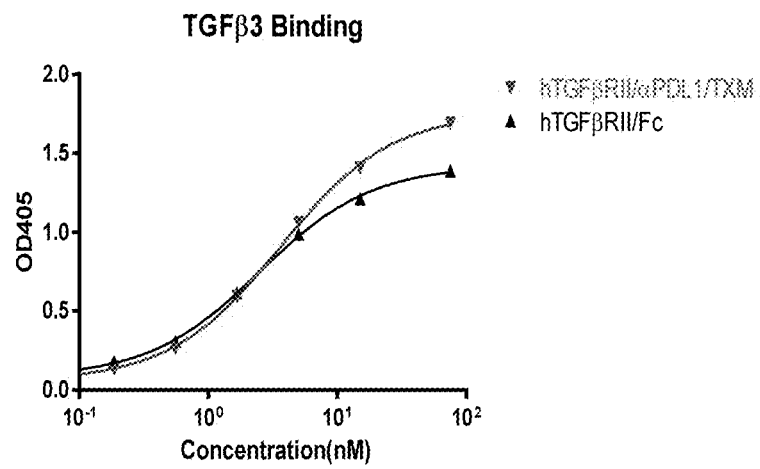
FIG. 19A is a graph showing results obtained from binding of hTGFβRII/αPDL1/TXM to TGF-β3. ELISAs were performed to assess binding of hTGFβRII/αPDL1/TXM to TGF-β1. Wells were first coated with TGFβ3 (0.5 μg/ml) overnight and then incubated with hTGFβRII/αPDL1/TXM in serial dilution. Protein binding was detected using anti-hIgG-horseradish peroxidase (HRP). The results show that hTGFβRII/αPDL1/TXM can bind to plate bound TGFβ, with an EC50 of 3.617 nM.
Figure 19B:
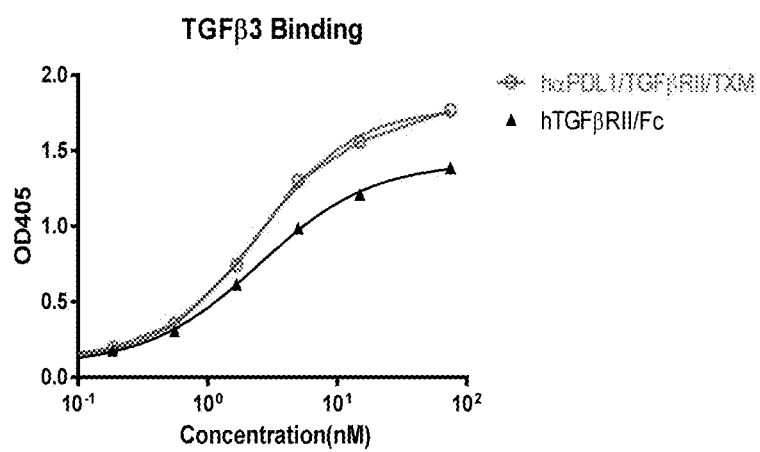
FIG. 19B is a graph showing results obtained from binding of hαPDL1/TGFβRII/TXM to TGF-β3. ELISAs were performed to assess binding of hαPDL1/TGFβRII/TXM to TGF-β3. Wells were first coated with TGFβ3 (0.5 μg/ml) overnight and then incubated with hαPDL1/TGFβRII/TXM in serial dilution. Protein binding was detected using anti-hIgG-horseradish peroxidase (HRP). The results show that hαPDL1/TGFβRII/TXM can bind to plate bound TGFβ, with an $EC_{50}$ of 2.447 nM.

As shown in FIGS. 11, 13, 16A, 16B, 17A and 17B, the αPDL1/TxM/TGFβRII, TGFβRII/αPDL1/TXM and αPDL1/TGFβRII/TXM fusion protein complexes were capable of inhibiting TGF-β1-induced Smad2/3 signaling. Similarly, the TGFβRII/αPDL1/TXM and αPDL1/TGFβRII/TXM fusion protein complexes were also capable of inhibiting TGF-03-induced Smad2/3 signaling (FIGS. 17A, 17B). Thus, these complexes act as TGF-β trap molecules and are expected to block the activities of TGF-β proteins. Notably, both the TGFβRII/αPDL1/TXM and αPDL1/TGFβRII/TXM fusion protein complexes showed greater inhibitory activity against TGF-β1 and TGF-β3 than the positive control TGFβRII-Fc protein.

Previously, it has been shown that proteins containing TGF-β trap domain had the ability to antagonize TGF-β 1-induced mesenchymalization in tumor cells (David, et al. 2017. OncoImmunology. 6:10, e1349589). The αPDL1/TxM/TGFβRII, TGFβRII/αPDL1/TXM and αPDL1/TGFβRII/TXM fusion protein complexes are anticipated to retain this biological activity. This can be assessed based on inhibition of TGF-β 1-mediated changes in tumor cell mesenchymal marker expression (i.e., vimentin, fibronectin), proliferation suppression, and chemotherapeutic resistance in vitro or in vivo as provided by David, et al.

Assessment of Protein Binding to TGFβ Proteins:

ELISA methods were used to assess the binding of TGFβRII/αPDL1/TXM and αPDL1/TGFβRII/TXM fusion protein complexes to TGFβ1 and TGFβ3. Specifically, 96-well ELISA plates (Nunc Maxisorb Immunoplate) were coated with TGFβ1 and TGFβ 3 in PBS with 10% CSF overnight at 4° C. The next day, plates were washed three times with wash buffer (PBS, 0.05% Tween-20) and blocked with 1% bovine serum albumin in PBS for 1 hour at room temperature. The plates were then incubated with serial dilutions TGFβRII/αPDL1/TXM, αPDL1/TGFβRII/TXM or TGFβRII-Fc control for 1 hour at room temperature. Following wash steps, protein binding was detected using anti-hIgG-horseradish peroxidase (HRP) (Jackson Immuno Research, 1:4,000 dilution) at room temperature for 30 minutes. Follow substrate development, absorbance was then read at 405 nm using a BioTek plate reader.

As shown in FIGS. 18A, 18B, 19A, and 19B, both the TGFβRII/αPDL1/TXM and αPDL1/TGFβRII/TXM fusion protein complexes were capable of binding TGFβ1 and TGFβ1, consistent with the TXM proteins ability to block TGFβ1- and TGFβ-mediated biological activity.

Figure 23:
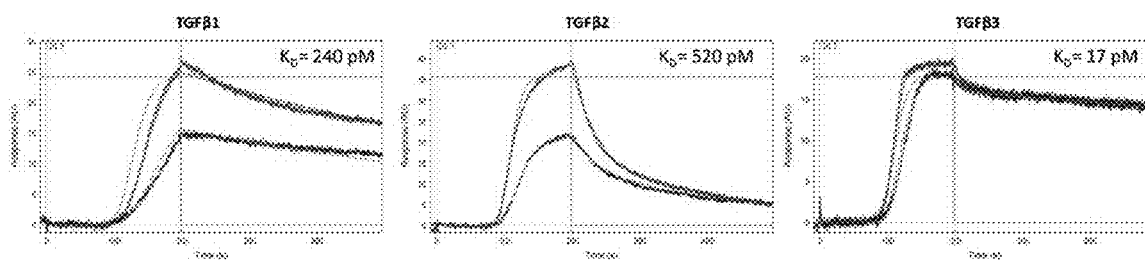
FIG. 23 is a series of plots showing a surface plasmon resonance (SPR) analysis of TGFβ3, TGFβ2 and TGFβ3 binding on αPDL1/TxM/TGFβRII. αPDL1/TxM/TGFβRII was immobilized onto the SPR sensor by Fc capture. Binding affinities to TGFβ1 (left panel), TGFβ2 (middle panel) and TGFβ3 (right panel) were determine by OneStep kinetic analysis on Pioneer FE (Fortebio).

Similarly, FIG. 23 shows the binding of the αPDL1/TxM/ TGFβRII complex to TGFβ1, TGFβ2 and TGFβ3 by a surface plasmon resonance (SPR) assay.

Antibody-Dependent Cellular Cytotoxicity Against PD-L-Positive Tumor Cells:

TGFβRII/αPDL1/TXM and αPDL1/TGFβRII/TXM proteins may be effective against tumor by inducing natural killer and CD8 T cell effector responses, blocking the immunosuppressive effects of TFG-β proteins or PD-1 checkpoint inhibitor and/or targeting immune responses against PD-L1 expressing tumor cells. To assess the ability of these proteins to mediate antibody-dependent cellular cytotoxicity against PD-L-positive tumor cells, Celltrace labeled PD-L-positive human H441 lung tumor cells ($2 \times 10^5$ cells) were cultured in duplicate with NK effector cells at a 1:10 ratio at 37° C. in the presence of different concentrations of TGFβRII/αPDL1/TXM, αPDL1/TGFβRII/TXM, anti-PD-L1 antibody, non-targeting TXM (101074/TXM) or other controls. After 20 hrs incubation, cells were harvested and resuspended in PI solution (2 µg/ml) to label dead cells. The percentage of dead Celltrace-positive PI-positive H441 tumor cells were then measured by flow cytometry.

Figure 20:
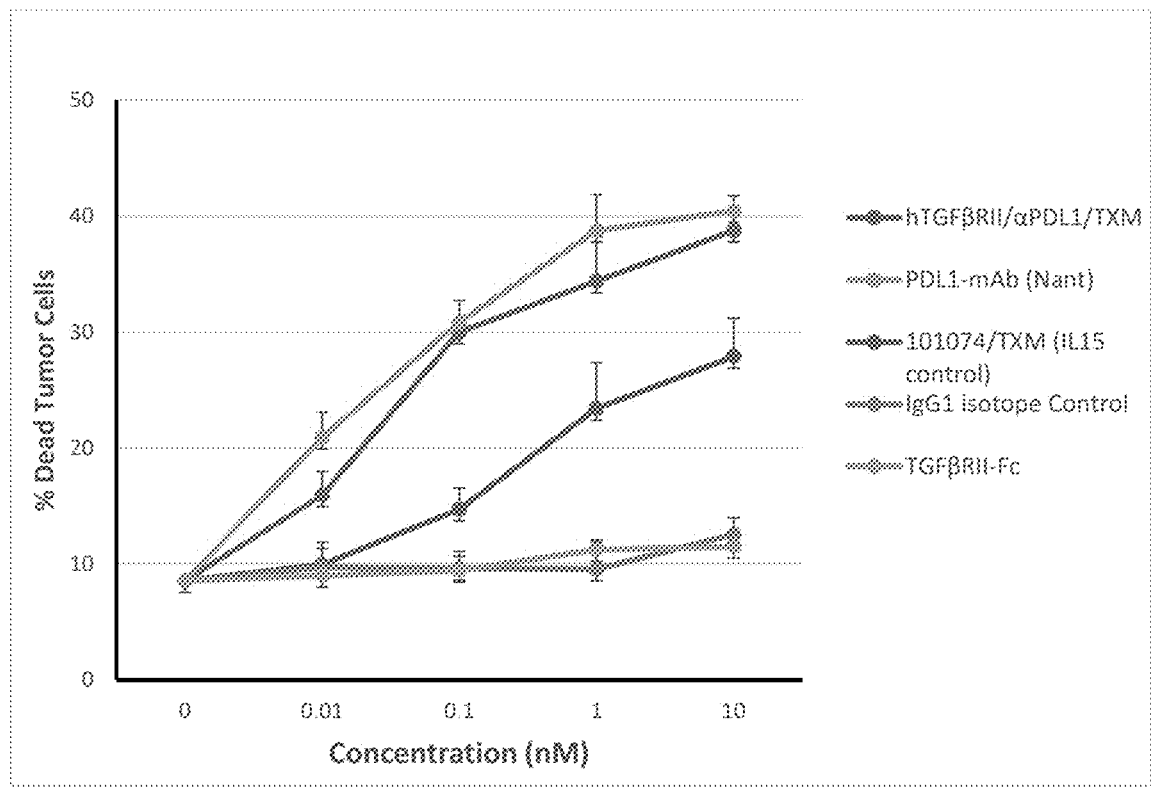
FIG. 20 is a graph showing results obtained from experiments assessing the anti-tumor activity of hTGFβRII/αPDL1/TXM. To assess the anti-tumor activity of hTGFβRII/αPDL1/TXM protein, CellTrace labeled PD-L1+ H441 lung tumor cells were incubated with human NK cells at E:T ratio of 10:1 for 20 hrs at 37 C in the presence of different proteins as indicated. Cells was then washed and resuspended in 2 μg/ml PI solution. The percentage of dead PI CellTrace H441 tumor cells was determined by flow cytometry and represents NK cell dependent killing of tumor cells mediated by the different proteins. The results showed that hTGFβRII/αPDL1/TXM protein can induce ADCC against tumor cells.
Figure 21:
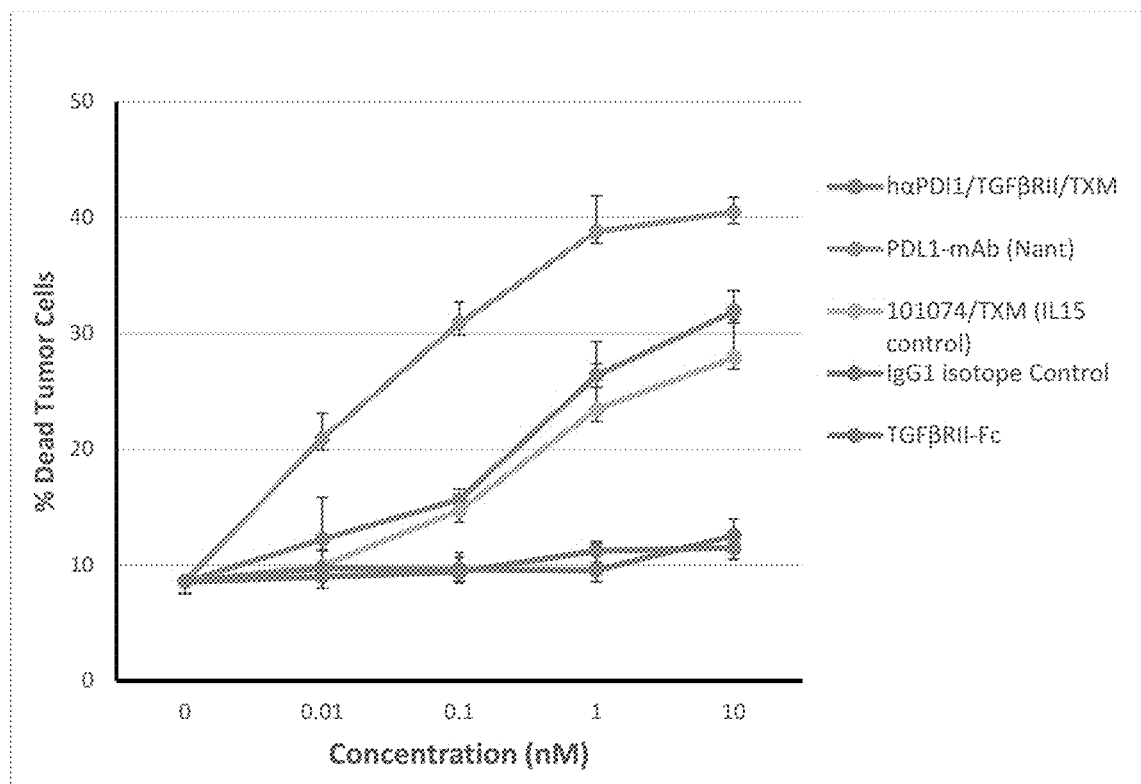
FIG. 21 is a graph showing results obtained from experiments assessing the anti-tumor activity of hαPDL1/TGFβRII/TXM. To assess the anti-tumor activity of hαPDL1/TGFβRII/TXM protein, CellTrace labeled PD-L1+ H441 lung tumor cells were incubated with human NK cells at E:T ratio of 10:1 for 20 hrs at 37° C. in the presence of different proteins as indicated. Cells was then washed and resuspended in 2 μg/ml PI solution. The percentage of dead PI+ CellTrace+ H441 tumor cells was determined by flow cytometry and represents NK cell dependent killing of tumor cells mediated by the different proteins. The results showed that hαPDL1/TGFβRII/TXM protein can induce ADCC against tumor cells.
Figures 22A, 22B:
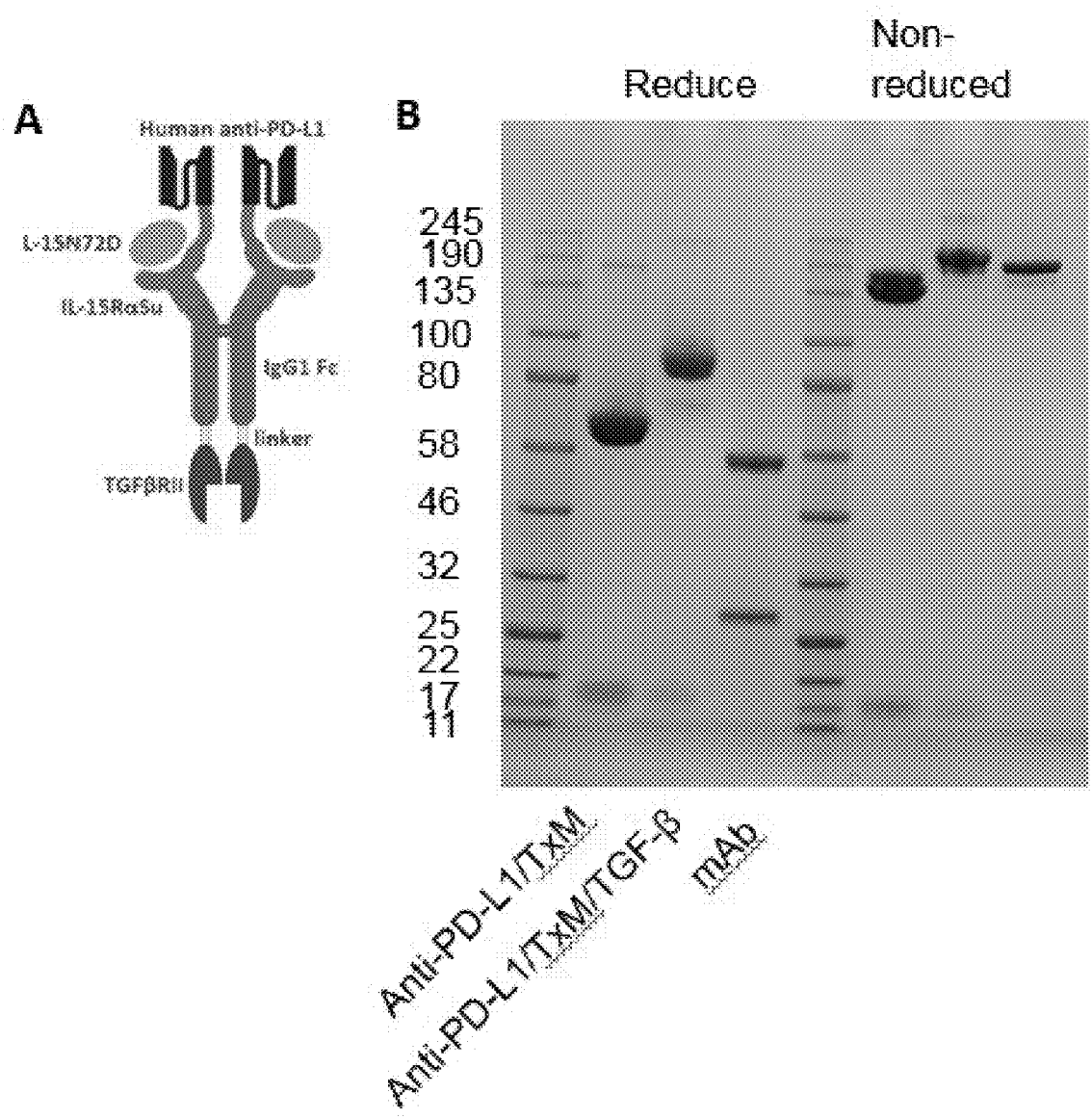
FIG. 22A is a schematic representation of the αPDL1/TxM/TGFβRII construct.
FIG. 22B: αPD-L1/TxM, αPDL1/TxM/TGFβRII, and a control antibody were run on SDS-PAGE in reduced (left) and non-reduced conditions (right).
Figure 22C:
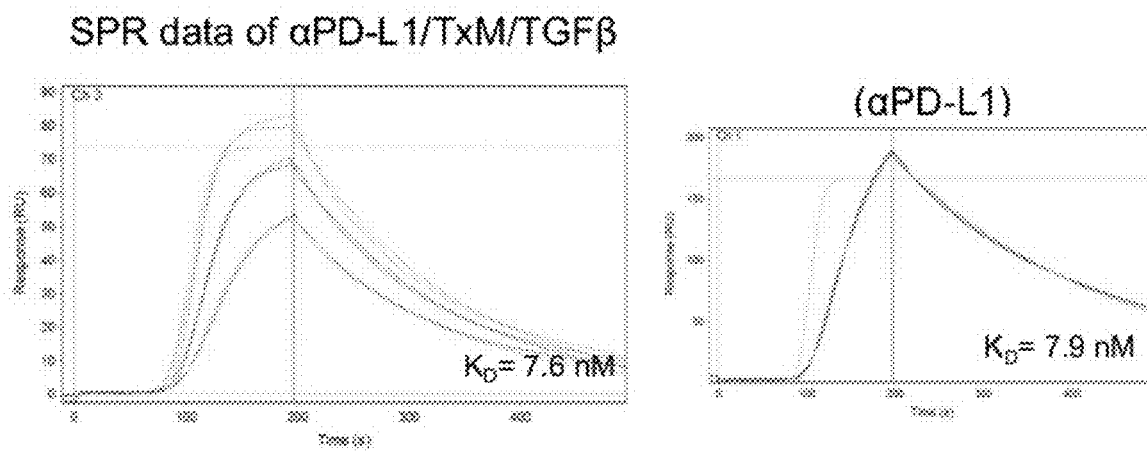
FIG. 22C is the SPR analysis of αPDL1/TxM/TGFβRII and Rsbc6 (αPDL1 Ab). αPDL1/TxM/TGFβRII and Rsbc6 were immobilized onto the SPR sensor by Fc capture. Binding affinity to PD-L1 was determined by OneStep kinetic analysis on Pioneer FE (Fortebio).
Figure 22D:
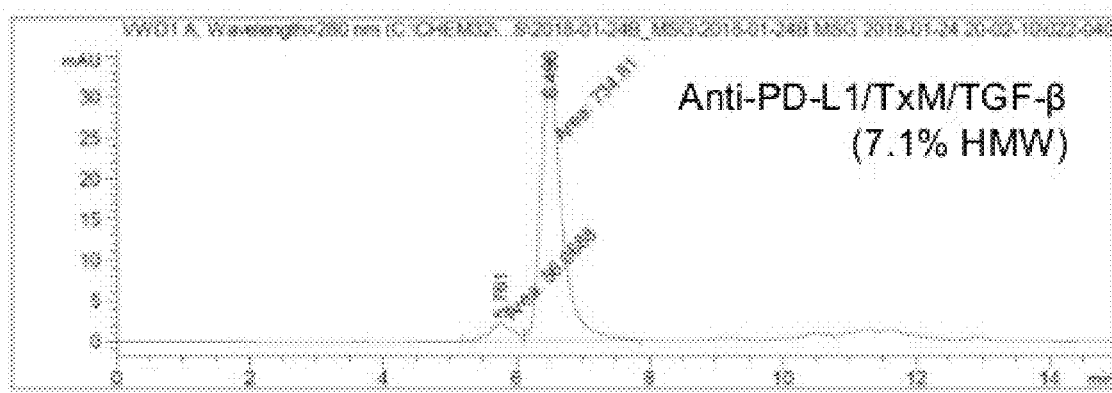
FIG. 22D are results from a SEC-HPLC of αPDL1/TxM/TGFβRII showing 93% purity.
Figure 22E:
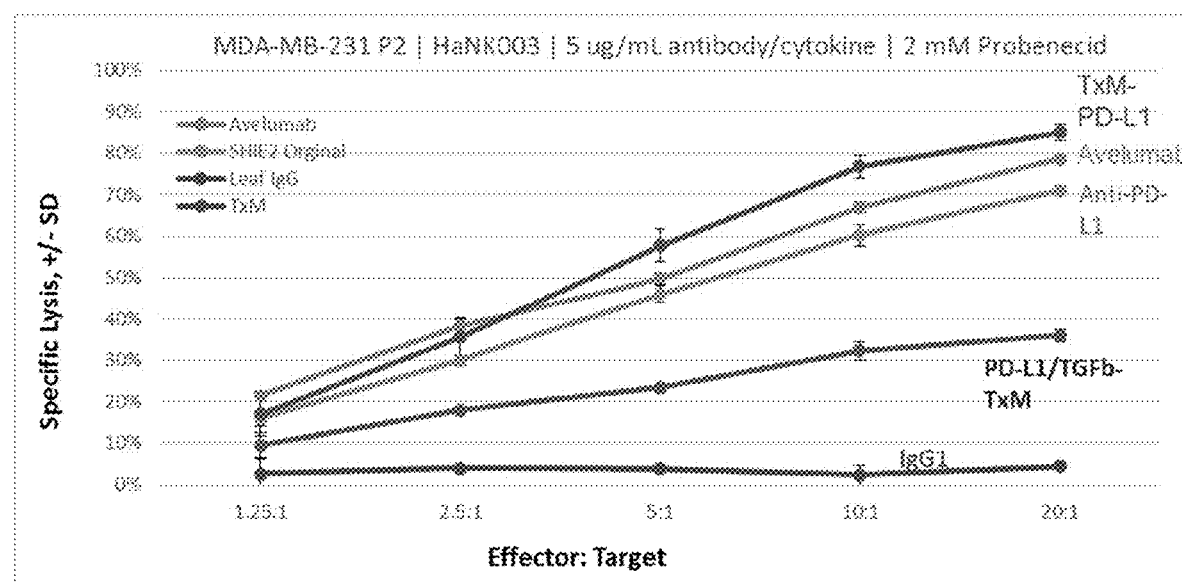
FIG. 22E demonstrate the ADCC activity of αPD-L1/TxM, Avelumab, Rsbc6 (Anti-PD-L1), αPDL1/TxM/TGFβRIIR against PD-L-positive tumor cells (MDA-MB-231 breast tumor cells). αPD-L1/TxM shows a maximal killing of ~85% whereas αPDL1/TxM/TGFβRII shows a maximal killing of ~30%.

As shown in FIGS. 20 and 21, both the TGFβRII/αPDL1/ TXM and αPDL1/TGFβRII/TXM fusion protein complexes were capable of mediating ADCC against PD-L1 expressing tumor cells. In fact, TGFβRII/αPDL1/TXM exhibited greater ADCC than equivalent molar concentrations of an anti-PD-L1 IgG1 antibody. Similar results were observed with PD-L-positive human HCC4006 lung cancer cells, CaSki cervical cancer cells and MDA-MB-231 breast cancer cells. Additionally, the αPDL1/TXM/TGFβRII complex exhibited ADCC activity against PD-L-positive human cancer cells (FIG. 22).

Figure 24:
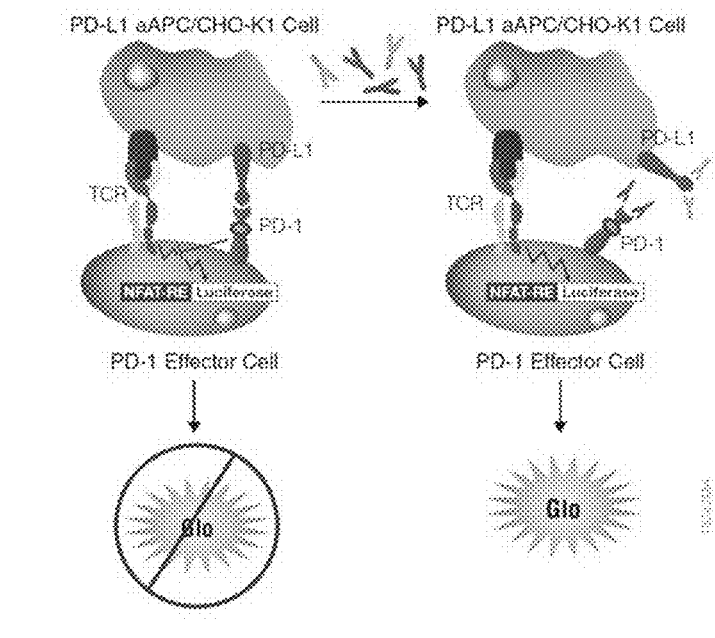
FIG. 24 is a schematic diagram of a standardize PD-L1 blockade assay to evaluate immune checkpoint activity of proteins.
Figure 24:
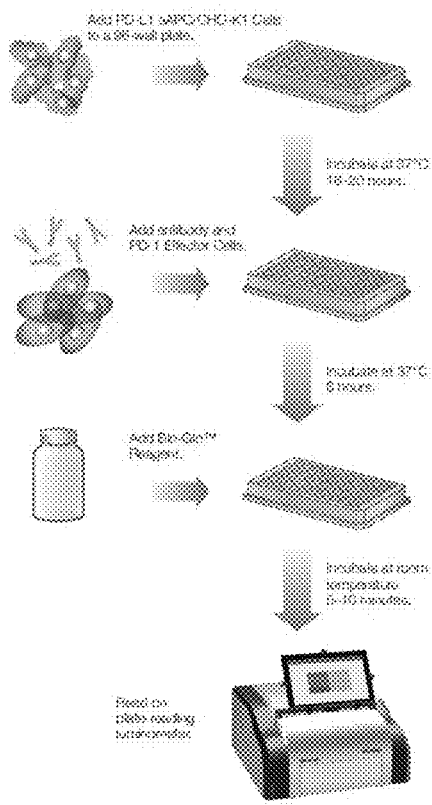

Inhibition of PD-L1 Activity:

In addition to assessment of PD-L1 binding activity and ADCC activity against PD-L1 positive tumor cells, we evaluated the ability to the TGFβRII/αPDL1/TXM and αPDL1/TGFβRII/TXM complexes to inhibit the immunosuppressive (checkpoint) activity of PD-L1 on PD-1 positive effector cells. In a standardized assay, artificial antigen presenting cells (aAPCs) expressing human PD-L1 and an engineered cell surface protein designed to activate cognate TCRs in an antigen-independent manner are mixed with Jurkat T cells expressing human PD-1 and a luciferase reporter driven by an NFAT response element. When the two cell types are co-cultured, the PD-1/PD-L1 interaction inhibits TCR signaling and NFAT-RE-mediated luminescence. Addition of either an anti-PD-1 or anti-PD-L1 antibody domain that blocks the PD-1/PD-L1 interaction releases the inhibitory signal and results in TCR activation and NFAT-RE-mediated luminescence (FIG. 23). The activities of the TGFβRII/αPDL1/TXM and αPDL1/TGFβRII/TXM complexes were assessed in this assay using standard procedures (FIG. 24). Anti-PD-L1 antibody and PD-L1/TxM protein complexes (similar to TGFβRII/αPDL1/TXM and αPDL1/TGFβRII/TXM complexes but lacking the TGFβRII domains) served as positive controls.

Figure 25A:
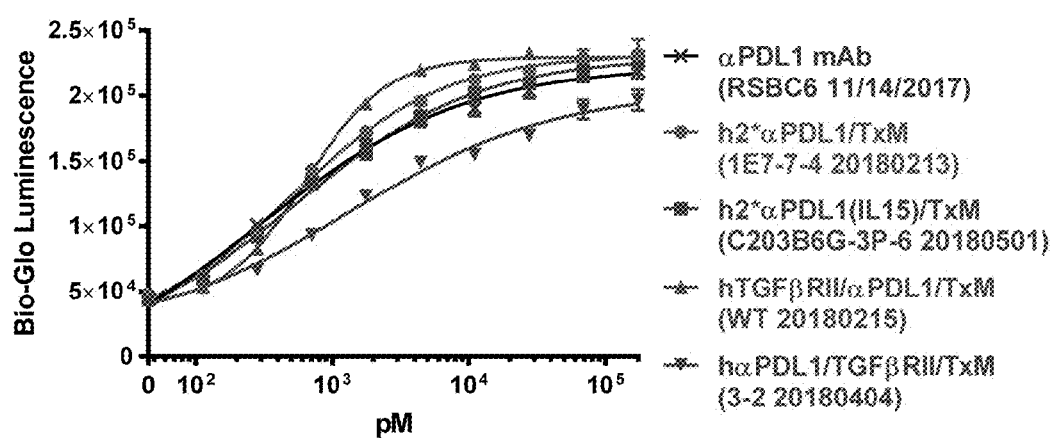
FIG. 25A is a graph showing results obtained from blocking of PD-L1 mediated immune cell suppression by hαPDL1/TGFβRII/TxM and hTGFβRII/αPDL1/TxM compared to αPDL1 Ab.
Figure 25B:
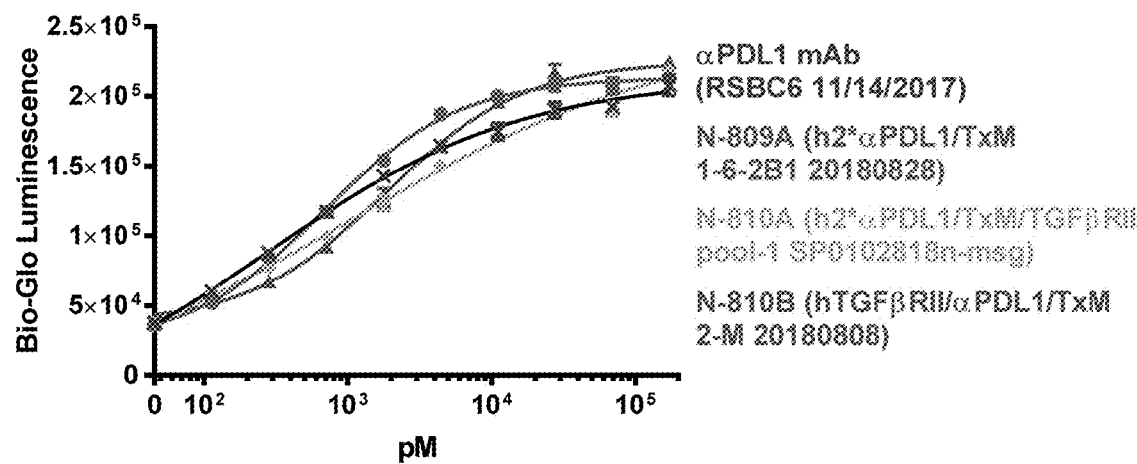
FIG. 25B is a graph showing results obtained from blocking of PD-L1 mediated immune cell suppression by hαPDL1/TxM/TGFβRII and hTGFβRII/αPDL1/TxM compared to αPDL1 Ab. Increasing concentrations of hαPDL1/TGFβRII/TxM, hTGFβRII/αPDL1/TxM and hαPDL1/TxM/TGFβRII were added to a standardized cell-based PD-L1 blockade assay (FIG. 24). The ability of the complexes to block immune suppression was measured by T cell activation resulting in NFAT-RE-mediated luminescence. Anti-PD-L1 antibody and PD-L1/TxM protein complexes (similar to TGFβRII/αPDL1/TXM and αPDL1/TGFβRII/TXM complexes but lacking the TGFβRII domains) served as positive controls.

As shown in FIGS. 25A and 25B, αPDL1/TGFβRII/TXM, TGFβRII/αPDL1/TXM and αPDL1/TXM/TGFβRII complexes were capable of inducing NFAT-RE-mediated luminescence in a dose dependent manner with similar activity as the anti-PD-L1 Ab control. These results verify that αPDL1/TGFβRII/TXM, TGFβRII/αPDL1/TXM and αPDL1/TXM/TGFβRII complexes retain immune checkpoint blockade activity.

Figure 26A:
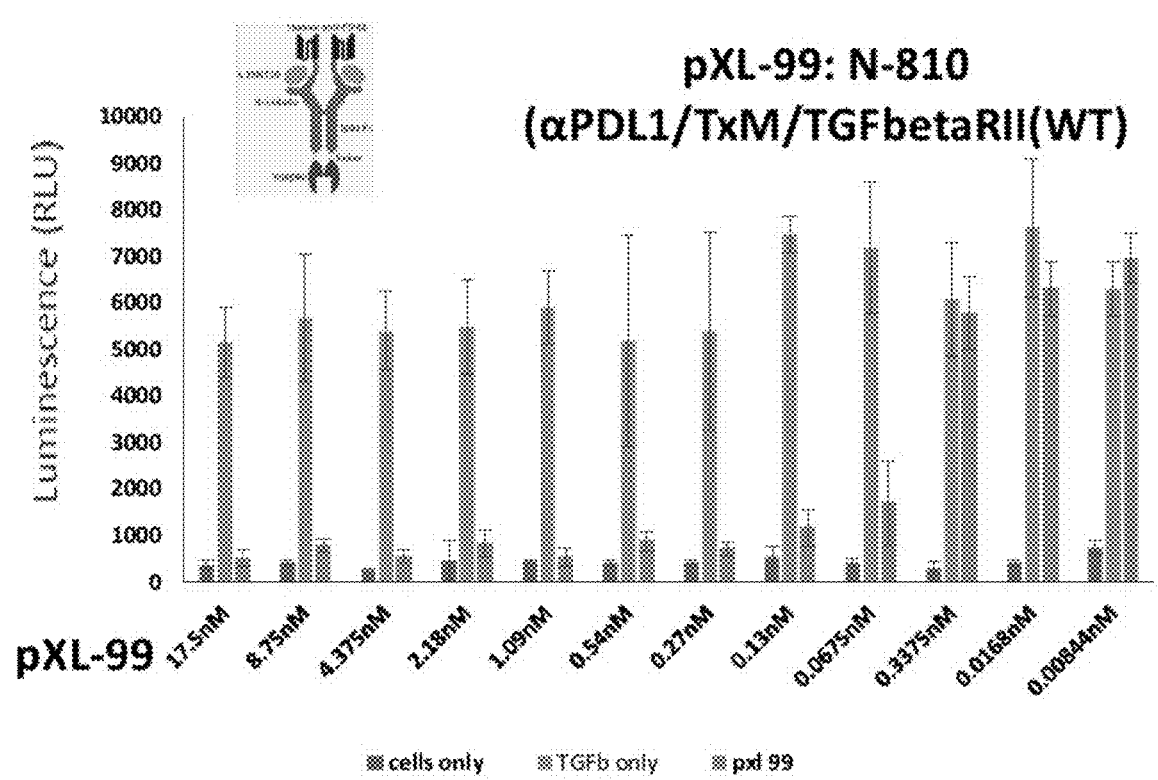
FIGS. 26A and 26B are graphs demonstrating the human TGFβ specific blocking activity for each molecule (N-810, FIG. 26A) compared against the activity of the parental control molecule (αPDL1/TxM, FIG. 26B). A stable cellular luciferase-based reporter system (HEK-293T-luc2P/SBE) was used in order to assess the specific TGFβ-blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.
Figure 26B:
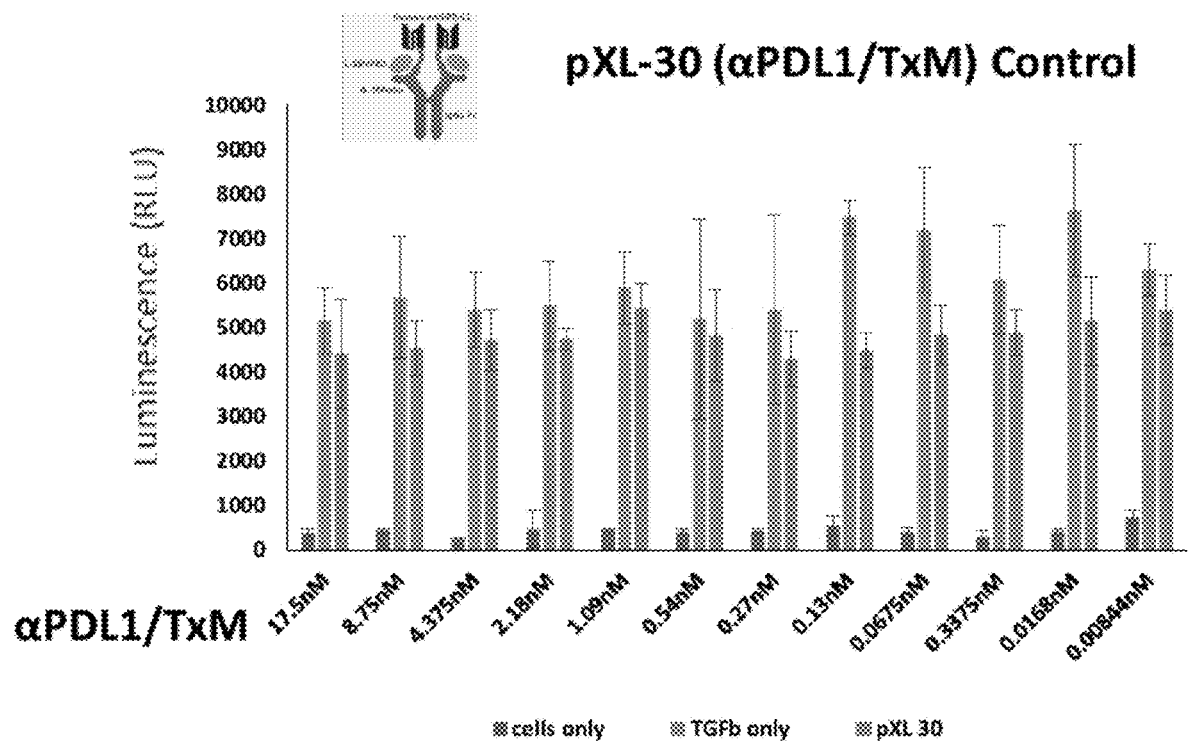

N-810:

FIGS. 26A and 26B demonstrate the human TGFβ specific blocking activity for N-810 (FIG. 26A) compared against the activity of the parental control molecule, αPDL1/ TxM (FIG. 26B). A stable cellular luciferase-based reporter system (HEK-293T-luc2P/SBE) was used in order to assess the specific TGFβ-blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.

Figure 27A:
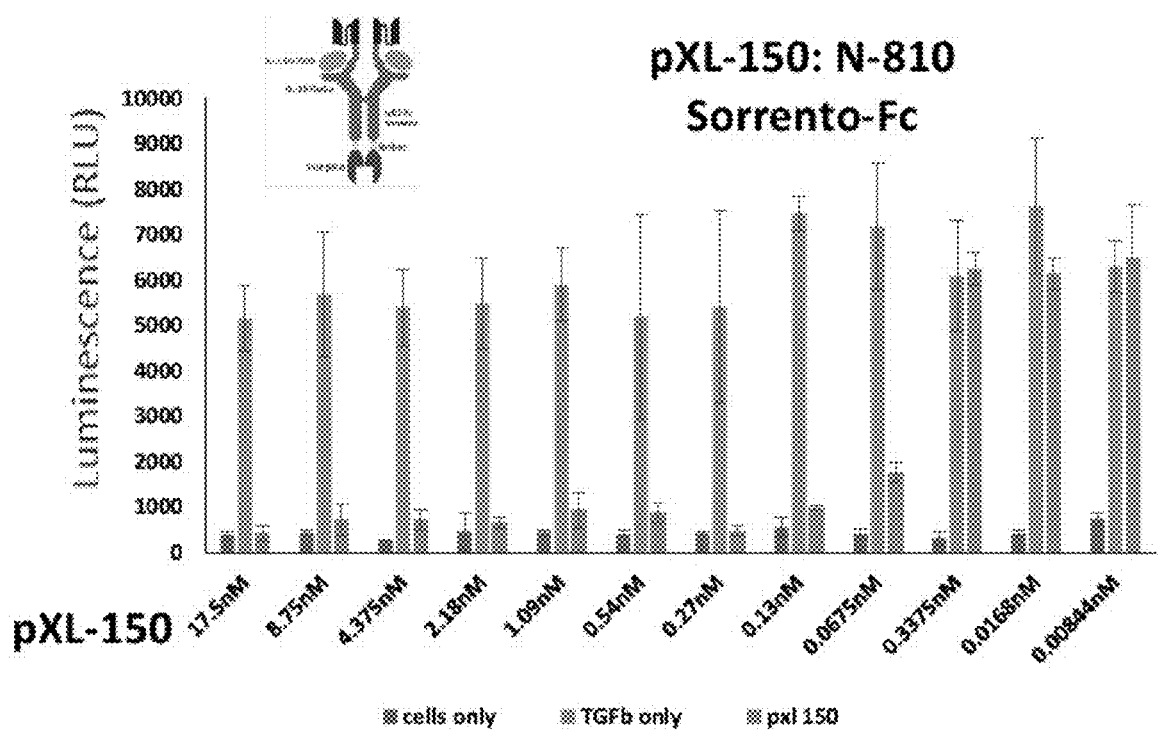
FIGS. 27A and 27B are graphs demonstrating specific hTGFβ1 blocking activity for each molecule (N-810 Sorrento-Fc, FIG. 27A) compared against the activity of the parental control molecule (αPDL1/TxM, FIG. 27B). A stable cellular luciferase-based reporter system (HEK-293T-luc2P/SBE) was used in order to assess the specific TGFβ- blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.
Figure 27B:
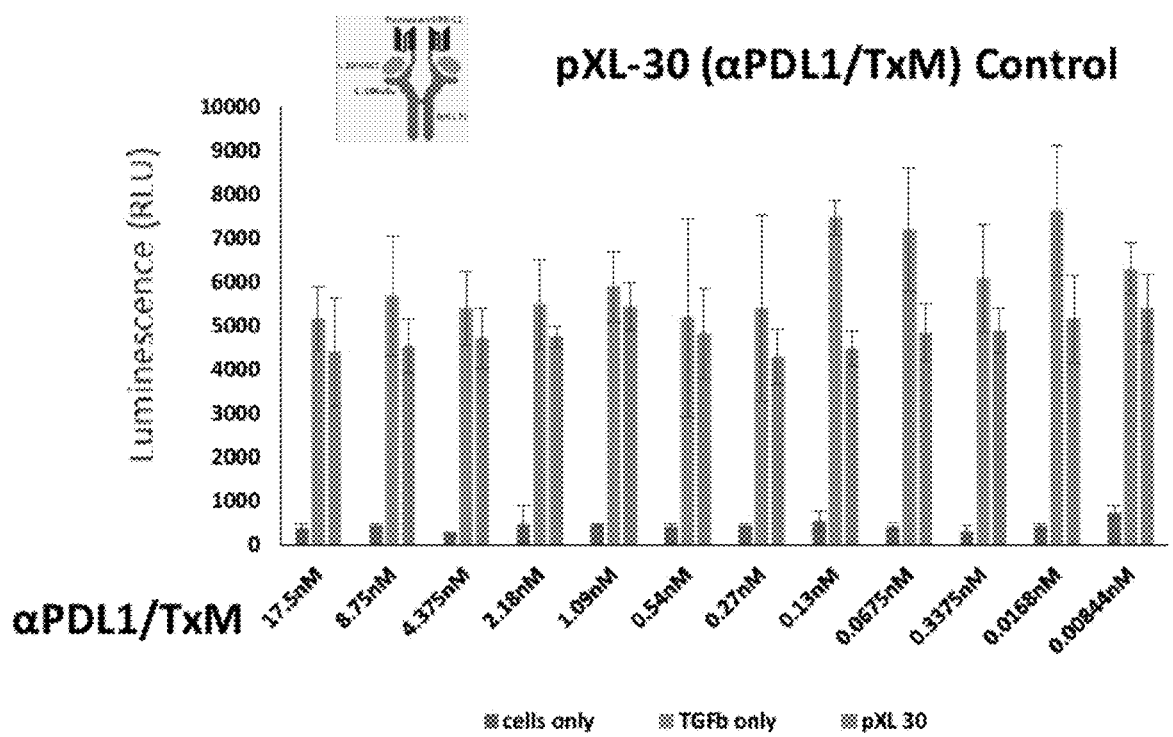

N-810 Sorrento-Fc:

FIGS. 27A and 27B demonstrate specific hTGFβ1 blocking activity for N-810 Sorrento-Fc (FIG. 27A) compared against the activity of the parental control molecule, αPDL1/ TxM (FIG. 27B). A stable cellular luciferase-based reporter system (HEK-293T-luc2P/SBE) was used in order to assess the specific TGFβ-blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.

N-810 Δ C:

FIGS. 28A and 28B demonstrate specific hTGFβ1 blocking activity for N-810 Δ C (FIG. 28A) compared against the activity of the parental control molecule, αPDL1/TxM (FIG. 28B). A stable cellular luciferase-based reporter system (HEK-293T-luc2P/SBE) was used in order to assess the specific TGFβ-blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.

N-810 D:

FIGS. 29A and 29B are graphs demonstrating specific hTGFβ1 blocking activity for N-810D (FIG. 29A) compared against the activity of the parental control molecule (αPDL1/TxM, FIG. 29B). A stable cellular luciferase-based reporter system (HEK-293T-luc2P/SBE) was used in order to assess the specific TGFβ-blocking activity. Cultured cells were stimulated for 20 hours with 0.0175 nM of recombinant human TGFβ1 in the presence or absence of the blocking reagent. Response to hTGFβ1 was expressed by Relative Luminescence Units (RLU)±SD.

Antibody-dependent cellular cytotoxicity (ADCC) of the TxM constructs: FIG. 30 is a graph demonstrating the antibody-dependent cellular cytotoxicity (ADCC) of the TxM constructs in mammary adenocarcinoma cells (MDA-MB-231). Antibody-Dependent Cellular Cytotoxicity (ADCC) was used in order to determine the specific αPD-L1 activity. Effector cells: haNK (NK-92 derivative).

TxM Constructs:

FIGS. 31A-31H are schematic representations showing the various constructs. FIG. 31A: N-810A. FIG. 31B: N-810A aglycosylated. FIG. 31C: N-810A aglycosylated, A free cysteine. FIG. 31D: N-810Δ A hinge. FIG. 31E: N-810A (IL15-K41Q, L45S, I67T, N79Y, E93A). The mutations in IL15 enhance the solubility and expression of the molecule. FIG. 31F: N-810A (IL15-L45S). The mutations in IL15 enhance solubility and expression of the molecule. FIG. 31G: N-810D. FIG. 31H: N-810E.

FIG. 32 and Table 1 demonstrate that IL15 mutations increase protein yield and decrease aggregation. N-810D variation also increases yield and decreases aggregation.

| Protein | Post-harvest Titer (ug/mL) | Total Yield (mg) | High Molecular Weight % Post Pro-A |
|---|---|---|---|
| N-810A | 55.9 | | 20.4 |
| N-810 (IL15-K41Q, L45S, I67T, N79Y, E93A) | 156.3 | 6.7 | 18.1 |
| N810A (IL15-L45S) | 151.3 | 6.6 | 16.5 |
| N810D | 117.7 | | 8.8 |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference.

Genbank and NCBI submissions indicated by accession number cited herein are hereby incorporated by reference. All other published references, documents, manuscripts, and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated soluble fusion protein complex comprising at least
a first soluble protein and a second soluble protein,
wherein the first soluble protein has at least 85% sequence identity to the amino acid sequence of SEQ ID NO:2,
wherein the second soluble protein has at least 85% sequence identity to the amino acid sequence of SEQ ID NO:4, and
wherein an IL-15 domain of the first soluble protein binds to an IL-15RαSu domain of the second soluble protein to form the soluble fusion protein complex.

2. The soluble fusion protein complex of claim 1, wherein the first soluble protein comprises a transforming growth factor-beta receptor type 2 (TGFβRII) domain bound to transforming factor beta (TGFβ).

3. The soluble fusion protein complex of claim 1, wherein the fusion protein complex is covalently linked to a second fusion protein complex by a disulfide bond linking an Fc domain of the soluble fusion protein complex to an Fc domain of the second soluble fusion protein complex.

4. The soluble fusion protein complex of claim 1, wherein the first soluble protein has at least 95% sequence identity to the amino acid sequence of SEQ ID NO:2.

5. The soluble fusion protein complex of claim 4, wherein the first soluble protein comprises the amino acid sequence of SEQ ID NO:2.

6. The soluble fusion protein complex of claim 4, wherein the second soluble protein has at least 95% sequence identity to the amino acid sequence of SEQ ID NO:4.

7. The soluble fusion protein complex of claim 6, wherein the second soluble protein comprises the amino acid sequence of SEQ ID NO:4.

8. An isolated soluble fusion protein complex comprising at least a first soluble protein and a second soluble protein, wherein the first soluble protein has at least 85% sequence identity to the amino acid sequence of SEQ ID NO:6, wherein the second soluble protein has at least 85% sequence identity to the amino acid sequence of SEQ ID NO:8, and
wherein an IL-15 domain of the first fusion protein binds to an IL-15RαSu domain of the second fusion protein to form the soluble fusion protein complex.

9. The soluble fusion protein complex of claim 8, wherein the first soluble protein is bound to programmed death ligand 1 (PD-L1).

10. The soluble fusion protein complex of claim 8, wherein the second soluble protein comprises a transforming growth factor-beta receptor type 2 (TGFβRII) bound to transforming growth factor beta (TGFβ).

11. The soluble fusion protein complex of claim 8, wherein a first fusion protein complex is covalently linked to a second fusion protein complex by a disulfide bond linking an Fc domain of the first soluble fusion protein complex to an Fc domain of the second soluble fusion protein complex.

12. The soluble fusion protein complex of claim 8, wherein the first soluble protein has at least 95% sequence identity to the amino acid sequence of SEQ ID NO:6.

13. The soluble fusion protein complex of claim 12, wherein the first soluble protein comprises the amino acid sequence of SEQ ID NO:6.

14. The soluble fusion protein complex of claim 12, wherein the second soluble protein has at least 95% sequence identity to the amino acid sequence of SEQ ID NO:8.

15. The soluble fusion protein complex of claim 14, wherein the second soluble protein comprises the amino acid sequence of SEQ ID NO:8.

16. A nucleic acid sequence comprising a sequence selected from the group consisting of SEQ ID NO: 1, 3, 5, 7, 9, 11, 13, 15, 16, 17, 18, and 19.

17. The nucleic acid sequence of claim 16, wherein the nucleic acid sequence further comprises a promoter, translation initiation signal, and leader sequence operably linked to the sequence.

* * * * *

UNITED STATES PATENT AND TRADEMARK OFFICE
CERTIFICATE OF CORRECTION

PATENT NO. : 11,168,138 B2
APPLICATION NO. : 16/365587
DATED : November 9, 2021
INVENTOR(S) : Li et al.

Page 1 of 1

It is certified that error appears in the above-identified patent and that said Letters Patent is hereby corrected as shown below:

In the Claims

In Column 173, Claim 2, Lines 45-46, please delete "factor-beta receptor type 2 (TGFβRII domain bound to transforming factor beta (TGFβ" and insert --factor-beta receptor type 2 (TGFβRII) domain bound to transforming factor beta (TGFβ)--

In Column 174, Claim 10, Line 44, please delete "transforming growth factor beta (TGFβ." and insert --transforming growth factor beta (TGFβ).--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*